United States Patent
Babich et al.

(10) Patent No.: US 11,712,485 B2
(45) Date of Patent: *Aug. 1, 2023

(54) TRIAZINE BASED RADIOPHARMACEUTICALS AND RADIOIMAGING AGENTS

(71) Applicant: Molecular Insight Pharmaceuticals, Inc., New York, NY (US)

(72) Inventors: John W. Babich, New York, NY (US); Craig Zimmerman, Topsfield, MA (US); John L. Joyal, Melrose, MA (US); Genliang Lu, Winchester, MA (US)

(73) Assignee: Molecular Insight Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/129,825

(22) Filed: Dec. 21, 2020

(65) Prior Publication Data

US 2021/0338850 A1 Nov. 4, 2021

Related U.S. Application Data

(60) Continuation of application No. 16/231,153, filed on Dec. 21, 2018, now Pat. No. 10,898,598, which is a continuation of application No. 15/233,096, filed on Aug. 10, 2016, now Pat. No. 10,201,624, which is a division of application No. 14/152,864, filed on Jan. 10, 2014, now Pat. No. 9,447,121.

(60) Provisional application No. 61/785,788, filed on Mar. 14, 2013, provisional application No. 61/752,350, filed on Jan. 14, 2013.

(51) Int. Cl.
| | |
|---|---|
| *A61K 51/04* | (2006.01) |
| *C07D 401/14* | (2006.01) |
| *C07D 403/14* | (2006.01) |
| *C07D 413/14* | (2006.01) |
| *C07F 5/00* | (2006.01) |
| *A61B 6/00* | (2006.01) |

(52) U.S. Cl.
CPC .......... *A61K 51/0497* (2013.01); *A61B 6/481* (2013.01); *A61B 6/50* (2013.01); *C07D 401/14* (2013.01); *C07D 403/14* (2013.01); *C07D 413/14* (2013.01); *C07F 5/003* (2013.01)

(58) Field of Classification Search
CPC .... A61K 51/00; A61K 51/04; A61K 51/0497; A61K 2121/00; A61K 2123/00; A61B 6/481; A61B 6/50; C07D 401/14; C07D 403/14; C07D 413/14; C07F 5/003; A61P 1/04; A61P 1/16; A61P 1/18; A61P 11/00; A61P 13/08; A61P 13/10; A61P 13/12; A61P 15/00; A61P 17/00; A61P 19/00; A61P 25/00; A61P 35/00; A61P 43/00

USPC .......... 424/1.11, 1.65, 1.69, 1.81, 9.1, 9.2; 534/7, 10–16

See application file for complete search history.

(56) References Cited

U.S. PATENT DOCUMENTS

| | | |
|---|---|---|
| 2,730,456 A | 1/1956 | Green et al. |
| 2,730,457 A | 1/1956 | Green et al. |
| 2,800,457 A | 7/1957 | Green et al. |
| 3,527,789 A | 9/1970 | Payne |
| 3,625,214 A | 12/1971 | Higuchi |
| 4,272,398 A | 6/1981 | Jaffe |
| 4,798,734 A | 1/1989 | Kaneda |
| 4,885,136 A | 12/1989 | Katayama et al. |
| 4,885,363 A | 12/1989 | Tweedle et al. |
| 4,888,136 A | 12/1989 | Chellapa et al. |
| 4,906,474 A | 3/1990 | Langer et al. |

(Continued)

FOREIGN PATENT DOCUMENTS

| | | |
|---|---|---|
| CN | 102272102 | 12/2011 |
| EP | 0 544 412 A2 | 6/1993 |

(Continued)

OTHER PUBLICATIONS

"Amino Acid," Wikipedia, 2015, https://en.wikipedia.org/wiki/Amino_acid.

(Continued)

*Primary Examiner* — D. L. Jones
(74) *Attorney, Agent, or Firm* — Foley & Lardner LLP

(57) ABSTRACT

Metal complexes including a radionuclide and a compound of Formula I and Formula II are potent inhibitors of PSMA.

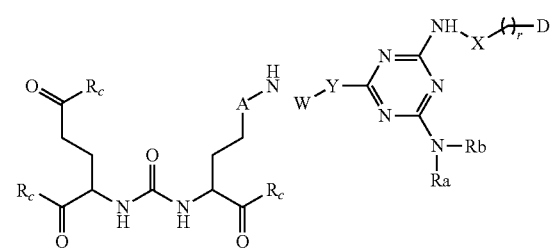

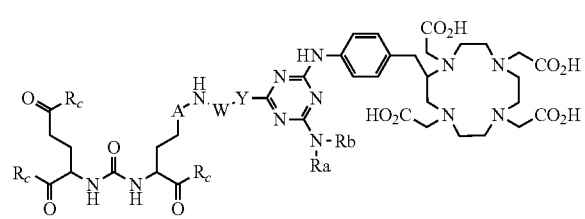

20 Claims, 6 Drawing Sheets

(56) References Cited

U.S. PATENT DOCUMENTS

| | | | |
|---|---|---|---|
| 4,925,673 | A | 5/1990 | Steiner et al. |
| 5,442,088 | A | 8/1995 | Hoffmann |
| 5,514,505 | A | 5/1996 | Limburg et al. |
| 5,672,592 | A | 9/1997 | Jackson et al. |
| 5,739,123 | A | 4/1998 | Norcini et al. |
| 5,795,877 | A | 8/1998 | Jackson et al. |
| 5,824,662 | A | 10/1998 | Slusher et al. |
| 5,880,112 | A | 3/1999 | Jackson et al. |
| 6,071,965 | A | 6/2000 | Jackson et al. |
| 6,479,470 | B1 | 11/2002 | Kozikowski et al. |
| 6,528,499 | B1 | 3/2003 | Kozikowski et al. |
| 7,381,745 | B2 | 6/2008 | Kozikowski et al. |
| 7,829,065 | B2 | 11/2010 | Supuran et al. |
| 8,211,402 | B2 | 7/2012 | Babich et al. |
| 8,926,944 | B2 | 1/2015 | Babich et al. |
| 9,447,121 | B2 * | 9/2016 | Babich ................... A61B 6/481 |
| 10,086,096 | B2 * | 10/2018 | Babich ................... A61P 13/10 |
| 10,201,624 | B2 * | 2/2019 | Babich ...................... A61P 1/18 |
| 10,898,598 | B2 * | 1/2021 | Babich ................... C07F 5/003 |
| 2003/0100594 | A1 | 5/2003 | Masferrer et al. |
| 2003/0235843 | A1 | 12/2003 | Babich et al. |
| 2004/0002478 | A1 | 1/2004 | Kozikowski et al. |
| 2004/0054190 | A1 | 3/2004 | Pomper et al. |
| 2004/0191174 | A1 | 9/2004 | Linder et al. |
| 2004/0209921 | A1 | 10/2004 | Bridger et al. |
| 2005/0038258 | A1 | 2/2005 | Koike et al. |
| 2006/0057068 | A1 | 3/2006 | Supuran et al. |
| 2006/0155021 | A1 | 7/2006 | Lenges et al. |
| 2006/0155146 | A1 | 7/2006 | Lenges et al. |
| 2006/0198785 | A1 | 9/2006 | Santos |
| 2008/0176821 | A1 | 7/2008 | Kozikowski et al. |
| 2008/0227962 | A1 | 9/2008 | Mazzanti |
| 2009/0175794 | A1 | 7/2009 | Zimmerman et al. |
| 2009/0192182 | A1 | 7/2009 | Kusumi et al. |
| 2010/0140483 | A1 | 6/2010 | Rousso et al. |
| 2010/0178246 | A1 | 7/2010 | Babich et al. |
| 2010/0178247 | A1 | 7/2010 | Babich et al. |
| 2010/0183509 | A1 | 7/2010 | Babich et al. |
| 2011/0183954 | A1 | 7/2011 | Almeida et al. |
| 2012/0009121 | A1 | 1/2012 | Pomper et al. |
| 2016/0346410 | A1 | 12/2016 | Babich et al. |

FOREIGN PATENT DOCUMENTS

| | | |
|---|---|---|
| EP | 0 878 463 | 11/1998 |
| EP | 1 389 460 A1 | 2/2004 |
| EP | 1 550 657 A1 | 7/2005 |
| EP | 1 961 744 A1 | 8/2008 |
| JP | 04-342560 A | 11/1992 |
| JP | 05-239046 | 9/1993 |
| JP | 08-282117 | 10/1996 |
| JP | 08-314240 A | 11/1996 |
| JP | 2002-506858 | 3/2002 |
| JP | 2005-539023 | 12/2005 |
| JP | 2006-509844 | 3/2006 |
| JP | 2007-523902 | 8/2007 |
| JP | 2007-524685 | 8/2007 |
| JP | 2010-509358 A | 3/2010 |
| JP | 2010-523599 | 7/2010 |
| JP | 2012-511023 | 5/2012 |
| JP | 5220203 B2 | 5/2012 |
| JP | 2016-511231 A | 4/2016 |
| WO | WO-97/48399 | 12/1997 |
| WO | WO-97/48400 | 12/1997 |
| WO | WO-97/48409 | 12/1997 |
| WO | WO-98/13046 | 4/1998 |
| WO | WO-98/45256 | 10/1998 |
| WO | WO-98/45257 | 10/1998 |
| WO | WO-99/33847 | 7/1999 |
| WO | WO-99/47507 | 9/1999 |
| WO | WO-00/64911 | 11/2000 |
| WO | WO-01/01974 | 1/2001 |
| WO | WO-02/22627 | 3/2002 |
| WO | WO-03/013617 A2 | 2/2003 |
| WO | WO-03/060523 | 7/2003 |
| WO | WO-03/077727 A2 | 9/2003 |
| WO | WO-2004/014352 A2 | 2/2004 |
| WO | WO-2005/056520 A1 | 6/2005 |
| WO | WO 2005/079865 A1 | 9/2005 |
| WO | WO-2005/079865 A1 | 9/2005 |
| WO | WO-2006/032911 | 3/2006 |
| WO | WO-2006/080993 A2 | 8/2006 |
| WO | WO-2006/093991 | 9/2006 |
| WO | WO-2006/116736 | 11/2006 |
| WO | WO-2007/008848 | 1/2007 |
| WO | WO-2007/031640 | 3/2007 |
| WO | WO-2007/042504 A2 | 4/2007 |
| WO | WO-2007/090461 A1 | 8/2007 |
| WO | WO-2007/148738 A1 | 12/2007 |
| WO | WO-2008/016006 | 2/2008 |
| WO | WO-2008/028000 A2 | 3/2008 |
| WO | WO 2008/058192 A2 | 5/2008 |
| WO | WO-2008/058192 A2 | 5/2008 |
| WO | WO-2008/124703 A2 | 10/2008 |
| WO | WO-2009/076434 A1 | 6/2009 |
| WO | WO-2009/089383 A2 | 7/2009 |
| WO | WO-2010/036814 A1 | 4/2010 |
| WO | WO-2010/065899 A2 | 6/2010 |
| WO | WO-2010/065902 A2 | 6/2010 |
| WO | WO-2010/065906 A2 | 6/2010 |
| WO | WO 2010/096486 A1 | 8/2010 |
| WO | WO 2010/108125 A2 | 9/2010 |
| WO | WO 2011/098611 A2 | 8/2011 |
| WO | WO 2012/074840 A2 | 6/2012 |
| WO | WO 2012/078534 A1 | 6/2012 |
| WO | WO-2013/022797 A2 | 2/2013 |
| WO | WO-2013/166110 | 11/2013 |

OTHER PUBLICATIONS

"Definition of Radical", Google, 2015, https://www.google.com/search ?q=defin ition of radical&sourceid=ie 7 &rls=com. microsoft: en -us: IEAddress& ie=&oe=&gws_rd=ssl.

Alberto et al., "A Novel Organometallic Aqua Complex of Technetium for the Labeling of Biomolecules: Synthesis of [99mTc(OH2)3(CO3)]+ from [99mTcO4]- in Aqueous Solution and Its Reaction with a Bifunctional Ligand", Journal of American Chemical Society, American Chemical Society, vol. 120, No. 31, 1998, pp. 7987-7988.

Babich, et al., "Applications of Nuclear Imaging in Drug Discovery and Development," Drug Discovery Dev., 2006, vol. 1, pp. 365-381.

Banerjee et al., "{RE(III)Cl3} Core Complexes with Bifunctional Single Amino Acid Chelates", Inorganic Chemistry, American Chemical Society, vol. 41, No. 22, 2002, pp. 5795-5802.

Banerjee et al., Bifunctional Single Amino Acid Chelates for Labeling of Biomolecules with the {Tc(CO)3} and {Re(CO)3} Cores. Crystal and Molecular Structures of [ReBr(CO)3(H2NCH2C5H4N)], [Re(CO)3{C5H4NCH2)2NH}Br, [Re(CO)3{C5H4NCH2)2NCH2CO2H}Br, [Re(CO)3{X(Y)NCH2CO2CH2CH3}Br(X=Y=2-pyridylmethyl; X=2-pyridylmethyl, Y=2-(1-methylimidazolyl)methyl,[ReBr(CO)3{C5H 4NCH2)NH(CH2C4H3S)}], and [Re(CO)3{C5H4NCH2)N(CH2C4H3S)(CH2CO2)}], Inorganic Chemistry, vol. 41, No. 24, 2002, pp. 6417-6425.

Banerjee et al., "Synthesis and Evaluation of Technetium-99m- and Rhenium-Labeled Inhibitors of the Prostate-Specific Membrane Antigen (PSMA)", Journal of Medicinal Chemistry, vol. 15, pp. 4504-4517, 2008.

Banerjee, A. et al. "Inhibition of matrix metalloproteinase-9 by "multi-prong" surface binding groups", Chem. Commun., 2005, No. 20, pp. 2549-2551.

Berthommier, E., et al., "New preparation of [123I]PE2I: investigation of the oxidation and purification steps," J. Label Compd Radiopharm, 2002, vol. 45, No. 12, pp. 1019-1028.

Carter et al., "Prostate-Specific Membrane Antigen is a Hydrolase with Substrate and Pharacologic Characteristics of a Neuropeptidase," Proc. Nat. Acad. Sci., USA, 93:749-753, Jan. 1996.

Chen et al., "Radiohalogenated Prostate-Specific Membrane Antigen (PSMA)-Based Ureas as Imaging Agents for Prostate Cancer", Journal of Medicinal Chemistry, vol. 51, 2008, pp. 7933-7943.

(56) References Cited

OTHER PUBLICATIONS

Chen, et al., "Age-related decrease in cardiopulomnary andrenergic neuronal function in children as assessed by I-123 metaiodobenzylgucanidine imaging," J. Nucl. Cardiol., 2008, vol. 15, No. 1, pp. 73-79.
Communication pursuant to Article 94(3) EPC in EP Appln No. 09 775 430.3 dated Aug. 8, 2013.
Dischino et al., "Synthesis of nonionic gadolinium chelates useful as contrast agents for magnetic resonance imaging: 1,4,7,-tris (carboxymethyl) -10-substituted-1,4,7,10-tetraazacyclododecanes and their corresponding gadolinium chelates," Inorganic Chemistry, 1991, vol. 30, No. 6, pp. 1265-1269, Caplus an 1991 :177144.
Donovan et al., XP002614474 "Fluorous Isocyanates: Convenient Synthons for the Preparation of Radioiodinated Compounds in High Effective Specific Activity", Journal of Organic Chemistry, vol. 74, Oct. 2, 2009, pp. 8133-8138.
European Search Report in Application No. 07844938.6 dated Jun. 13, 2012.
Examination Report dated Jul. 22, 2014 in Austalia Application No. 2009322171.
Examination Report dated Jul. 29, 2014 in Australia Application No. 2009322167.
Extended European Search Report dated Apr. 28, 2016 in related EP Appl. 14738117.2 (5 pgs.).
First Examination Report in AU Appln No. 2010260195 dated Jul. 30, 2014.
Flux, et al., "Absorbed Dose Ratios for Repeated Therapy of Neuroblastoma with I-131 mIBG," Cancer Biother., Radiopharm., 2003, vol. 18, No. 1, pp. 81-87.
Foss et al., "Radiolabeled Small-Molecule Ligands for Prostate-Specific Membrane Antigen: In Vivo Imaging in Experimental Models of Prostate Cancer," Clin. Cancer Res., 11(11):4022-4028 (2005).
Fullerton, et al., "Comparison of Radiohaloanalogues of Meta-Iodobenzylguanidine (MIBG) for a Combined Gene-and Targeted Radiotherapy Approach to Bladder Carcinoma," Med. Chem., 2005, vol. 1, pp. 611-618.
Gasparini et al., "(R,S)-4-Phosphononphenylglycine, a Potent and Selective Group III Metabotropic Glutamate Receptor Agonist, is Anticonvulsive and Neuroprotective in Vivo," J. Pharm. Exper. Ther., 290(3):1678-1687 (1999).
Hayakawa et al., XP-002614476 "Second-Generation Total Synthesis of Haterumalide NA Using B-Alkyl Suzuki-Miyaura Coupling", Organic Letters, vol. 10, No. 9, 2008, pp. 1859-1862.
Heidenreich et al., EAU guidelines on prostate cancer, European Urology, 2008, vol. 53, pp. 68-80.
International Search Report and Written Opinion in PCT/US2009/066836 dated Dec. 28, 2010.
International Search Report and Written Opinion dated Mar. 30, 2011 in International Applicaton No. PCT/US2009/066842.
International Search Report and Written Opinion of the International Searching Authority issued in International Application No. PCT/US2014/061249 dated Apr. 3, 2015.
International Search Report in International Application No. PCT/US00/11262, dated Sep. 12, 2000.
International Search Report in International Application No. PCT/US07/83934, dated Mar. 13, 2008.
Invitation to Pay Additional Fees dated May 17, 2010 in International Application No. PCT/US2009/066836.
Invitation to Pay Additional Fees dated May 17, 2010 in International Application No. PCT/US2009/066842.
Izdebski et al., "Synthesis of N,N'-Carbonyl-bis-amino Acids and N,N'-Carbonyl-bis-peptides," Polish J. Chem., 71(8):1066-1074, 1997.
Jackson et al., "Design, Synthesis, and Biological Activity of a Potent Inhibitor of the Neuropeptidase N-Acetylated alpha-Linked Acidic Dipeptidase," J. Med. Chem., 39(2):619-622, 1996.
Kozikowski et al., "Design of Remarkably Simple, Yet Potent Urea-Based Inhibitors of Glutamate Carboxypeptidase II (NAALADase)," J. Med. Chem. 44(3):298-301, 2001.

Kozikowski et al., "Synthesis of Urea-Based Inhibitors as Active Site Probes of Glutamate Carboxypeptidase II: Efficacy as Analgesic Agents," J. Med. Chem., 47:1729-1738 (2004).
Krebs, H.A., "Inhibition of Carbonic Anhydrase by Sulphonamides," The Biochemical Journal, vol. 43, 1948, pp. 525-528.
Lewis et al., "Maleimidocysteineamido-DOTA Derivatives: New Reagents for Radiometal Chelate Conjugation to Antibody Sulfhydryl Groups Undergo pH-Dependent Cleavage Reactions", Bioconjugate Chemistry, American Chemical Society, vol. 9, No. 1, 1998, pp. 72-86.
Lewis, Hawley's Condensed Chemical Dictionary, 12 Ed., Van Nostrand Reinhold Co., New York, NY, pp. 9, 420, 421, and 881, 1993.
Maresca, et al. "A series of halogenated Heterodimeric inhibitors of prostate specific membrane antigen (PSMA) as radiolabeled probes for targeting prostate cancer", Journal of Medicinal Chemistry, American Chemical Society, US, vol. 52, Jan. 22, 2009, pp. 347-357, XP002614472.
McIntee, et al., "A Convenient Method for the Preparation of Fluorous Tin Derivatives for the Fluorous Labeling Strategy" J. Org. Chem., 2008, vol. 73, pp. 8236-8243.
Moyer et al., "Screening for prostate cancer: U.S. preventive services task force recommendation statement," Ann Intern Med, May 22, 2012, vol. 157, No. 2, pp. 120-134.
Nan et al., "Dual Function Glutamate-Related Ligands: Discovery of a Novel, Potent Inhibitor of Glutamate Carboxypeptidase II Possessing mGluR3 Agonist Activity," J. Med. Chem., 43(5):772-774, 2000.
Non-Final Office Action issued in co-pending U.S. Appl. No. 14/820,953 dated Oct. 27, 2015.
Non-Final Office Action issued in U.S. Appl. No. 14/610,417 dated Jun. 26, 2015.
Non-Final Office Action issued in U.S. Appl. No. 12/815,637 dated Aug. 15, 2012.
Notice of Allowance issued in co-pending U.S. Appl. No. 13/890,912 dated Jun. 4, 2015.
Notice of Allowance received for U.S. Appl. No. 12/631,337 dated Mar. 15, 2012.
Notice of Allowance received for U.S. Appl. No. 12/631,343 dated Mar. 12, 2012.
Office Action cited in U.S. Appl. No. 12/029,367 dated Oct. 19, 2010.
Office Action for JP 2011-539755, dated Oct. 30, 2012.
Office Action for JP 2011-539755, dated Oct. 30, 2012—English Translation.
Office Action in CN Appln No. 200980153722.8 dated Oct. 30, 2012.
Office Action in CN Appln No. 200980153877.1 dated Apr. 8, 2014.
Office Action in CN Appln No. 200980153877.1 dated Sep. 17, 2013.
Office Action in CN Appln. No. 200980153877.1 dated Oct. 30, 2012.
Office Action in Japan Application No. 2011-539757 dated Jun. 17, 2014.
Office Action in JP Appln No. 2011-539757 dated Dec. 24, 2013.
Office Action in RU Appln No. 2011127467 dated Apr. 20, 2013.
Office Action in RU Appln No. 2011127468 dated Jul. 17, 2013.
Office Action issued in co-pending Chinese Application No. 200980153722.8 dated Jun. 5, 2015.
Office Action issued in co-pending Chinese Application No. 200980153878.6 dated Jul. 30, 2015.
Office Action issued in co-pending Japanese Application No. 2014-145241 dated Jul. 28, 2015 (with English Translation).
Office Action issued in co-pending U.S. Appl. No. 14/610,417, dated Jan. 14, 2016.
Office Action issued in corresponding Chinese application No. 200980153722.8 dated Dec. 15, 2015.
Office Action issued in U.S. Appl. No. 14/610,417 dated Dec. 22, 2015.
Partial International Search document received in connection with the Invitation to pay Additional Fees for PCT/US2010-038645; dated Mar. 21, 2011.

(56) References Cited

OTHER PUBLICATIONS

Rami, M. et al. "Carbonic Anhydrase Inhibitors: Design of Membrane-Impermeant Copper(II) Complexes of DTPA-, DOTA-, and TETA-Tailed Sulfonamides Targeting the Tumor-Associated Transmembrane Isoform IX", Chemmedchem, 2008, vol. 3, pp. 1780-1788.
Roy, B. et al., "Two-Prong Inhibitors for Human Carbonic Anhydrase II", Journal of American Chemical Society, vol. 126, 2004, pp. 13206-13207.
Sempuku, K., "Sulfur Compounds," 6001 Chemical Abstracts, Columbus Ohio, US, 101(27). XP002196919, 1984.
Slusher, et al., "Immunocytochemical Localization of the N-Acetyl-Aspartyl-Glutamate (NAAG) Hydrolyzing Enzyme N-Acetylated alpha-Linked Acidic Dipeptidase (NAALADase)," J. Compar. Neurol., 315(2):217-229, 1992.
Slusher, et al., "Rat Brain N-Acetylated alpha-Linked Acidic Dipeptidase Activity," J. Biolog. Chem., 265(34):21297-21301, 1990.
Uddin et al., XP-002614475 "Synthesis and evaluation of [123I]-indomethacin derivatives as COX-2 targeted imaging agents", Journal of Labelled Compounds and Radiopharmaceuticals, vol. 52, No. 2, May 2009, pp. 387-393.
U.S. Notice of Allowance dated Feb. 11, 2013.
U.S. Notice of Allowance dated Dec. 9, 2014.
U.S. Office Action dated May 16, 2014.
Yao, Zhen et al., Synthesis of Porphyrins Bearing 1-4 hydroxymethyl Groups and other One-carbon oxygenic Substituents in Distinct Patterns, Tetrahedron, vol. 63, 2007, pp. 10657-10670.
Lim et al., "Gadolinium MRI Contrast Agents Based on Triazine Dendrimers: Relaxivity and In Vivo Pharmacokinetcs," American Chemical Society, vol. 23, pp. 2291-2299 (2012).
Search Report and Written Opinion issued in related Singapore Patent Application No. 11201505477T, completed Aug. 10, 2016.
Benita, S. et al., "Characterization of Drug-Loaded Poly(d,l-lactide) Microspheres," Journal of Pharmaceutical Sciences, vol. 73, No. 12, Dec. 1984, pp. 1721-1724.
Berge, et al., "Pharmaceutical Salts," Journal of Pharmaceutical Sciences, vol. 66, No. 1, Jan. 1977, pp. 1-19.
Casini, et al., "Carbonic Anhydrase Inhibitors: Synthesis of Water Soluble Sulfonamides Incorporating a 4-sulfamoylphenylmethylthiourea Scaffold, with Potent Intraocular Pressure Lowering Properties," Journal of Enzyme Inhibition and Medicinal Chemistry, 2002, vol. 17, No. 5, pp. 333-343.
Cecchi et al., Alessandro, "Carbonic Anhydrase Inhibitors. Design of Fluorescent Sulfonamides as Probes of Tumor-assoicated Carbonic Anhydrase IX that Inhibit Isozyme IX-Mediated Acidification of Hypoxic Tumores," Journal of Medicinal Cheimistry, vol. 48, No. 15, Jul. 2005, pp. 4834-4841.
Database Beilstein [Online]; Beilstein Institute for Organic Chemistry, Database Accession No. Citation No. 990210, XP002577062, 3 pages (1958).
De Leval, et al. "Carbonic Anhydrase Inhibitors: Synthesis and Topical Intraocular Pressure Lowering Effects of Fluorine-Containing Inhibitors Devoid of Enhanced Reactivity", Journal of Medicinal Chemistry, 2004, vol. 47, No. 11, pp. 2796-2804.
Dubenko, et al. "Thiocarbanilide Derivatives. IV. Synthesis of unsymmetrical monohalothiocarbanilides", Zhurnal Obshchei Khimii, 1962, vol. 32, pp. 626-628.
Dubois, L., et al., "Imaging the hypoxia surrogate marker CA IX requires expression and catalytic activity for binding fluorescent sulfonamide inhibitors," 2007, Radiotherapy and Oncology, vol. 83, pp. 367-373.
Gallagher, J. et al. "Protease Activity of 1,10-Phenanthroline-Copper(I). Targeted Scission of the Catalytic Site of Carbonic Anhydrase", Biochemistry, 1998, vol. 37, pp. 2096-2104.
Genis et al., Design of a Carbonic Anhydrase IX Active-Site Mimic to Screen Inhibitors for Possible Anti-Cancer Properties, Biochemistry 48(6), pp. 1-20 [pp. 1322-1331], 2009.
Gracheva, et al. "Chemical changes during beta-decay of bismuth-210 (RaE) entering into the composition of tris(p-sulfamoylphenyl)bismuth", STN on the Web, File Caplus, 1968, vol. 83, p. 305.

Greene, T. W. et al., "Protection for the Hydroxyl Group, Including 1,2- and 1,3-Diols," Protective Groups in Organic Synthesis, Third Edition, 1999, pp. 113-148.
Gregoriadis, G., et al., Drug Carriers in Biology and Medicine, Chapter 14: Liposomes, 1979, Academic Press, pp. 287-341.
Hanada et al., "Preparation of 2,8-diazaspiro[4.5]decane containing bis(imidazol-2-ylmethyl_amines as CXCR4 antagonists for treatment of inflammation and immune disease", caplus an 2008:159048, 5 pages.
International Search Report—PCT/US2013/020283—WO2013/103813.
International Search Report and Written Opinion in PCT/US2009/030487 dated Jun. 26, 2009.
International Search Report and Written Opinion in PCT/US2009/066832 dated Oct. 14, 2010.
Jalil, R. et al., "Biodegradable poly(lactic acid) and poly(lactide-co-glycolide) microcapsules: problems associated with preparative techniques and release properties", J. Microencapsulation, 1990, vol. 7, No. 3, pp. 297-325.
Kojima et al., "Synthesis and Characterization of Mononuclear Ruthenium (III) Pyridylamine Complexes and Mechanistic Insights into Their Catalytic Alkane Functionalization with m-Chloroperbenzoic Acid", Chemistry, vol. 13, 2007, pp. 8212-8222.
Kularatne, S.A. et al., "Design, Synthesis, and Preclinical Evaluation of Prostate-Specific Membrane Antigen Targeted 99mTc-Radioimaging Agents," Molecular Pharmaceutics, 2009, vol. 6, No. 3, pp. 790-800.
Kusumi et al., "Preparation of heterocycle compounds having (un)protected acidic group as CXCR4 antagonists", caplus an 2007:1332283, 8 pages.
Lim, et al. "Microencapsulation of Living Cells and Tissues," Journal of Pharmaceutical Sciences, Apr. 1981, vol. 70, No. 4, pp. 351-354.
Liu et al., Preparation and Properties of 99mTc(Co)3—Labeled N,N-Bis(2-pyridylmethyl)-4-aminobutyric Acid, Bioconjug Chem 15(6), pp. 1-14 [pp. 1441-1446], 2004.
Mathiowitz, E. et al., "Morphology of Polyanhydride Miscrosphere Delivery Systems," Scanning Microscopy, 1990, vol. 4, No. 2, pp. 329-340.
Mathiowitz, E. et al., "Polyanhydride Microspheres as Drug Carriers. II. Microencapsulation by Solvent Removal," Journal of Applied Polymer Science, 1988, vol. 35, pp. 755-774.
Nakano, M. et al., "Sustained Urinary Excretion of Sulfamethizole Following Oral Administration of Enteric Coated Microcapsules in Humans," International Journal of Pharmaceutics, 1980, vol. 4, pp. 291-298.
Pastorekov, S., et al., "Carbonic anhydrase IX (CA IX) as potential target for cancer therapy," 2004, Cancer Therapy, vol. 2. (19 pages).
Pomper et al., "Labeled Inhibitors of Prostate Specific Membrane Antigen (psma), Biological Evaluation, and Use as Imaging Agents," Caplus:1755, 2 pages (2009).
Remington's: the Science and Practice of Pharmacy, 17th Edition, p. 1795, 1985.
Saitou et al., "Preparation of N-arylmethyl or N-hererocyclylmethyl-N-(imidazol-2-ymethyl)amines as antagonists of chemokine receptor CXCR4", caplus an 2005:1004718, 6 pages.
Salib, N. et al., "Utilization of Sodium Alginate in Drug Microencapsulation," Pharm. Ind., vol. 40, No. 11a, 1978, pp. 1230-1234.
Sawhney, A. et al., "Bioerodible Hydrogels Based on Photopolymerized Poly(ethylene glycol)-co-poly(a-hydroxy acid) Diacrylate Macromers," Macromolucules, vol. 26, 1993, pp. 581-587.
Shah, et al. "Benzylthioureas, Part III", Journal of Indian Chemical Society, 1959, vol. 36, No. 7, pp. 507-508.
Singh, et al. "The Enzyme-Inhibitor Approach to Cell-Selective Labelling-II. In Vivo Studies with pIBS in Small Animals and Man", Applied Radiation and Isotopes, 1991, vol. 42, No. 3, pp. 261-267.
Steffens MG, et al., Targeting of renal cell carcinoma with iodine-131-labeled chimeric monoclonal antibody G250, 1997, J. Clin. Oncol., 15(4) 1529-37 (1 page abstract).
Thiry et al., "Targeting Tumor-Associated Carbonic Anhydrase IX in Cancer Therapy," Trends in Pharmacological Sciences, vol. 27, No. 11, Nov. 2006, pp. 566-573.

(56) References Cited

OTHER PUBLICATIONS

Thiry, et al. "Indanesulfonamides as Carbonic Anhydrase Inhibitors. Toward Structure-Based Design of Selective Inhibitors of the Tumor-Associated Isozyme CA IX", Journal of Medicinial Chemistry, 2006, vol. 49, No. 9, pp. 2743-2749.
Tweedle et al., "Preparation of substituted 1,4,7-tris(carboxymethyl)-1,4,7,10-tetraazacyclododecane and analogs as metal-chelating ligands useful in diagnostic medicine," Caplus an 1989:173270, 1989, 2 pages.
Vallabhajosula et al., Prostate cancer using PSMA targeted molecular imaging probe, 99mTc-MIP-1404: Phase I clinical study in patients undergoing radcial prostatectomy, Poster, Oct. 16, 2013.
Viswanathan, et al. "Metanilamide-Substituted Thiourea Derivatives", Current Science, 1952, No. 12, pp. 342-343.
Office Action issued in related U.S. Appl. No. 14/517,760, dated Jan. 13, 2017.
Sodee et al., "Synergistic value of single-photon emission computed tomography/computed tomography fusion to radioimmunoscintigraphic imaging of prostate cancer," Semin. Nucl. Med., vol. 37, pp. 17-28 (2007).
Lee et al., 10$^{th}$ International Symposium on the Synthesis and Application of Isotopes and Isotopically Labelled Compounds—Development of PET and SPECT imaging agents, J. labelled Comp. Radiopharm., vol. 53, pp. 398-405 (2010).
Vallabhajosula et al., Novel 99mTc-labeled small molecular inhibitors of prostate specific membrane antigen (PSMA): Initial experience in healthy volunteers and men with metastatic prostate adenocarcinoma (PCa), EJNMMI 38: S202, Abstract No. OP528, 1 page (2011).
Shankar Vallabhajosula, et al., "99m Tc-MIP-1404 SPECT i n Patients Prior to Prostatectomy Prostate cancer using PSMA targeted molecular imaging probe, 99m Tc-MIP-1404: Phase I clinical study in patients undergoing radical prostatectomy", Oct. 16, 2013 (Oct. 16 2013), XP055334031, Retrieved from the Internet: URL:http://files.sharehol der.com/downl oads/PGNX/0x0x697995/171f5de4-799d-4027-a8ff-a cf0e038c8dc/Vailabhajosula_EANM 2013 Poster Oct. 16, 2013. [retrieved on Jan. 11, 2017].
Shankar Vallabhajosula: "PSMA targeted 1-15 SPECT imaging biomarker to detect local and metastat ic prostate cancer (PCa): Phase I studies with 99mTc-MIP-1404", Journal of Nuclear Medicine, May 30, 2013.
Hillier et al., "99mTc-Labeled Small-Molecular Inhibitors of Prostate-specific Membrane Antigen for Molecular Imaging of Prostate Cancer," *The Journal of Nuclear Medicine*, vol. 54, No. 8, pp. 1369-1376 (2013).
Supplemental Search Report issued in European Patent Application No. 14853536, dated Apr. 25, 2017.
Final Office Action issued in co-pending U.S. Appl. No. 14/517,760, dated Nov. 2, 2017.
Notice of Reasons for Rejection issued in related Japanese Patent Application No. 2015-552805, dated Nov. 7, 2017.
Non-Final Office Action issued in co-pending U.S. Appl. No. 15/492,933, dated Jan. 5, 2018.
Notice of Allowance issued in co-pending U.S. Appl. No. 15/492,933, dated Jun. 1, 2018.
Foreign Action other than Search Report on JP 2019-002515 dated Oct. 8, 2019.
Deasy, Patrick et al., "Microencapsulation and Related Drug Processes", 1984, School of Pharmacy, University of Dublin, Marcel Dekker, Inc. (TOC), 5 pages.
Office Action issued in European Patent Application No. 19174044.8, dated Aug. 13, 2020.
Table of Contents to a book entitled "Microencapsulation and Related Drug Processes", 1984, School of Pharmacy, University of Dublin, Marcel Dekker, Inc.[TOC].

* cited by examiner

TRIAZINE BASED RADIOPHARMACEUTICALS AND RADIOIMAGING AGENTS

CROSS-REFERENCE TO RELATED APPLICATIONS

The present application is a continuation of U.S. patent application Ser. No. 16/231,153, filed Dec. 21, 2018, now U.S. Pat. No. 10,898,598, which is a continuation of U.S. patent application Ser. No. 15/233,096, filed on Aug. 10, 2016, now U.S. Pat. No. 10,201,624, which is a divisional of U.S. patent application Ser. No. 14/152,864, filed on Jan. 10, 2014, now U.S. Pat. No. 9,447,121, and which in turn claims the benefit of U.S. Provisional Patent Application Nos. 61/752,350, filed on Jan. 14, 2013, and 61/785,788, filed on Mar. 14, 2013, all of which are incorporated herein by reference in their entirety.

FIELD

The present technology relates generally to the field of radiopharmaceuticals and their use in nuclear medicine as tracers, imaging agents and for the treatment of various disease states.

BACKGROUND

Many tumors express unique proteins that are predictors of malignancy and a poor prognosis. The expression of such proteins on the surface of tumor cells offers a unique opportunity to use such proteins as markers for the diagnoses of a cancer condition, to evaluate the progression of a cancer condition and to use such proteins as targets for the delivery of a radiotherapeutic agent. Radioactive molecules that selectively bind to specific tumor cell surface proteins provide an attractive route for imaging and treating tumors under non-invasive conditions. In particular, the present invention provides radiolabeled ligands that specifically bind the prostate-specific membrane antigen (PSMA) protein, over expressed on many cancer cells, as agents for imaging or radiation based therapy of PSMA-expressing cancer cells.

With over a million men suffering from prostate cancer, it is estimated that the disease will strike one in six U.S. men between the ages of 60 and 80. There are more than 300,000 new cases of prostate cancer diagnosed each year and the mortality from the disease is second only to lung cancer. An estimated $2 billion is currently spent worldwide on surgical, radiation and drugs as treatments for prostate cancer. There is presently no effective therapy for relapsing, metastatic, androgen-independent prostate cancer. New agents that enable rapid visualization of prostate cancer and specific targeting of this cancer tissue for therapeutic purposes are presently needed.

Human prostate-specific membrane antigen (PSMA), also known as folate hydrolase I (FOLH1), is a trans-membrane, 750 amino acid type II glycoprotein which is primarily expressed in the epithelium of normal human prostate tissue, but is upregulated in prostate cancer, including metastatic disease. PSMA is a unique exopeptidase with reactivity toward poly-gamma-glutamated folates, capable of sequentially removing the poly-gamma-glutamyl termini. Since PSMA is expressed by virtually all prostate cancers and its expression is further increased in poorly differentiated, metastatic and hormone-refractory carcinomas, it is a very attractive target for prostate imaging and therapy. Developing ligands that interact with PSMA and carry appropriate radionuclides, therefore, may provide a promising and novel approach for the detection, treatment and management of prostate cancer.

The radio-immunoconjugate form of the anti-PSMA monoclonal antibody (mAb) 7E11, known as the PROSTASCINT scan, is currently being used to diagnose prostate cancer metastasis and recurrence. More recently, monoclonal antibodies that bind to the extracellular domain of PSMA and have a radionuclide were shown to accumulate in PSMA-positive prostate tumor models in animals. However, diagnosis and tumor detection using monoclonal antibodies has been limited by the low permeability of the monoclonal antibody in solid tumor. Tumor detection using low molecular weight radiopharmaceutical compounds, therefore, hold promise and are being explored as potential diagnostic and radiotherapeutic alternatives to radioconjugates of monoclonal antibodies.

The selective targeting of cancer cells with radiopharmaceuticals, either for imaging or therapeutic purposes is challenging. A variety of radionuclides are known to be useful for radio-imaging or cancer radiotherapy, including $^{111}$In, $^{90}$Y, $^{68}$Ga, $^{177}$Lu, $^{99m}$Tc, $^{123}$I and $^{131}$I. Recently it has been shown that some compounds containing a glutamate-urea-glutamate (GUG) or a glutamate-urea-lysine (GUL) recognition element linked to a radionuclide-complex exhibit high affinity for PSMA. Importantly, the present inventors found that the avidity of the GUL-radionuclide conjugate and GUG-radionuclide conjugate depends at least in part on the chemical nature and size of the linker or spacer joining the GUL or GUG group to the radionuclide complex.

The present invention focuses on GUL-radiocomplexes or GUG-radiocomplexes that have a one or more optionally substituted triazene groups as part of a linker conjugating the GUL or GUG groups to the radiocomplex. More specifically, the present invention explores the structure-function activity of such triazine-based linkers, for instance by exploring the relationship between binding affinity and linker length as well as the relationship between binding affinity and the position of the optionally substituted triazine moiety such as a piperazinyl-triazine-p-aminobenzyl group within the linker. Also described are methods for synthesizing the triazine based radiopharmaceuticals, as well as methods for characterization and for using the inventive GUL-radionuclide and GUG-radionuclide conjugates for the diagnosis and treatment of cancer.

SUMMARY

The present invention relates to compounds having a PSMA targeting moiety linked to a radionuclide chelating group as well as radionuclide complexes of the inventive compounds. More specifically, the present technology is focused on the synthesis and use of compounds that conform to the general structure [PSMA recognition motif]-linker-[radionuclide chelating group] and radionuclide complexes of the inventive compounds. As further described below, the inventive compounds and their radionuclide complexes comprise a 1,3,5-triazine moiety within the linker. The incorporation of the 1,3,5-triazine group has advantages since it provides three sites of attachments for the PSMA recognition motif and radionuclide chelating group and also improves the pharmacokinetic properties of the inventive compounds and their radionuclide complexes.

The invention also provides pharmaceutically acceptable formulations of the inventive compounds and their radionuclide complexes. Such formulations are suitable for treating a variety of disease conditions including without limitation prostate cancer, breast cancer, colorectal cancer, brain cancer, lung cancer, liver cancer, endometrial cancer, bone cancer, ovarian cancer, testicular cancer, skin cancer, pancreatic cancer, uterine cancer, cervical cancer, bladder cancer, esophageal cancer, gastric cancer, head and neck cancers, or kidney cancer.

In one embodiment therefore, are provided compounds that conform to Formula I and to stereoisomers, tautomers, prodrugs, and pharmaceutically acceptable salts or esters thereof.

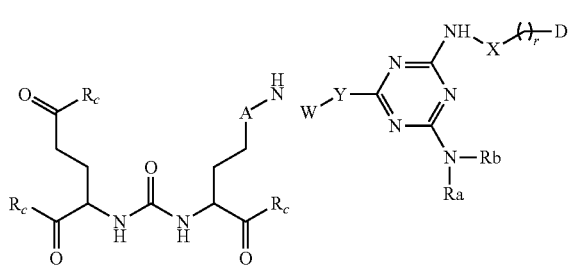

I

In Formula I, A is $(CHR^1)_m$ or $C(O)$ and W is selected from the group consisting of $—C(O)—(CH_2)_p—$; $—C(O)[—CH_2—CH_2—O]_n—$, $—[CH_2—CH_2—O]_n—(CH_2)_2—$, $—C(O)—[CH(R^3)_t]_q—$, $—(CH_2)_m—O—(CH_2)_n—$, $—(CH_2)_m—S—(CH_2)_n—$, $—(CH_2)_m—S(O)—(CH_2)_n—$, $—(CH_2)_m—S(O)_2—(CH_2)_n—$, and $—(CH_2)_m—NR_a(CH_2)_n—$. Substituent Y is selected from $—NH—$, $—NR^2—$, or

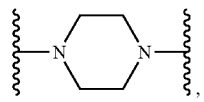 [SMILES: *N1CCN(*)CC1]

while X in Formula I is selected from $—(C_1-C_{10})$alkylene-$(C_3-C_{10})$arylene, $—(C_3-C_{10})$arylene, $—(C_3-C_{10})$arylene-$(C_1-C_{10})$alkylene-, phenylene, $—(C_1-C_{10})$alkylene-$(C_3-C_{10})$cycloalkylene, $—(C_3-C_{10})$cycloalkylene, or $—(C_3-C_{10})$cycloalkylene-$(C_1-C_{10})$alkylene-.

$R^1$ and $R^2$ in Formula I can each independently selected from H, $—(C_1-C_{10})$alkyl, $—C(O)—(C_1-C_{10})$alkyl, benzyl, $—(C_3-C_{10})$cycloalkyl, or $—(C_3-C_{10})$aryl. For Formula I compounds, $R^a$ and $R^b$ are each independently selected from the group consisting of H, $—OH$, $—[CH_2—CH_2—O]_n—(CH_2)_2-T$, $—C(O)—(C_1-C_{10})$alkyl, $—(C_1-C_{10})$alkylene-$C(O)—$, $—(C_1-C_{10})$alkylene-$C(O)—Z$, benzyl, $—(C_3-C_{10})$cycloalkyl, $—(C_3-C_{10})$aryl-$(C_1-C_{10})$alkylene, $—(C_3-C_{10})$aryl, halo-$(C_1-C_{10})$alkyl, hydroxy-$(C_1-C_{10})$alkyl, $—NH—(C_1-C_{10})$alkyl, and $—(C_1-C_{10})$alkylene-$NR^dR^e—$, or $R^a$ and $R^b$ together with the nitrogen to which they are bonded form a $(C_3-C_6)$-heteroaryl or $(C_3-C_6)$-heterocycloalkyl that can further comprise one or more heteroatoms selected from N, S, or O.

Z in Formula I is selected from $—OH$, $—O(C_1-C_{10})$alkyl,

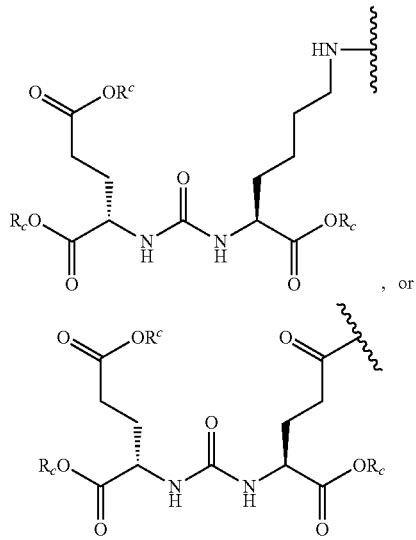

and substituent $R^c$ can be selected from $—OH$, $—O(C_1-C_{10})$alkyl, $—Obenzyl$, $—O(C_3-C_{10})$cycloalkyl, $—O(C_3-C_{10})$aryl, $—O—(C_1-C_{10})$alkylene-$(C_3-C_{10})$aryl, or $—O—(C_1-C_{10})$alkylene-$(C_3-C_{10})$cycloalkyl.

For Formula I compounds, $R^3$ is selected from H, halogen, $—OH$, $—NH_2$, $—(CH_2)_p—COOH$, or $—(CH_2)_p—NH_2$, substituent T is selected from $—H$, $—OH$, $—COOH$, or $—NR^dR^e$ and $R^d$ and $R^e$ are each independently selected from H, bond, $—OH$, $—(C_1-C_{10})$alkyl, or $—(C_3-C_{10})$heteroaryl-$(C_1-C_{10})$alkylene. Subscripts m, n, p, q, t and r in Formula I are each independently 0, 1, 2, 3, 4, 5, 6, 7, 8 9, or 10; and group D is selected from

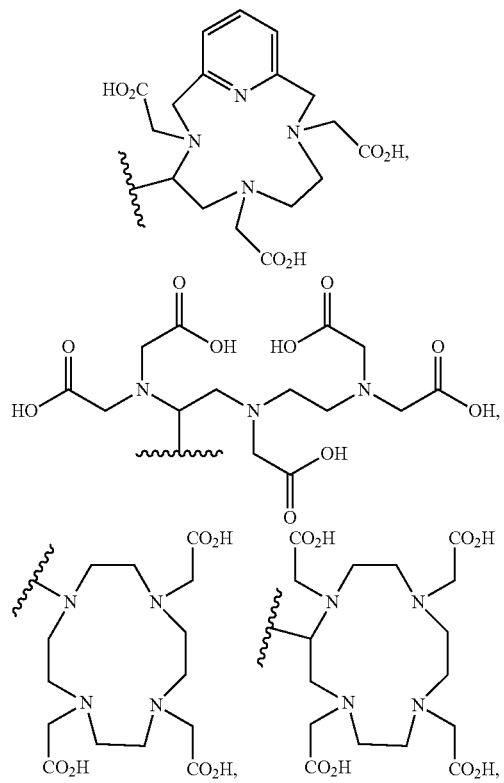

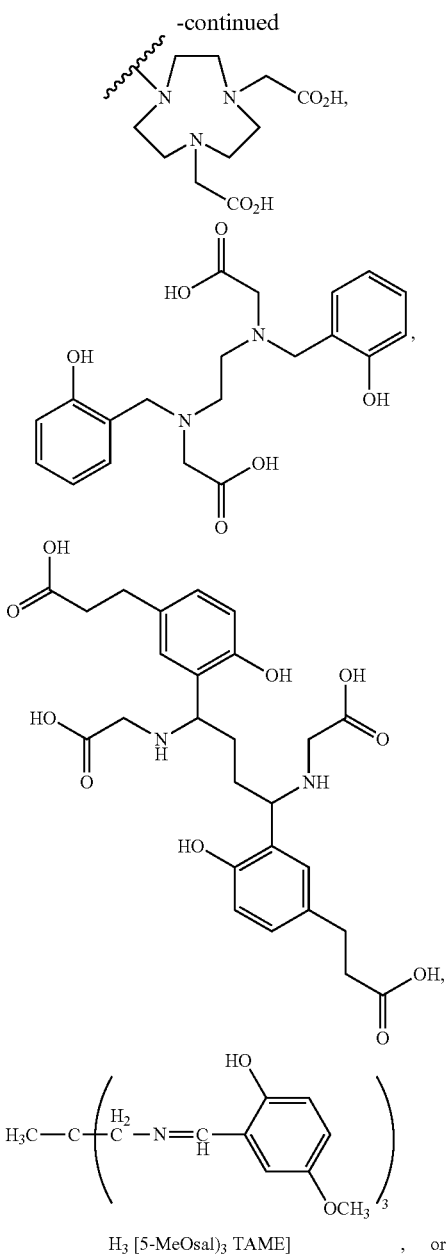

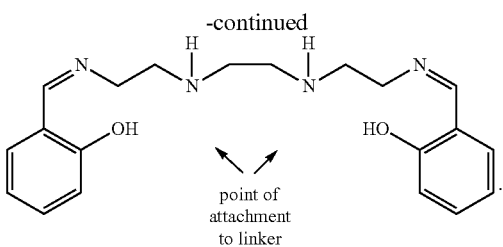

point of attachment to linker

Any alkyl, alkylene, aryl, arylene, heteroaryl, heteroarylene, cycloalkyl, cycloalkylene, heterocycloalkyl, or heterocycloalkylene in Formula I is optionally substituted with 1, 2, or 3 substituent groups selected from the group consisting of —($C_1$-$C_{10}$)alkyl, —($C_1$-$C_{10}$)haloalkyl, —($C_1$-$C_{10}$) aminoalkyl, —($C_1$-$C_{10}$)alkylene-COOH, —($C_1$-$C_{10}$) hydroxyalkyl, —OH, halogen, —$NH_2$, —COOH, —C(O)—($C_1$-$C_{10}$)alkyl, —($C_1$-$C_{10}$)alkylene-C(O)—, —($C_1$-$C_{10}$) alkylene-C(O)—X, —NH—($C_1$-$C_{10}$)alkyl, and —($C_1$-$C_{10}$) alkylene-$NR^dR^e$—, and —$NR^dR^e$. Pursuant to these definitions, for certain Formula I compounds, X is phenylene, r is 1 and D is

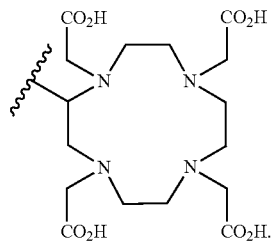

The present invention also provides compounds that conform to Formula II, to stereoisomers, tautomers, prodrugs, and pharmaceutically acceptable salts or esters thereof, and to their pharmaceutically acceptable formulations as therapeutics for treating various disease states associated uncontrolled proliferation of cells.

II

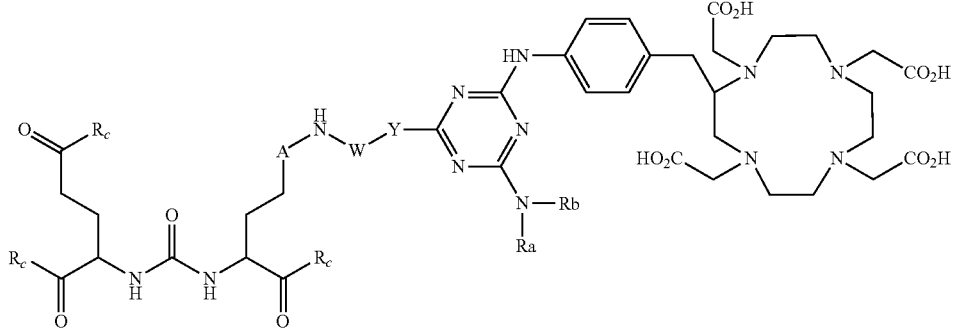

In Formula II, A is $(CHR^1)_m$ or $C(O)$ and substituent W is selected from the group consisting of $—C(O)—(CH_2)_p—$; $—C(O)[—CH_2—CH_2—O]_n—$, $—[CH_2—CH_2—O]_n—(CH_2)_2—$, $—C(O)—[CH(R^3)_t]_q—$, $—(CH_2)_m—O—(CH_2)_n—$, $—(CH_2)_m—S—(CH_2)_n—$, $—(CH_2)_m—S(O)—(CH_2)_n—$, $—(CH_2)_m—S(O)_2—(CH_2)_n—$, and $—(CH_2)_m—NR_a—(CH_2)_n—$.

Group Y in Formula II is selected from $—NH—$, $—NR^2—$,

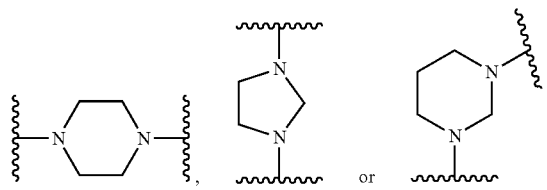

while variables $R^1$ and $R^2$ are each independently selected from H, $—C(O)—(C_1-C_{10})$alkyl, benzyl, $—(C_3-C_{10})$cycloalkyl, or $—(C_3-C_{10})$aryl.

In Formula II, $R^a$ and $R^b$ are each independently selected from the group consisting of H, $—OH$, $—(C_1-C_{10})$alkyl, $—[CH_2—CH_2—O]_n—(CH_2)_2-T$, $—C(O)—(C_1-C_{10})$alkyl, $—(C_1-C_{10})$alkylene-C(O)—, $—(C_1-C_{10})$alkylene-C(O)—Z, benzyl, $—(C_3-C_{10})$cycloalkyl, $—(C_3-C_{10})$aryl-$(C_1-C_{10})$alkylene, $—(C_3-C_{10})$aryl, hydroxy-$(C_1-C_{10})$alkyl, $—NH—(C_1-C_{10})$alkyl, and $—(C_1-C_{10})$alkylene-$NR^dR^e—$. Alternatively, $R^a$ and $R^b$ together with the nitrogen to which they are bonded form a $(C_3-C_6)$-heteroaryl or $(C_3-C_6)$-heterocycloalkyl that can further comprise one or more heteroatoms selected from N, S, or O.

Z in Formula II is selected from $—OH$, $—O(C_1-C_{10})$alkyl,

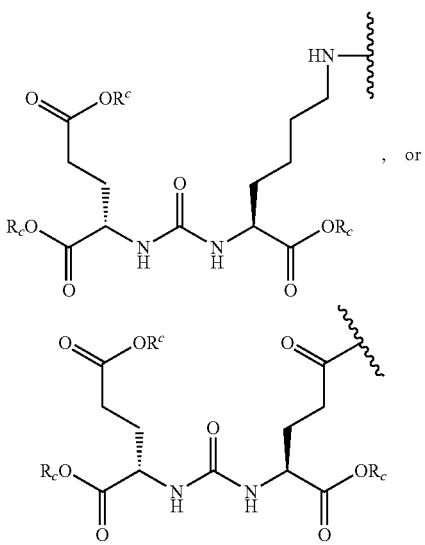

and substituent $R^c$ is selected from $—OH$, $—O(C_1-C_{10})$alkyl, $—Obenzyl$, $—O(C_3-C_{10})$cycloalkyl, $—O(C_3-C_{10})$aryl, $—O—(C_1-C_{10})$alkylene-$(C_3-C_{10})$aryl, or $—O—(C_1-C_{10})$alkylene-$(C_3-C_{10})$cycloalkyl.

For Formula II compounds $R^3$ is selected from H, halogen, $—OH$, $—NH_2$, $—(CH_2)_p—COOH$, or $—(CH_2)_p—NH_2$, T is selected from $—H$, $—OH$, $—COOH$, or $—NR^dR^e$ and each of $R^d$ and $R^e$ are independently selected from H, bond, $—OH$, $—(C_1-C_{10})$alkyl, or $—(C_3-C_{10})$heteroaryl-$(C_1-C_{10})$alkylene.

Any alkyl, alkylene, aryl, arylene, heteroaryl, heteroarylene, cycloalkyl, cycloalkylene, heterocycloalkyl, or heterocycloalkylene in Formula II can be optionally substituted with 1, 2, or 3 substituent groups selected from the group consisting of $—(C_1-C_{10})$alkyl, $—(C_1-C_{10})$haloalkyl, $—(C_1-C_{10})$ aminoalkyl, $—(C_1-C_{10})$alkylene-COOH, $—(C_1-C_{10})$hydroxyalkyl, $—NH_2$, $—COOH$, $—C(O)—(C_1-C_{10})$alkyl, $—(C_1-C_{10})$alkylene-C(O)—, $—(C_1-C_{10})$alkylene-C(O)—X, $—NH—(C_1-C_{10})$alkyl, and $—(C_1-C_{10})$alkylene-$NR^dR^e—$, and $—NR^dR^e$ and subscripts m, n, p, q, t and x are each independently 0, 1, 2, 3, 4, 5, 6, 7, 8 9, or 10;

For certain Formula II compounds A is $(CH_2)_m$, W is $—C(O)—(CH_2)_p—$ and Y is $—NH—$ or

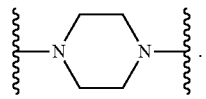

In one embodiment, A is $(CH_2)_2$, W is $—C(O)—(CH_2)_7—$ or $—C(O)—(CH_2)_{10}—$ and Y is

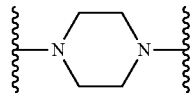

with $R^a$ and $R^b$ each independently being hydrogen or methyl and substituent $R^c$ is $—OH$.

In one embodiment, $R^a$ and $R^b$ together with the nitrogen to which they are bonded form a $(C_3-C_6)$-heterocycloalkyl, for example, a group selected from piperidine, piperazine, morpholine, thiomorpholine, isothiazolidine, isoxazolidine, pyrrolidine, immidazolidine, thiazolidine, oxazolidine, or 4-(piperidin-4-yl)butanoic acid.

For certain other Formula II compounds, $R^a$ is $—H$ and $R^b$ is

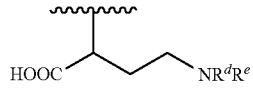

with groups $R^d$ and $R^e$ each independently being a $—(C_3-C_{10})$heteroaryl-$(C_1-C_{10})$alkylene, such as

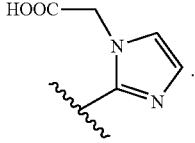

Also encompassed by the present technology are metal complexes comprising a radionuclide and a compound according to Formula I or Formula II. The radionuclide used is selected from the group consisting of $^{111}$In, $^{90}$Y, $^{68}$Ga, $^{64}$Cu, $^{153}$Gd, $^{155}$Gd, $^{157}$Gd, $^{59}$Fe, $^{225}$Ac, $^{212}$Bi, $^{213}$Bi, $^{55}$Co, $^{67}$Cu, $^{165}$Dy, $^{166}$Ho, $^{192}$Ir, $^{223}$Ra, $^{186}$Re, $^{188}$Re, $^{105}$Rh, $^{212}$Pb, $^{213}$Pb, $^{149}$Tb, $^{227}$Th, $^{153}$Sm, $^{89}$Sr, $^{117m}$Sn, $^{169}$Yb, $^{90}$Y, $^{86}$Y, $^{89}$Zr and $^{177}$Lu.

The present invention also provides a pharmaceutically acceptable salt, stereoisomer, tautomer, or prodrug of a Formula I or a Formula II compound as well as the radionuclide complexes of Formula I or Formula II compounds.

Radionuclide complexes of Formula I or II compounds and their pharmaceutical formulations are useful for obtaining radiographic images or for treating a number of diseases and conditions, including but not limited to prostate cancer, breast cancer, colon cancer, brain cancer, lung cancer, liver cancer, endometrial cancer, bone cancer, ovarian cancer, or kidney cancer.

In one embodiment, the invention provides a method of obtaining a radiographic image of one or more tissues that express prostate-specific membrane antigen (PSMA) by (a) contacting one or more tissues that express PSMA with a metal complex comprising a radionuclide and a compound according to Formula III

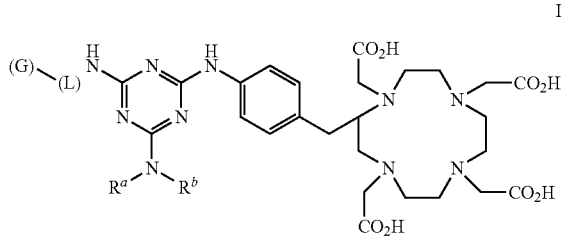

III or a pharmaceutically acceptable salt or solvate thereof; and (b) recording a radiographic image of the one or more tissues.

Pursuant to this methodology, variable G in Formula III is

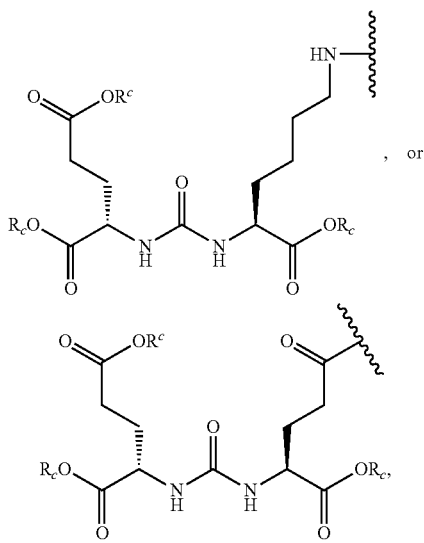

L is selected from —NH—$(C_1-C_{10})$alkylene-, —NH—$(C_1-C_{10})$alkylene-C(O)—, —C(O)—$(C_1-C_{10})$alkylene-, —C(O)—$(C_1-C_{10})$alkylene-C(O)— or

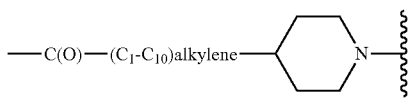

and $R^a$ and $R^b$ are each independently selected from the group consisting of H, —OH, —$(C_1-C_{10})$alkyl, —[$CH_2$—$CH_2$—$O]_n$—$(CH_2)_2$-T, —C(O)—$(C_1-C_{10})$alkyl, —$(C_1-C_{10})$alkylene-C(O)—, —$(C_1-C_{10})$alkylene-C(O)—Z, benzyl, —$(C_3-C_{10})$cycloalkyl, —$(C_3-C_{10})$aryl-$(C_1-C_{10})$alkylene, —$(C_3-C_{10})$aryl, halo-$(C_1-C_{10})$alkyl, hydroxy-$(C_1-C_{10})$alkyl, —NH—$(C_1-C_{10})$alkyl, and —$(C_1-C_{10})$alkylene-NR$^a$R$^e$—.

For certain Formula III compounds $R^a$ and $R^b$ together with the nitrogen to which they are bonded form a $(C_3-C_6)$-heteroaryl or $(C_3-C_6)$-heterocycloalkyl that can further comprise one or more heteroatoms selected from N, S, or O.

Substituent Z in Formula III is selected from —OH, —$O(C_1-C_{10})$alkyl,

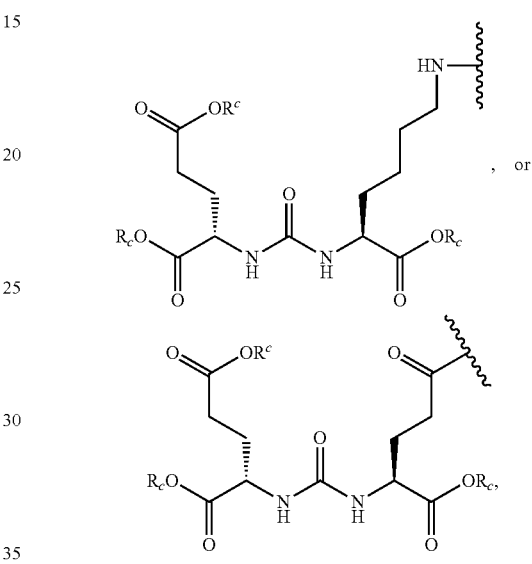

substituents $R^d$ and $R^e$ are each independently selected from H, bond, —OH, —$(C_1-C_{10})$alkyl, or —$(C_3-C_{10})$heteroaryl-$(C_1-C_{10})$alkylene and subscript n is an integer selected from 0, 1, 2, 3, 4, 5, 6, 7, 8 9, or 10.

Pursuant to one embodiment, as noted above, the invention provides a radionuclide complex of Formula I or Formula II compounds as therapeutics for treating a subject diagnosed with cancer for instance prostate cancer. Treatment according to the inventive methodology is effected by administering to a subject a therapeutically effective amount of a prostate-specific membrane antigen (PSMA) binding complex comprising a triazinylene linker and capable of being retained in a PSMA-expressing tumor tissue for a longer interval of time than non-PSMA expressing tissue.

DETAILED DESCRIPTION

Figure 1:
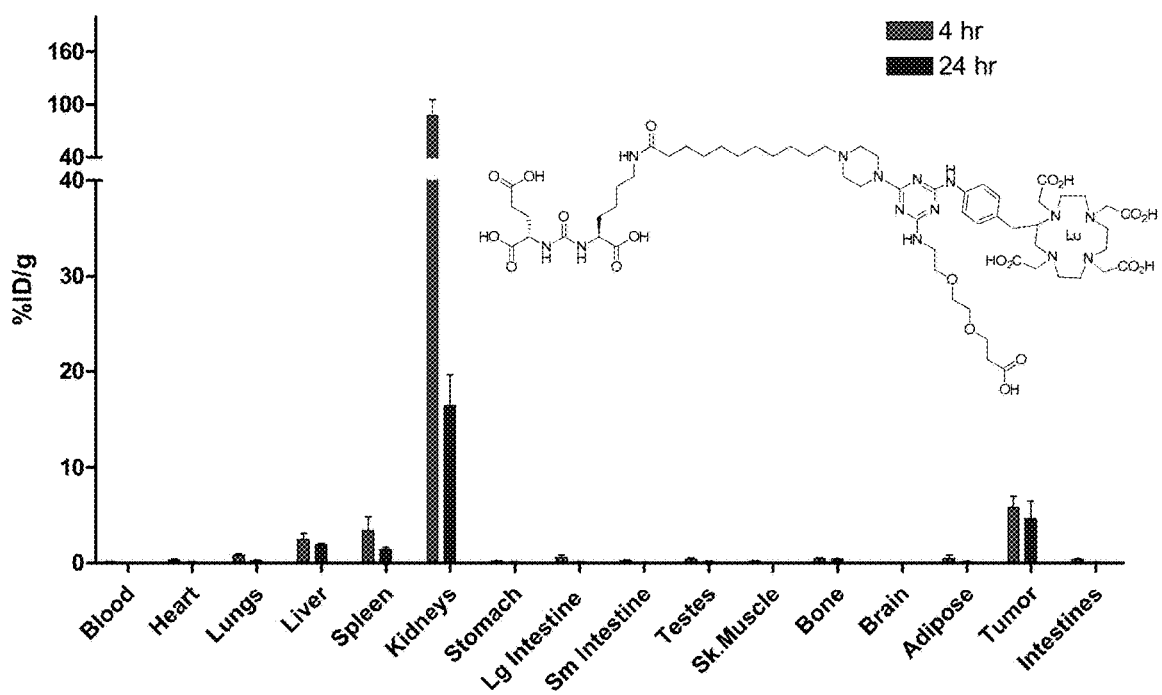
FIG. 1 illustrates tissue biodistribution of the $^{177}$Lu-complex of (2S)-2-(3-(1-carboxy-5-(11-(4-(4-((2-(2-(2-carboxyethoxy)ethoxy)ethyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid according to the present invention in LNCap Xenograft mice.

There are two categories of radiopharmaceuticals: (i) those with biological distribution determined strictly by blood flow, or perfusion, and targeting high capacity systems such as glomerular filtration, phagocytosis, hepatocyte clearance and bone absorption and (ii) those with distribution determined by specific enzymatic or receptor binding interactions, which are low-capacity sites. The radiopharmaceuticals according to Formula I or Formula II belong to the second category and are synthesized by conjugating the radionuclide coordination complex to a biologically active molecule selective for PSMA protein using a linker that has a triazine moiety.

The terms "linker," "spacer," "linker group" or "spacer group" are used interchangeably in this document and refer to a group that spans the distance between two other identified groups, or which "spaces" them apart. The linker or spacer may be a bond, an organic group, or an inorganic group or atom.

In some embodiments, the linker or spacer is an optionally substituted $(C_1-C_{15})$alkylene, a $(C_2-C_{15})$alkenylene, a $(C_2-C_{15})$alkynylene group, a —C(O)—$(C_1-C_{15})$alkylene-, a —C(O)—$(C_3-C_{15})$arylene-$(C_1-C_{15})$alkylene-, —W—Y—$(C_3-C_{15})$heteroarylene-NH—X—$(CH_2)_r$—, or a —C(O)—$(C_1-C_{15})$alkylene-Y—$(C_3-C_{15})$heteroarylene-NH—X—, where the variables "W", "X" and "Y" are further described below. Illustrative substituent groups include without limitation carboxyl groups, carboxylate, hydroxyl groups, and amino $(NR^aR^b)$ groups. For certain embodiments, the $(C_1-C_{15})$alkylene group in the linker described above can be replaced by a $(C_1-C_{15})$polyol, for example, a polyethylene glycol (PEG) moiety. Exemplary linker or spacer groups are illustrated without limitation throughout the specification and working examples.

For convenience, certain terms employed herein and within the appended claims are defined here.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The use of the terms "a" and "an" and "the" and similar referents in the context of describing the elements (especially in the context of the following claims) are to be construed to cover both the singular and the plural, unless otherwise indicated herein or clearly contradicted by context.

The terms "lipophilic group" and "lipophilic moiety" as used herein refer to a group, moiety or substituent that has a greater affinity for non-polar or non-aqueous environments versus polar or aqueous environments. For example, Merriam Webster's online dictionary defines "lipophilic" as "having an affinity for lipids (as fats)." Illustrative lipophilic moieties include aliphatic hydrocarbon radicals, e.g., alkyl radicals, aromatic hydrocarbon radicals, and long-chain acyl radicals; all of them have increasing lipophilicity as the number of constituent carbons increases. In general, addition of a lipophilic moiety to a particular compound will increase the compound's affinity for octanol in the standard octanol/water partition-coefficient-determination protocol; this protocol may be used to gauge a compound's relative hydrophobicity (lipophilicity) and hydrophilicity.

The term "ligand" refers to a species that interacts in some fashion with another species. In one example, a ligand may be a Lewis base that is capable of forming a coordinate bond with a Lewis Acid. In other examples, a ligand is a species, often organic, that forms a coordination complex with a metal ion. In biochemistry and pharmacology, a ligand is a substance (usually a small molecule), that forms a complex with a biomolecule to serve a biological purpose. In a narrower sense, a ligand is a signal triggering molecule, binding to a site on a target protein. The binding occurs by intermolecular forces, such as ionic bonds, hydrogen bonds and van der Waals forces.

The term "chelating agent" refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" are art-recognized and refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term "coordination" refers to an interaction in which one multi-electron pair donor coordinatively bonds (is "coordinated") to one metal ion.

The term radionuclide refers to an atom with an unstable nucleus, which is a nucleus characterized by excess energy available to be imparted either to a newly created radiation particle within the nucleus or to an atomic electron. The radionuclide can undergo radioactive decay and in the process emit subatomic ionizing particles. Illustrative of subatomic ionizing particles without limitation are alpha (a) particles, beta ((3) particle and gamma (γ) rays. Exemplary radionuclides include without limitation elements belonging to the lanthanide series, actinide series as well as radioisotpes of transition metals. Illustrative radionuclides may include, but are not limited to $^{111}$In, $^{90}$Y, $^{68}$Ga, $^{64}$Cu, $^{153}$Gd, $^{155}$Gd, $^{157}$Gd, $^{59}$Fe, $^{225}$Ac, $^{212}$Bi, $^{213}$Bi, $^{55}$Co, $^{67}$Cu, $^{165}$Dy, $^{166}$Ho, $^{192}$Ir, $^{223}$Ra, $^{186}$Re, $^{188}$Re, $^{105}$Rh, $^{212}$Pb, $^{213}$Pb, $^{149}$Tb, $^{227}$Th, $^{153}$Sm, $^{89}$Sr, $^{117m}$Sn, $^{169}$Yb, $^{90}$Y, $^{86}$Y, $^{89}$Zr and $^{177}$Lu. However, the term is not limited to these four radionuclides.

Fmoc is an abbreviation for the chemical group: fluorenylmethyloxycarbonyl.

The phrases "effective amount" or "therapeutically-effective amount" as used herein means that amount of a compound, material, or composition comprising a compound of the invention, or other active ingredient which is effective for producing some desired therapeutic effect in at least a sub-population of cells in an animal at a reasonable benefit/risk ratio applicable to any medical treatment. A therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

As used herein, the terms "treating" or "treatment" is intended to encompass also diagnosis, prophylaxis, therapy and cure. The patient receiving this treatment is any animal in need, including primates, in particular humans, and other mammals such as equines, cattle, swine and sheep; and poultry and pets in general.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (S) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

A "patient" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug that is a compound which upon administration to a patient, must undergo chemical conversion by metabolic processes before becoming an active pharmacological agent. Illustrative prodrugs of compounds in accordance with Formula I are esters, preferably alkyl esters or fatty acid esters.

The term "heteroatom" refers to an atom of any element other than carbon or hydrogen. Illustrative heteroatoms include boron, nitrogen, oxygen, phosphorus, sulfur and selenium.

In general, "substituted" refers to an alkyl, alkylene, alkenyl, alkenylene, alkyne, alkynylene, aryl, arylene, cycloalkyl, or cycloalkylene group, as defined below in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN), haloalkyl, aminoalkyl, hydroxyalkyl, cycloalkyl and the like.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The terms "alkylene" and "substituted alkylene" refer to divalent alkyl and divalent substituted alkyl, respectively. Examples of alkylene include without limitation, ethylene (—$CH_2$—$CH_2$—). "Optionally substituted alkylene" refers to alkylene or substituted alkylene.

The term "alkylcarbonyl" or "alkylenecarbonyl" denote a —($C_1$-$C_8$)alkyl-C(O)— or —C(O)—($C_1$-$C_8$)alkyl- groups in which at least one of the methylenes in the $C_1$-$C_8$ alkyl group is replaced with a C(O) group. Representative examples include, but are not limited to, acetyl, propionyl, and $CH_3(CH_2)_2C(O)$— group, or —$CH_2(CH_2)_2C(O)$—.

The terms "cyclic alkyl" or "cycloalkyl" refers to a saturated or partially saturated non-aromatic cyclic alkyl groups of from 3 to 14 carbon atoms and no ring heteroatoms and having a single ring or multiple rings including fused and bridged ring systems. Cycloalkyl groups may be substituted or unsubstituted. Cycloalkyl or cyclic alkyl groups include mono-, bi- or tricyclic alkyl groups having from 3 to 14 carbon atoms in the ring(s), or, in some embodiments, 3 to 12, 3 to 10, 3 to 8, or 3 to 4, 5, 6 or 7 carbon atoms. Illustrative monocyclic cycloalkyl groups include, but not limited to, cyclopropyl, cyclobutyl, cyclopentyl, cyclohexyl, cycloheptyl, and cyclooctyl groups. Bi- and tricyclic ring systems include both bridged cycloalkyl groups and fused rings, such as, but not limited to, bicyclo[2.1.1]hexane, adamantyl, decalinyl, and the like.

A "cycloalkylene" is a divalent saturated or partially saturated non-aromatic cyclo alkyl groups having 3 to 14 carbon atoms and no ring heteroatoms.

Alkenyl groups include straight and branched chain and cycloalkyl groups as defined above, except that at least one double bond exists between two carbon atoms. Thus, alkenyl groups have from 2 to about 12 carbon atoms in some embodiments, from 2 to 10 carbon atoms in other embodiments, and from 2 to 8 carbon atoms in other embodiments. Examples include, but are not limited to, vinyl, allyl, —CH═CH($CH_3$), —CH═C($CH_3$)$_2$, —C($CH_3$)═$CH_2$, —C($CH_3$)═CH($CH_3$), —C($CH_2CH_3$)═$CH_2$, cyclohexenyl, cyclopentenyl, cyclohexadienyl, butadienyl, pentadienyl, and hexadienyl, among others. Alkenyl groups may be substituted or unsubstituted. Representative substituted alkenyl groups may be mono-substituted or substituted more than once, such as, but not limited to, mono-, di- or tri-substituted with substituents such as those listed above.

The term "alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne" or "alkynyl" refers to straight and branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkynylene" refers to divalent alkyne. Examples of alkynylene include without limitation, ethynylene, propynylene. "Substituted alkynylene" refers to divalent substituted alkyne.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 3 to 12 or even 3-10 carbon atoms in the ring portions of the groups. Aryl group includes both substituted and unsubstituted aryl groups. Substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituent groups such as those listed above.

"Arylene" denotes divalent aryl, and "substituted arylene" refers to divalent substituted aryl. "Optionally substituted arylene" refers to arylene or substituted arylene. Illustrative of the arylene group is phenylene.

"Heterocycloalkyl" means a saturated or unsaturated non-aromatic monocyclic, bicyclic, tricyclic or polycyclic ring system that has from 5 to 14 atoms in which from 1 to 3 carbon atoms in the ring are replaced by heteroatoms of 0, S or N. A heterocycloalkyl is optionally fused with benzo or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl.

"Optionally substituted heterocycloalkyl" denotes heterocycloalkyl that is substituted with 1 to 3 substituents, e.g., 1, 2 or 3 substituents, attached at any available atom to produce a stable compound, wherein the substituents are as described herein.

The term "cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or heteroaryl ring as defined above. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below.

The term "cycloalkylene" refers to divalent cycloalkyl. The term "optionally substituted cycloalkylene" refers to cycloalkylene that is substituted with 1 to 3 substituents, e.g., 1, 2 or 3 substituents, attached at any available atom to produce a stable compound, wherein the substituents are as described herein.

The term "$(C_3-C_{14})$aryl-$(C_1-C_6)$alkylene" refers to a divalent alkylene wherein one or more hydrogen atoms in the $C_1-C_6$ alkylene group is replaced by a $(C_3-C_{14})$aryl group. Examples of $(C_3-C_{14})$aryl-$(C_1-C_6)$alkylene groups include without limitation 1-phenylbutylene, phenyl-2-butylene, 1-phenyl-2-methylpropylene, phenylmethylene, phenylpropylene, and naphthylethylene.

The term "$(C_1-C_{10})$alkylene-$(C_3-C_{14})$arylene" refers to a divalent arylene in which one or more hydrogen atoms in the $C_3-C_{14}$ arylene is replaced by a $(C_1-C_{10})$alkyl group and wherein one of the hydrogens of the alkyl group is replaced by another group. Examples of "$(C_1-C_{10})$alkylene-$(C_3-C_{14})$arylene groups include without limitation butylene-4-phenylene, propylene-2-phenylene, and 1-[2-methylpropylene]phenylene.

The term "$(C_3-C_{14})$arylene-$(C_1-C_{10})$alkylene" refers to a divalent alkylene in which one or more hydrogen atoms in the $C_1-C_{10}$ alkylene is replaced by a divalent $(C_3-C_{14})$ arylene group. Exemplary of "$(C_3-C_{14})$arylene-$(C_1-C_{10})$alkylene group include without limitation phenylene-4-butylene, phenylene-2-butylene, and phenylene-1-[2-methylpropylene].

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms.

"Heterocyclyl" or heterocycloalkyl refers to non-aromatic ring compounds containing 3 or more ring members, of which one or more ring carbon atoms are replaced with a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Heterocyclyl groups may be substituted or unsubstituted. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more ring carbon atoms are replaced with heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

The term "alkoxy" refers to an —O-alkyl group having the indicated number of carbon atoms. For example, a $(C_1-C_{10})$alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O— neopentyl (neopentoxy), —O-hexyl (hexyloxy), —O-isohexyl (isohexyloxy), and —O-neohexyl (neohexyloxy). Examples of cycloalkoxy groups include but are not limited to cyclopropyloxy, cyclobutyloxy, cyclopentyloxy, cyclohexyloxy, and the like. Alkoxy groups may be substituted or unsubstituted.

The term "carbocycle" refers to an aromatic or non-aromatic ring in which each atom of the ring is carbon.

The term "nitro" refers to —NO$_2$.

The term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "Advanced Inorganic Chemistry" by Cotton and Wilkinson.

The term "amine or amino" refers to an —NR$^d$R$^e$ group wherein R$^d$ and R$^e$ each independently refer to a hydrogen, (C$_1$-C$_8$)alkyl, aryl, heteroaryl, and heterocycloalkyl group. When R$^d$ and R$^e$ are attached to the same nitrogen atom, they can be combined with the nitrogen atom to form a 5-, 6-, or 7-membered ring. For example, —NR$^d$R$^e$ is meant to include 1-pyrrolidinyl, pyridinyl or a 4-morpholinyl ring.

The term "amido" is art recognized as an amino-substituted carbonyl and includes a moiety that may be represented by the general formula, —C(O)NR$^d$R$^e$ group wherein R$^d$ and R$^e$ are as defined above.

The term 'nitrile or cyano" can be used interchangeably and refer to a —CN group which is bound to a carbon atom of a heteroaryl ring, aryl ring and a heterocycloalkyl ring.

The term "aminoalkyl," refers to an (C$_1$-C$_{10}$)alkyl group wherein one or more hydrogen atoms in the (C$_1$-C$_{10}$)alkyl group is replaced with a —NR$^d$R$^e$ group, where R$^d$ and R$^e$ can be the same or different, for example, R$^d$ and R$^e$ each independently refer to a hydrogen, (C$_1$-C$_8$)alkyl, aryl, heteroaryl, heterocycloalkyl, (C$_1$-C$_8$)haloalkyl, and (C$_1$-C$_{10}$) hydroxyalkyl group. Examples of aminoalkyl groups include, but are not limited to, aminomethyl, aminoethyl, 4-aminobutyl and 3-aminobutylyl.

The term "haloalkoxy," refers to an —O—(C$_1$-C$_8$)alkyl group wherein one or more hydrogen atoms in the C$_1$-C$_8$ alkyl group is replaced with a halogen atom, which can be the same or different. Examples of haloalkyl groups include, but are not limited to, difluoromethocy, trifluoromethoxy, 2,2,2-trifluoroethoxy, 4-chlorobutoxy, 3-bromopropyloxy, pentachloroethoxy, and 1,1,1-trifluoro-2-bromo-2-chloroethoxy.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

A "hydroxyl" or "hydroxy" refers to an —OH group.

The terms "carboxyl" and "carboxylate" include such moieties as may be represented by the general formulas:

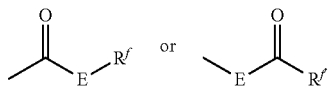

wherein E is a bond or represents O or S, and R$^f$ and R$^{f'}$ individually is H, alkyl, alkenyl, aryl, or a pharmaceutically acceptable salt. Where E is O, and R$^f$ is as defined above, the moiety is referred to herein as a carboxyl group, and particularly when R$^f$ is a hydrogen, the formula represents a "carboxylic acid". In general, where the expressly shown oxygen is replaced by sulfur, the formula represents a "thiocarbonyl" group.

The substituent —CO$_2$H, may be replaced with bioisosteric replacements such as:

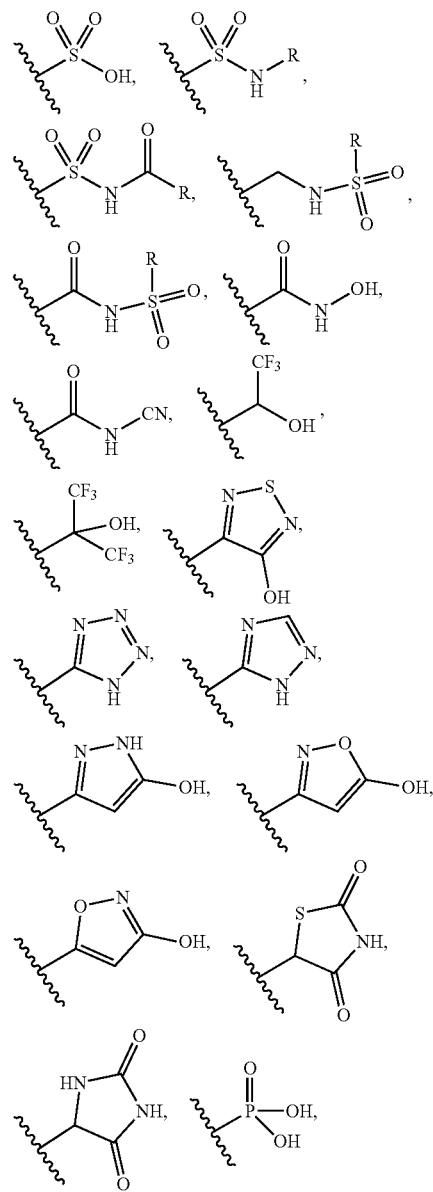

and the like, wherein R has the same definition as R' and R" as defined herein. See, e.g., THE PRACTICE OF MEDICINAL CHEMISTRY (Academic Press: New York, 1996), at page 203.

The terms "alkoxyl" or "alkoxy" refer to an alkyl group, as defined above, having an oxygen radical attached thereto. Representative alkoxyl groups include methoxy, ethoxy, propoxy, butyoxy, tert-butoxy and the like. An "ether" is two hydrocarbons covalently linked by an oxygen. "Ether" also encompasses polyethers where more than one ether group, or linkage, may be present in a given group. "Ether" also encompasses cyclic ethers, and crown ethers, where the ether linkage is within a cyclic group.

The term "(C$_5$-C$_{14}$)aryl-(C$_1$-C$_{10}$)alkylene" refers to a divalent alkylene wherein one or more hydrogen atoms in the C$_1$-C$_{10}$ alkylene group is replaced by a (C$_3$-C$_{14}$)aryl group. Examples of (C$_3$-C$_{14}$)aryl-(C$_1$-C$_{10}$)alkylene groups include without limitation 1-phenylbutylene, phenyl-2-butylene, 1-phenyl-2-methylpropylene, phenylmethylene, phenylpropylene, and naphthylethylene.

The term "($C_5$-$C_{14}$)heteroaryl-($C_1$-$C_{10}$)alkylene" refers to a divalent alkylene wherein one or more hydrogen atoms in the $C_1$-$C_{10}$ alkylene group is replaced a ($C_3$-$C_{14}$)heteroaryl group. Examples of ($C_3$-$C_{14}$)heteroaryl-($C_1$-$C_{10}$)alkylene groups include without limitation 1-pyridylbutylene, quinolinyl-2-butylene and 1-pyridyl-2-methylpropylene.

The term "—($C_5$-$C_{14}$)heteroarylene-($C_1$-$C_{10}$)alkylene-" refers to a divalent alkylene wherein one or more hydrogen atoms in the $C_1$-$C_{10}$ alkylene group is replaced a ($C_3$-$C_{14}$) heteroaryl group and wherein one of the hydrogens or one of the heteroatoms of the ($C_3$-$C_{14}$)heteroaryl group is bonded to another group, for example, a ($C_1$-$C_{10}$)alkyl group.

A "benzyl" is

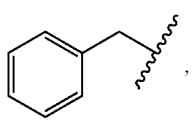 [SMILES: *Cc1ccccc1]

while the term "benzylene" denotes a divalent benzyl moiety that is represented by the following structure

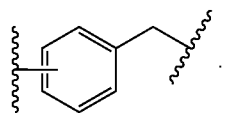

A halogen refers to chlorine, bromine, fluorine, or iodine.

The definition of each expression, e.g. alkyl, m, n, and the like, when it occurs more than once in any structure, is intended to be independent of its definition elsewhere in the same structure.

The terms triflyl, tosyl, mesyl, and nonaflyl refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain the groups, respectively. The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in the compositions may exist in particular geometric or stereoisomeric forms. In addition, compounds may also be optically active. The compounds may also include cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. If, for instance, a particular enantiomer of compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 3$^{rd}$ ed.; Wiley: New York, 1999).

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

As described above, the present invention relates to compounds according to Formula I.

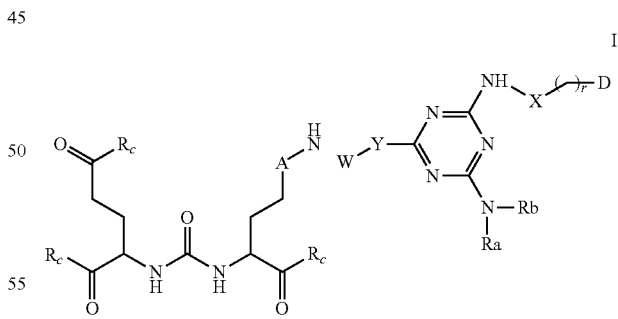

I

For Formula I compounds variable A is $(CHR^1)_m$ or $C(O)$ and W is selected from the group consisting of —C(O)—$(CH_2)_p$—; —C(O)[—$CH_2$—$CH_2$—O]$_n$—, —[$CH_2$—$CH_2$—O]$_n$—$(CH_2)_2$—, —C(O)—[$CH(R^3)_t$]$_q$, —$(CH_2)_m$—O—$(CH_2)_n$—, —$(CH_2)_m$—S—$(CH_2)_n$—, —$(CH_2)_m$—S(O)—$(CH_2)_n$—, —$(CH_2)_m$—S(O)$_2$—$(CH_2)_n$—, and —$(CH_2)_m$—NR$_a$—$(CH_2)_n$—.

Variable Y in Formula I is selected from —NH—, —NR$^2$—, or

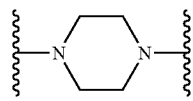

and X is group selected from —(C$_1$-C$_{10}$)alkylene-(C$_3$-C$_{10}$)arylene, —(C$_3$-C$_{10}$)arylene, —(C$_3$-C$_{10}$)arylene-(C$_1$-C$_{10}$)alkylene-, phenylene, —(C$_1$-C$_{10}$)alkylene-(C$_3$-C$_{10}$)cycloalkylene, —(C$_3$-C$_{10}$)cycloalkylene, or —(C$_3$-C$_{10}$)cycloalkylene-(C$_1$-C$_{10}$)alkylene-. For certain Formula I compounds X is a —(C$_3$-C$_{10}$)arylene, such as a phenylene group.

Substituent groups R$^1$ and R$^2$ in Formula I are each independently selected from H, —(C$_1$-C$_{10}$)alkyl, —C(O)—(C$_1$-C$_{10}$)alkyl, benzyl, —(C$_3$-C$_{10}$)cycloalkyl, or —(C$_3$-C$_{10}$)aryl, while groups R$^a$ and R$^b$ are each independently selected from the group consisting of H, —OH, —(C$_1$-C$_{10}$)alkyl, —[CH$_2$—CH$_2$—O]$_n$—(CH$_2$)$_2$-T, —C(O)—(C$_1$-C$_{10}$)alkyl, —(C$_1$-C$_{10}$)alkylene-C(O)—, —(C$_1$-C$_{10}$)alkylene-C(O)—Z, benzyl, —(C$_3$-C$_{10}$)cycloalkyl, —(C$_3$-C$_{10}$)aryl-(C$_1$-C$_{10}$)alkylene, —(C$_3$-C$_{10}$)aryl, halo-(C$_1$-C$_{10}$)alkyl, hydroxy-(C$_1$-C$_{10}$)alkyl, —NH—(C$_1$-C$_{10}$)alkyl, and —(C$_1$-C$_{10}$)alkylene-NR$^d$R$^e$—. For certain Formula I compounds R$^a$ and R$^b$ together with the nitrogen to which they are bonded form a (C$_3$-C$_6$)-heteroaryl or (C$_3$-C$_6$)-heterocycloalkyl that can further comprise one or more heteroatoms selected from N, S, or O.

Z in Formula I can be selected from —OH, —O(C$_1$-C$_{10}$)alkyl,

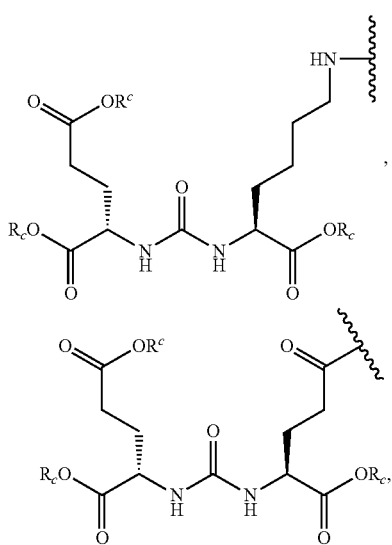

substituent R$^c$ is selected from —OH, —O(C$_1$-C$_{10}$)alkyl, —Obenzyl, —O(C$_3$-C$_{10}$)cycloalkyl, —O(C$_3$-C$_{10}$)aryl, —O—(C$_1$-C$_{10}$)alkylene-(C$_3$-C$_{10}$)aryl, or —O—(C$_1$-C$_{10}$)alkylene-(C$_3$-C$_{10}$)cycloalkyl and R$^3$ is selected from H, halogen, —OH, —NH$_2$, —(CH$_2$)$_p$—COOH, or —(CH$_2$)$_p$—NH$_2$.

In Formula I T is selected from —H, —OH, —COOH, or —NR$^d$R$^e$ and when T is —NR$^d$R$^e$, substituent groups R$^d$ and R$^e$ are each independently selected from H, bond, —OH, —(C$_1$-C$_{10}$)alkyl, or —(C$_3$-C$_{10}$)heteroaryl-(C$_1$-C$_{10}$)alkylene;

Subscripts m, n, p, q, t and r are each independently 0, 1, 2, 3, 4, 5, 6, 7, 8 9, or 10; and the chelator group D is

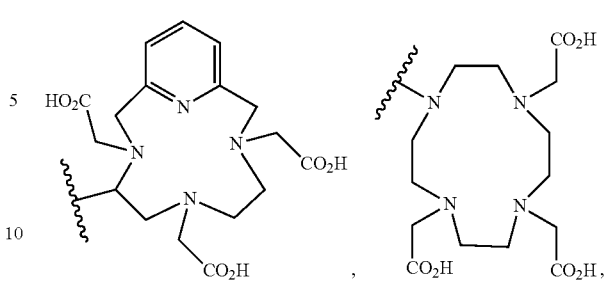

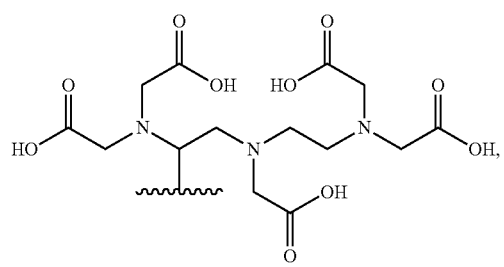

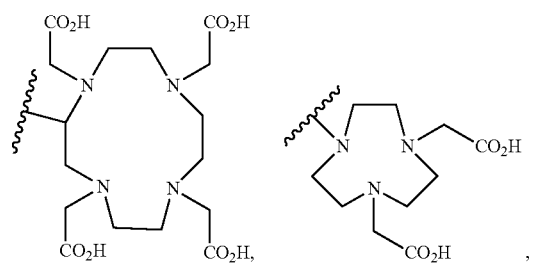

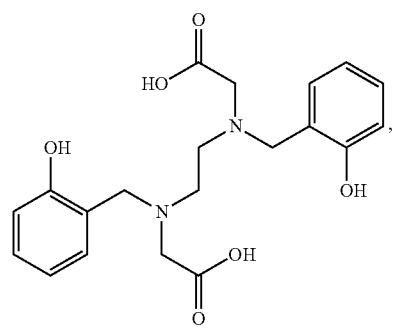

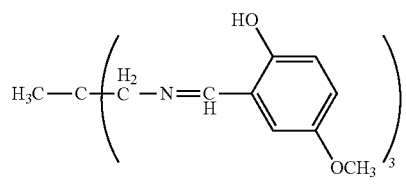

H$_3$ [5-MeOsal)$_3$ TAME]

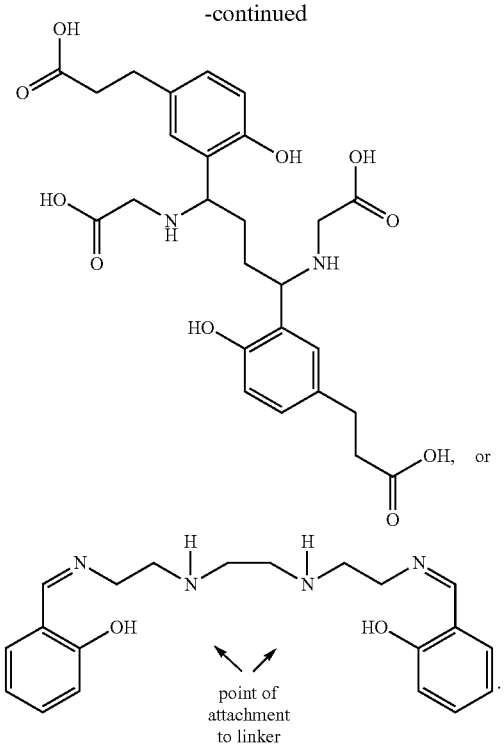

For Formula I compounds any alkyl, alkylene, aryl, arylene, heteroaryl, heteroarylene, cycloalkyl, cycloalkylene, heterocycloalkyl, or heterocycloalkylene is optionally substituted with 1, 2, or 3 substituent groups selected from the group consisting of —($C_1$-$C_{10}$)haloalkyl, —($C_1$-$C_{10}$) aminoalkyl, —($C_1$-$C_{10}$)alkylene-COOH, —($C_1$-$C_{10}$) hydroxyalkyl, —OH, halogen, —$NH_2$, —COOH, —C(O)—($C_1$-$C_{10}$)alkyl, —($C_1$-$C_{10}$)alkylene-C(O)—, —($C_1$-$C_{10}$) alkylene-C(O)—X, —NH—($C_1$-$C_{10}$)alkyl, and —($C_1$-$C_{10}$) alkylene-$NR^dR^e$—, and —$NR^dR^e$.

In one aspect for an inventive Formula I compound X is phenylene, subscript "r" is 1 and D is the metal chelator DOTA. Pursuant to these qualifications is a Formula II compound as illustrated below. For certain Formula II compounds A is $(CHR^1)_m$, W is a C(O)—$(CH_2)_7$— or —C(O)—$(CH_2)_{10}$— group and Y is In one embodiment, A is $(CHR^1)_m$ with $R^1$ being a hydrogen and m is 2. For certain Formula II compounds $R^a$ and $R^b$ together with the nitrogen to which they are bonded form a ($C_3$-$C_6$)-heterocycloalkyl selected from piperidine, piperazine, morpholine, thiomorpholine, isothiazolidine, isoxazolidine, pyrrolidine, immidazolidine, thiazolidine or oxazolidine. For some Formula II compounds $R^a$ is —H and $R^b$ is with $R^d$ and $R^e$ each independently being a —$(C_3-C_{10})$heteroaryl-$(C_1-C_{10})$alkylene, for example, $R^d$ and $R^e$ are each independently

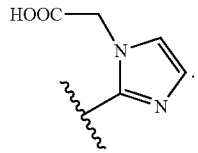 [SMILES: *c1nccn1CC(=O)O]

An illustrative Formula II compound that comports with the above definition is illustrated below:

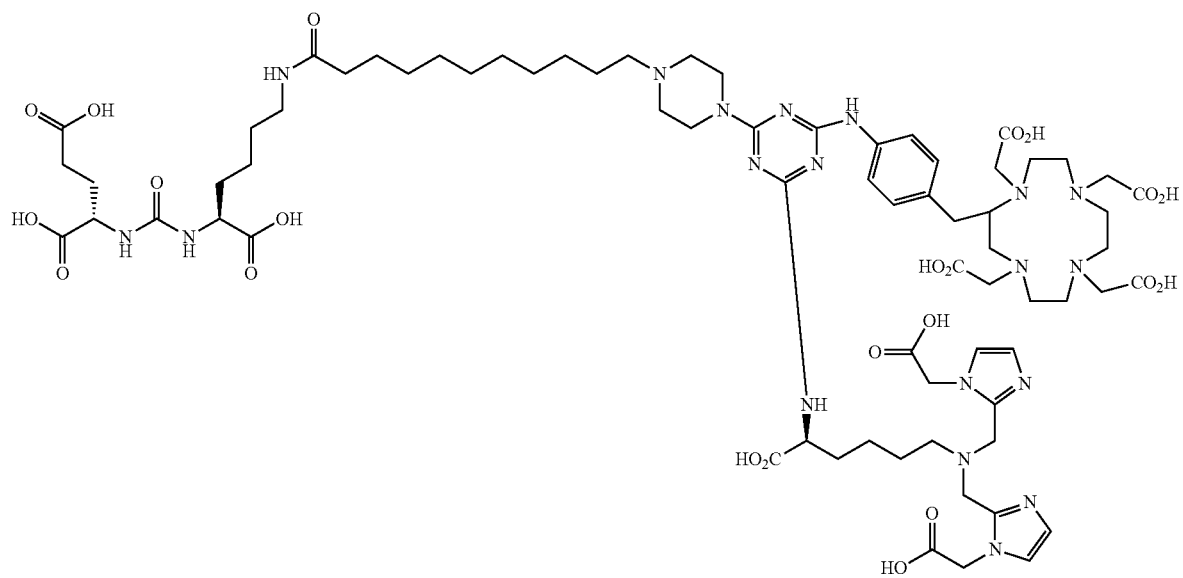 [SMILES: O=C(O)CC[C@H](NC(=O)N[C@@H](CCCCNC(=O)CCCCCCCCCCN1CCN(c2nc(Nc3ccc(CC4CN(CC(=O)O)CCN(CC(=O)O)CCN(CC(=O)O)CCN4CC(=O)O)cc3)nc(N[C@@H](CCCCN(Cc3nccn3CC(=O)O)Cc3nccn3CC(=O)O)C(=O)O)n2)CC1)C(=O)O)C(=O)O]

Other exemplary Formula I or Formula II compounds include without limitation compounds mentioned in Table 1 below. While some exemplary compounds are depicted with stereochemistry, it should be understood that the invention includes all possible stereoisomers, such as diastereomers, of the compounds.

TABLE 1

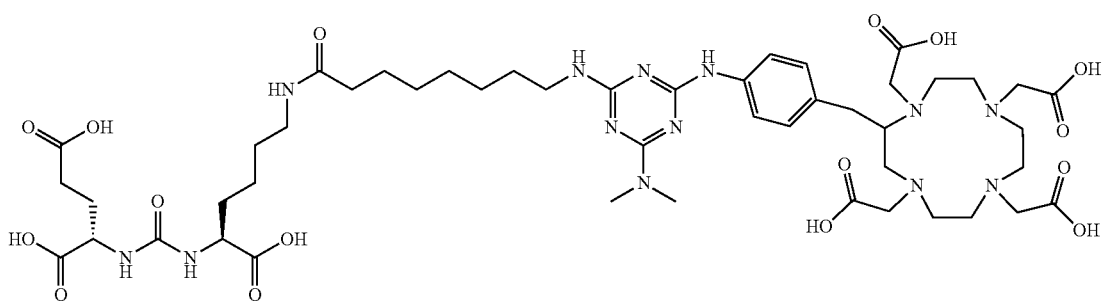 [SMILES: CN(C)c1nc(NCCCCCCCC(=O)NCCCC[C@H](NC(=O)N[C@@H](CCC(=O)O)C(=O)O)C(=O)O)nc(Nc2ccc(CC3CN(CC(=O)O)CCN(CC(=O)O)CCN(CC(=O)O)CCN3CC(=O)O)cc2)n1]

TABLE 1-continued
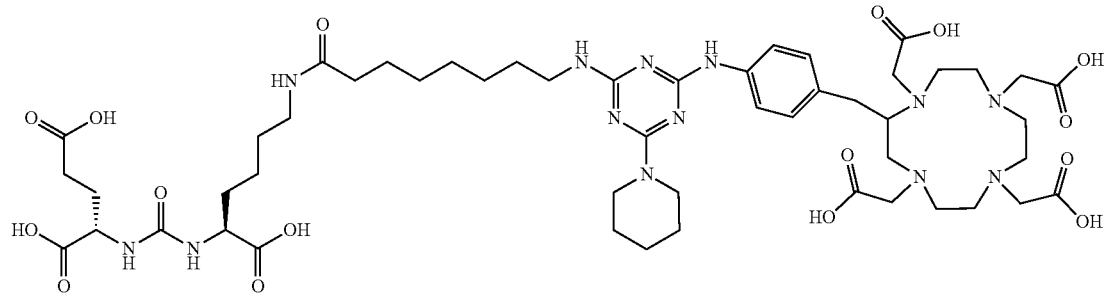 [SMILES: O=C(O)CC[C@H](NC(=O)N[C@@H](CCCCNC(=O)CCCCCCCNc1nc(Nc2ccc(CC3CN(CC(=O)O)CCN(CC(=O)O)CCN(CC(=O)O)CCN3CC(=O)O)cc2)nc(N2CCCCC2)n1)C(=O)O)C(=O)O]
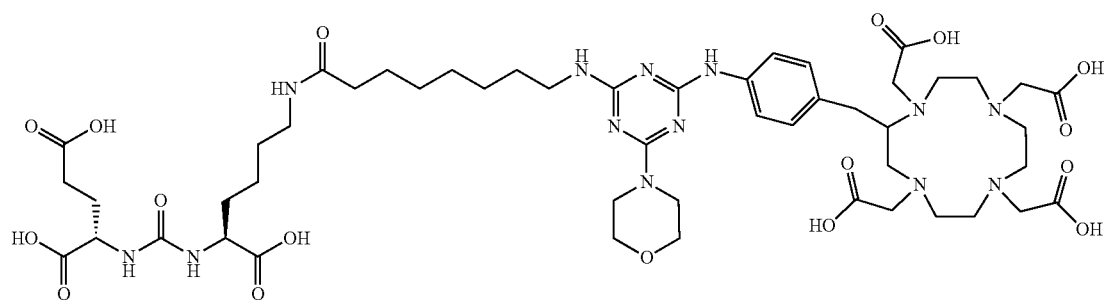 [SMILES: O=C(O)CC[C@H](NC(=O)N[C@@H](CCCCNC(=O)CCCCCCCNc1nc(Nc2ccc(CC3CN(CC(=O)O)CCN(CC(=O)O)CCN(CC(=O)O)CCN3CC(=O)O)cc2)nc(N2CCOCC2)n1)C(=O)O)C(=O)O]
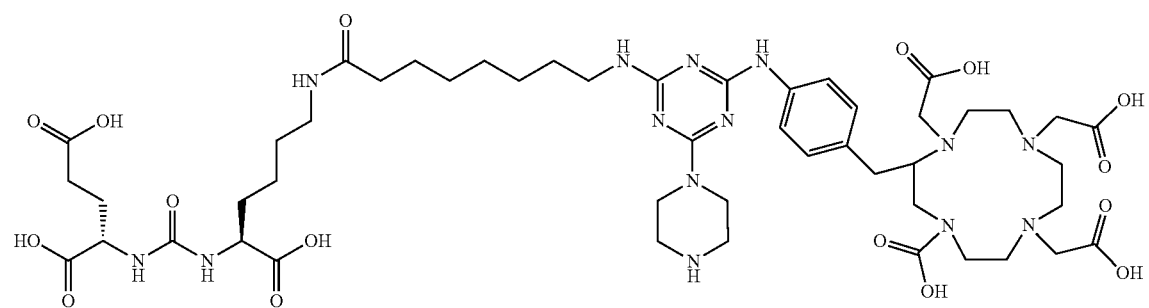 [SMILES: O=C(O)CC[C@H](NC(=O)N[C@@H](CCCCNC(=O)CCCCCCCNc1nc(Nc2ccc(CC3CN(C(=O)O)CCN(CC(=O)O)CCN(CC(=O)O)CCN3CC(=O)O)cc2)nc(N2CCNCC2)n1)C(=O)O)C(=O)O]
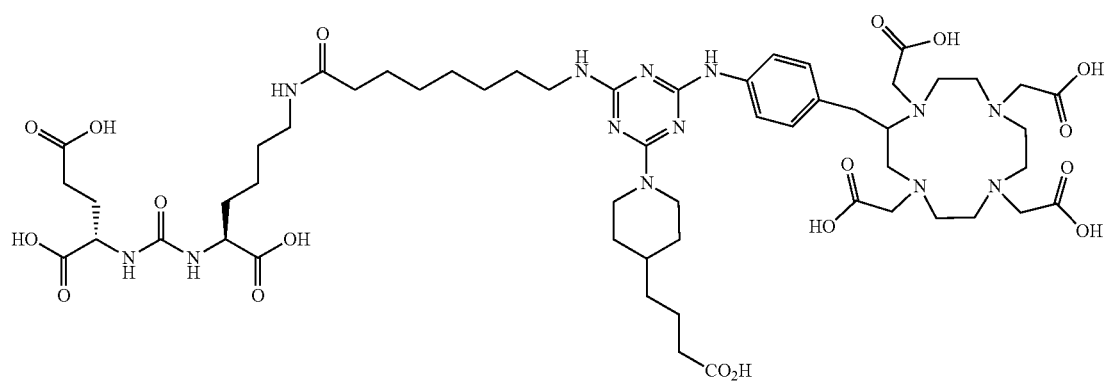 [SMILES: O=C(O)CCCC1CCN(c2nc(NCCCCCCCC(=O)NCCCC[C@H](NC(=O)N[C@@H](CCC(=O)O)C(=O)O)C(=O)O)nc(Nc3ccc(CC4CN(CC(=O)O)CCN(CC(=O)O)CCN(CC(=O)O)CCN4CC(=O)O)cc3)n2)CC1]

TABLE 1-continued
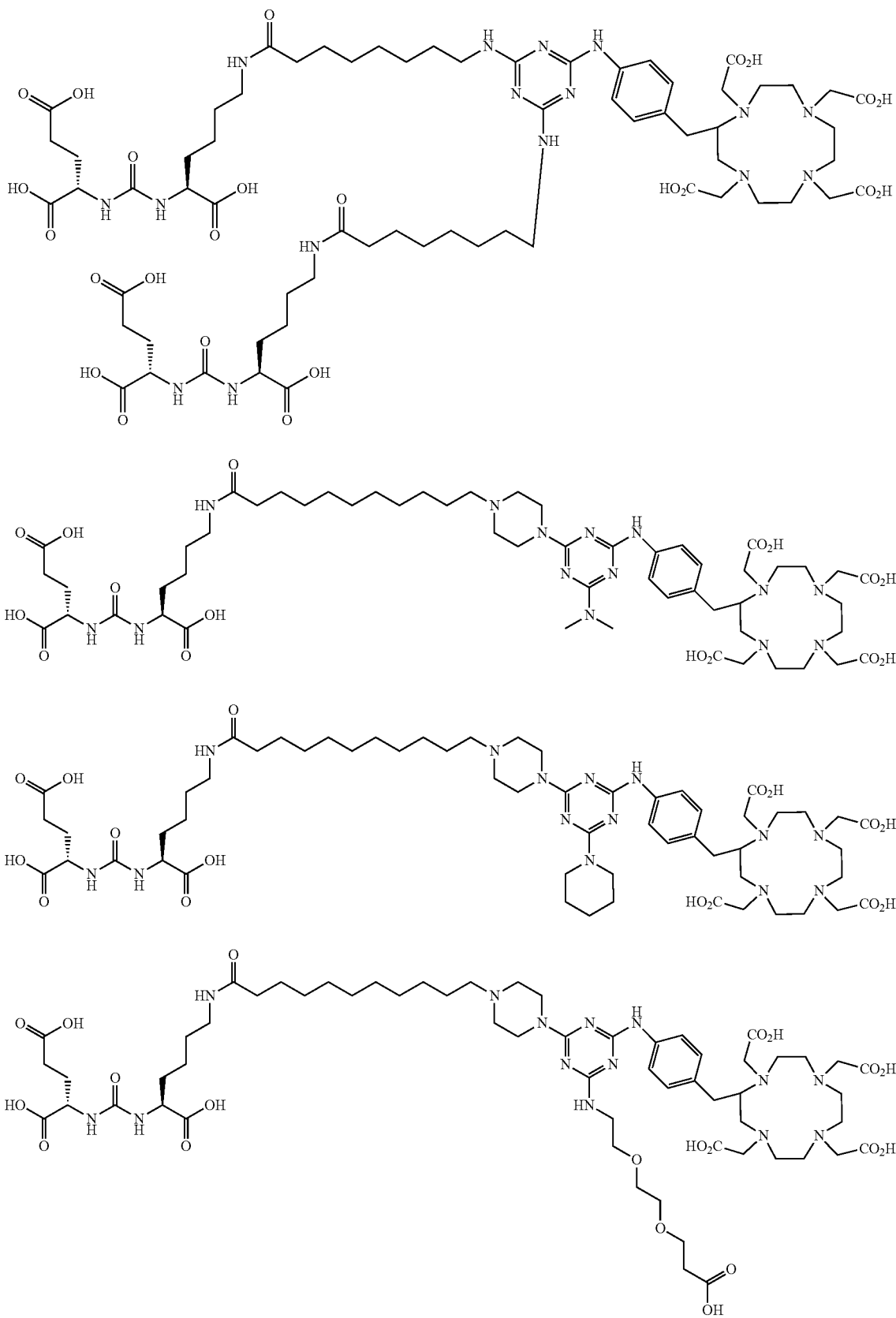

TABLE 1-continued
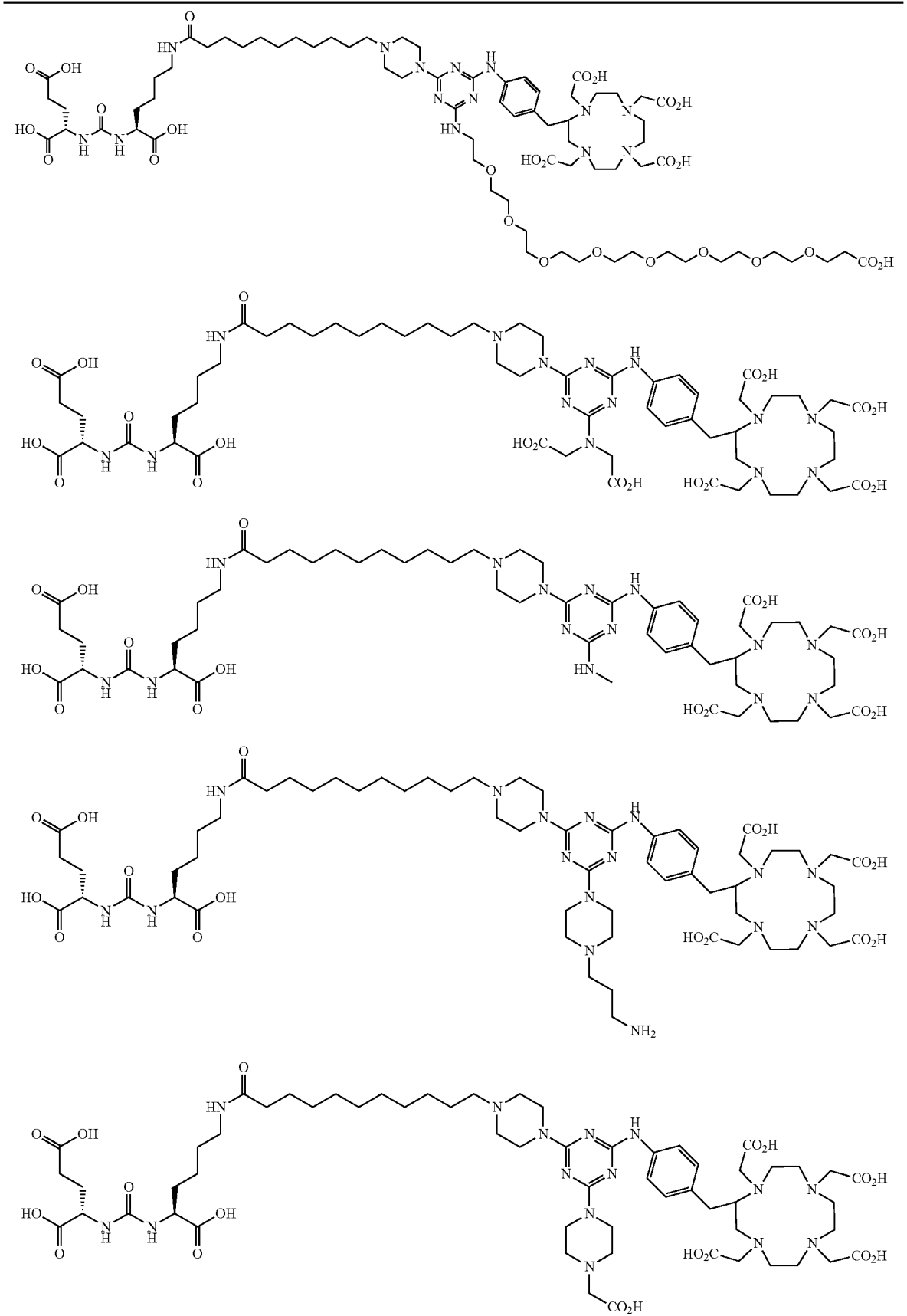

TABLE 1-continued

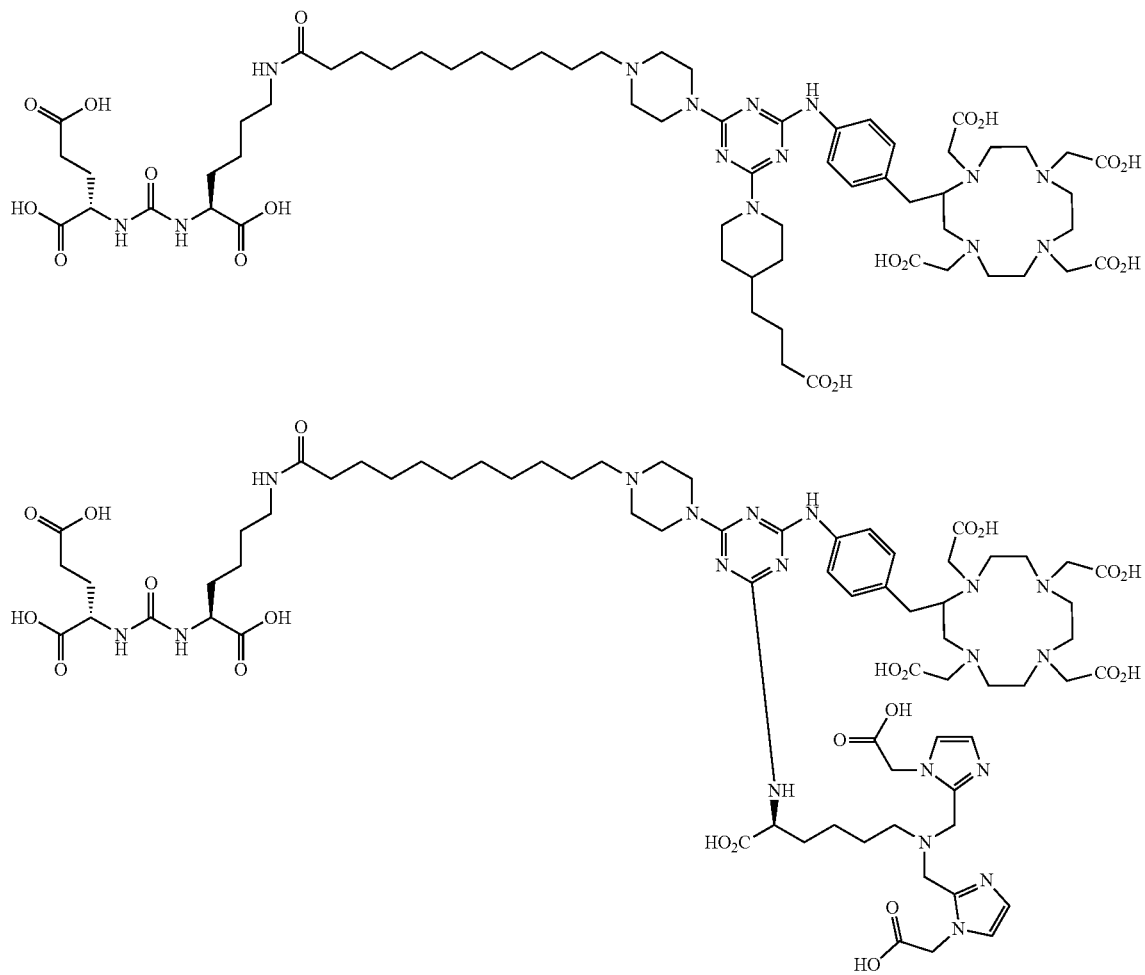

Pharmaceutically acceptable salts and/or solvates of the inventive Formula I and Formula II compounds illustrated above are also within the scope of the present invention. In some embodiments, the chelator group, for example, the DOTA group is not complexed with a radionuclide. When DOTA is uncomplexed the carboxylic acid groups of the DOTA group can be in the form of a free acid, or in the form of a salt. The free carboxylic acid groups can also be esterified to obtain the prodrug form of Formula I or Formula II compounds. Suitable ester prodrugs include various alkyl esters, including saturated and unsaturated $C_8$ to $C_{18}$ fatty acids.

The inventive compounds are glutamate-urea-lysine (GUL-) or glutamate-urea-glutamate (GUG) analogs in which a chelator group is conjugated to the GUL- or GUG-moiety via a linker.

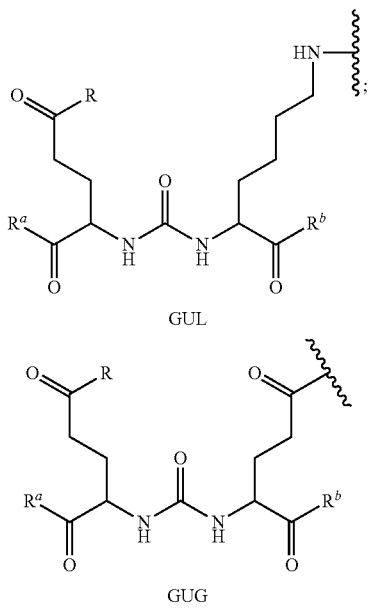

As further discussed below, the length and chemical nature of the linker group is believed to influence the binding avidity of the inventive compounds to the target tissue. Thus, radionuclide complexes of Formula I or Formula II compounds having a piperazine-triazinyl-p-aminobenzyl-DOTA moiety within the linker were observed to concentrate to a greater extent in tumor tissue than non-tumor tissue, such as blood, heart, lungs, liver, spleen, stomach, large and small intestines, testes, skeletal muscle, bone, brain, and adipose tissue.

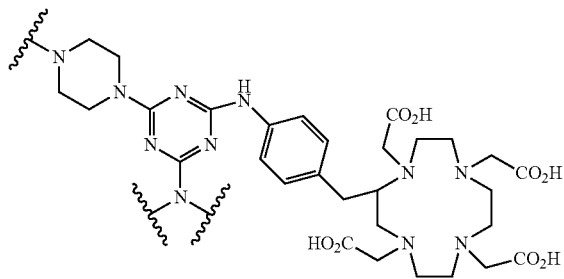 [SMILES: *N1CCN(c2nc(Nc3ccc(CC4CN(CC(=O)O)CCN(CC(=O)O)CCN(CC(=O)O)CCN4CC(=O)O)cc3)nc(N(*)*)n2)CC1]

These compounds, moreover, were rapidly cleared by the kidneys. It was observed that over a period of 96 hours, the piperazine-triazinyl-p-aminobenzyl-DOTA containing compounds initially concentrated in the kidneys but at longer intervals of time were rapidly cleared by the kidneys. For example, Formula I or Formula II compounds concentrate to a greater extent in the kidneys than tumor at 4 hours post administration. However, the concentration of the inventive compounds in tumor did not change as a function of time. Thus, the tumor concentration of Formula I or Formula II compounds at 4 hours post administration is similar to their tumor concentration at 24 hours and 96 hours post administration.

Depending on whether the Formula I or Formula II compounds are to be used as radioimaging agents or radio pharmaceuticals, different radionuclides are complexed to the compounds. Illustrative of suitable radionuclides are those selected from the actinide series, lanthanide series and radionuclides of transition metals, for example $^{111}$In, $^{90}$Y, $^{68}$Ga, $^{64}$Cu, $^{153}$Gd, $^{155}$Gd, $^{157}$Gd, $^{59}$Fe, $^{225}$Ac, $^{212}$Bi, $^{213}$Bi, $^{55}$Co, $^{67}$Cu, $^{165}$Dy, $^{166}$Ho, $^{192}$Ir, $^{223}$Ra, $^{186}$Re, $^{188}$Re, $^{105}$Rh, $^{212}$Pb, $^{213}$Pb, $^{149}$Tb, $^{227}$Th, $^{153}$Sm, $^{89}$Sr, $^{117m}$Sn, $^{169}$Yb, $^{90}$Y, $^{86}$Y, $^{89}$Zr and $^{177}$Lu.

Illustrative of Formula I or Formula II compounds complexed to an exemplary radionuclide $^{177}$Lu are those illustrated below in Table 2.

TABLE 2

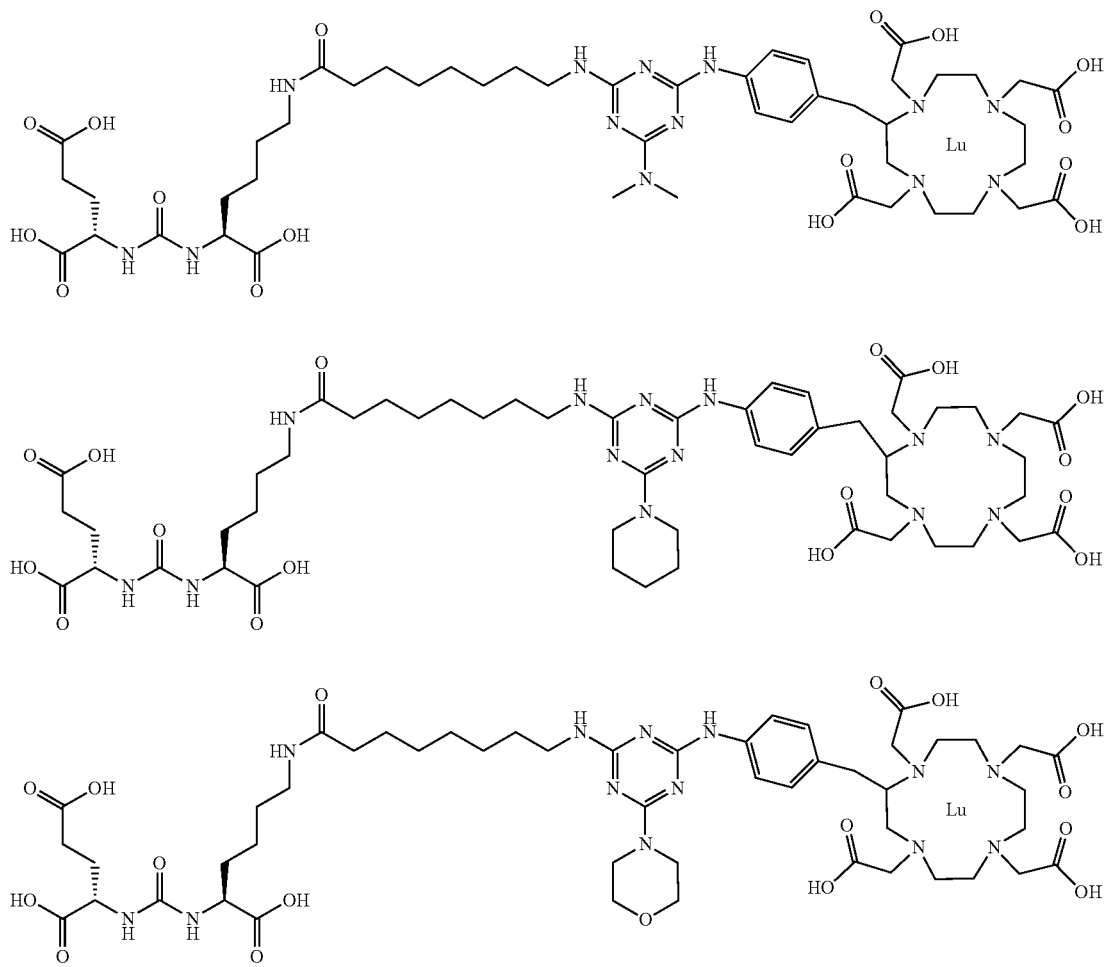

TABLE 2-continued
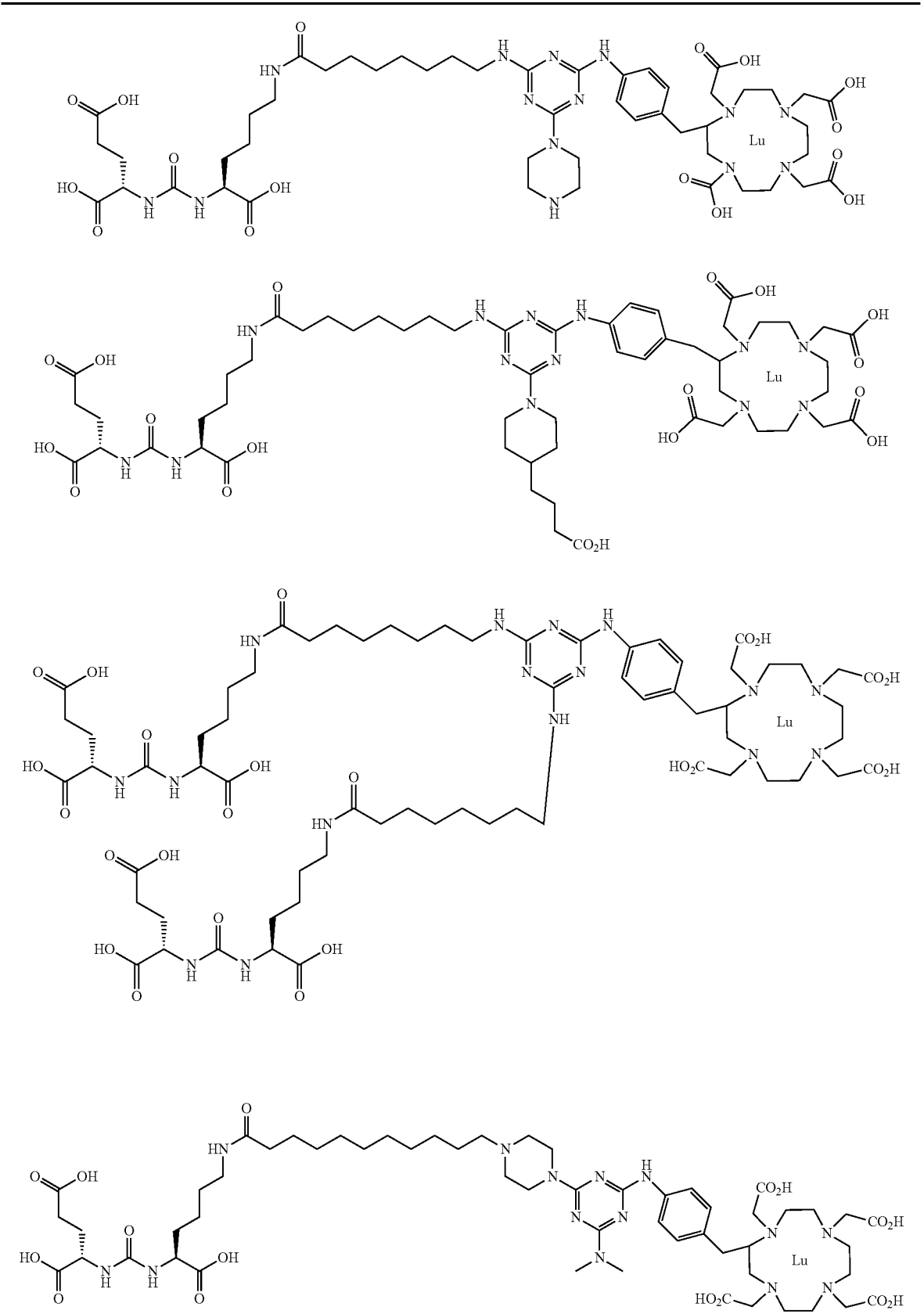

TABLE 2-continued
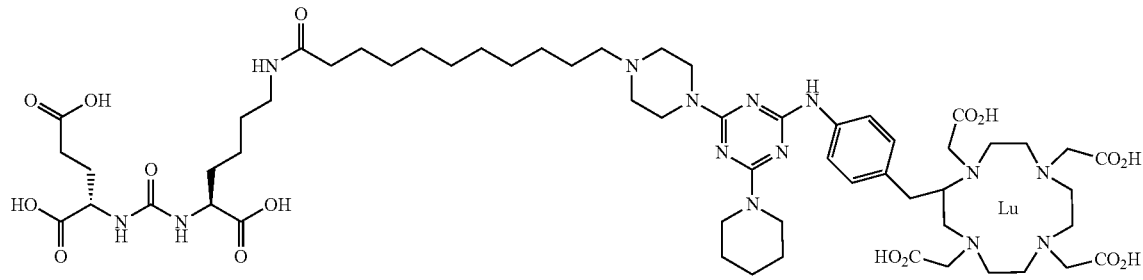
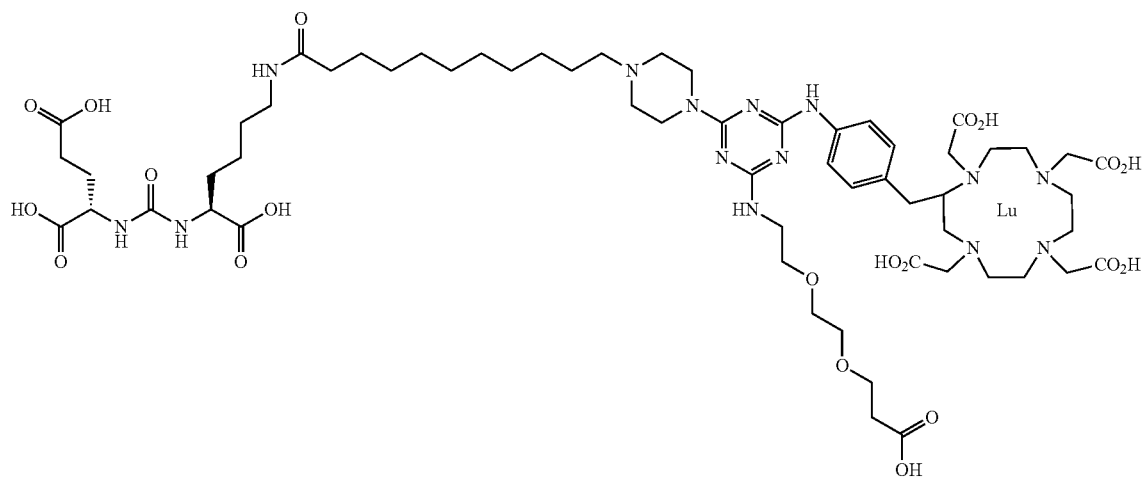
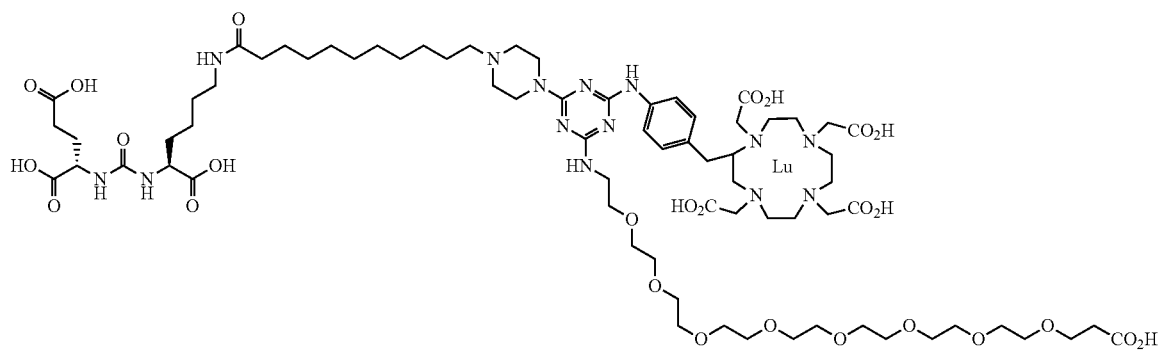

TABLE 2-continued
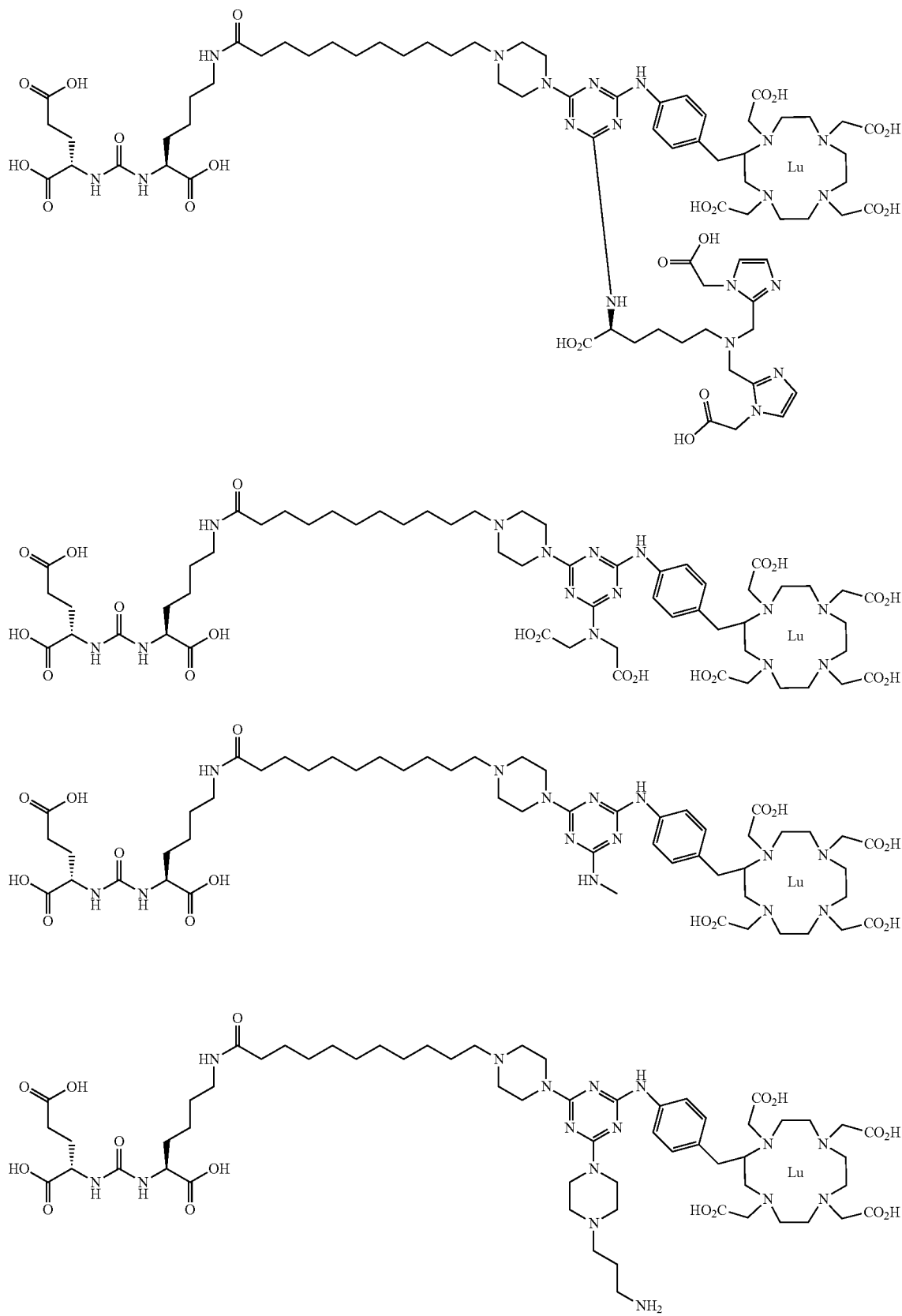

TABLE 2-continued

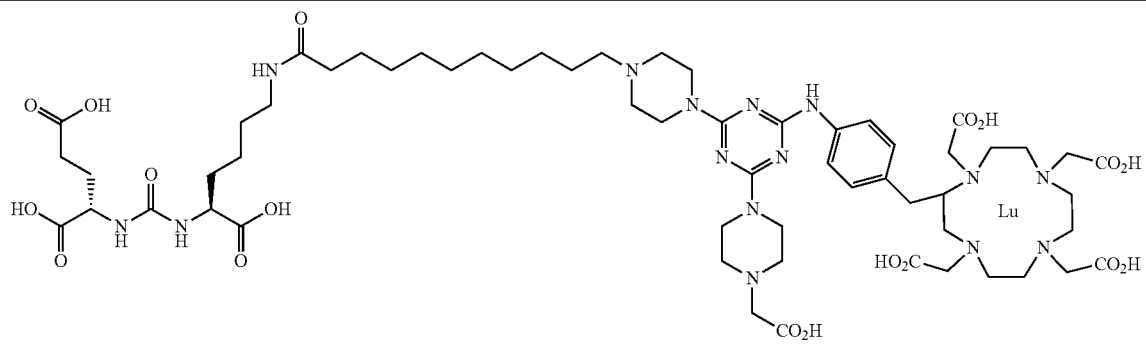

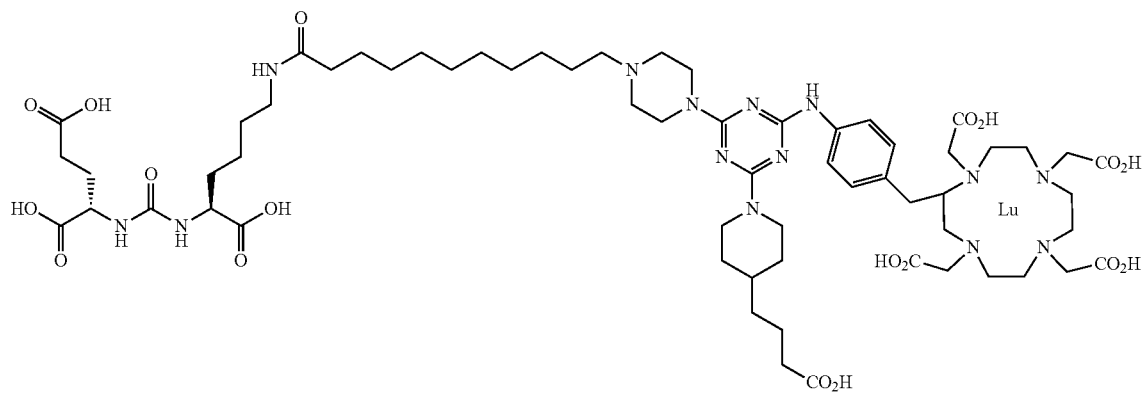

or a pharmaceutically acceptable salt or solvate thereof.

Figure 2:
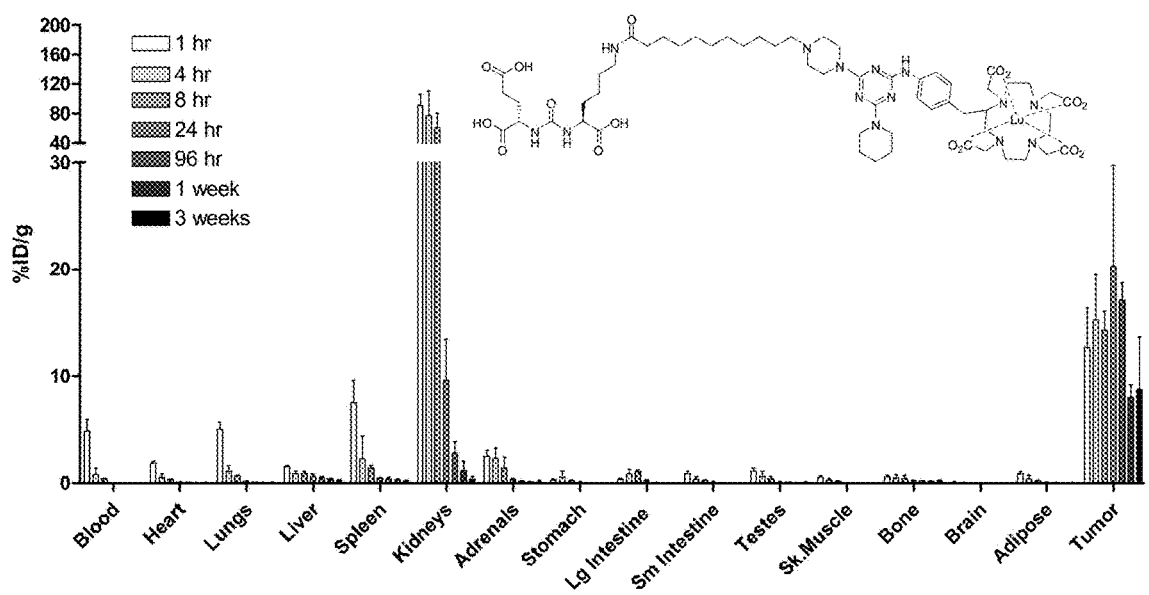
FIG. 2 illustrates tissue biodistribution of the $^{177}$Lu-complex of (2S)-2-(3-((1S)-1-carboxy-5-(11-(4-(4-(piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid according to the present invention in LNCap Xenograft mice.
Figure 3:
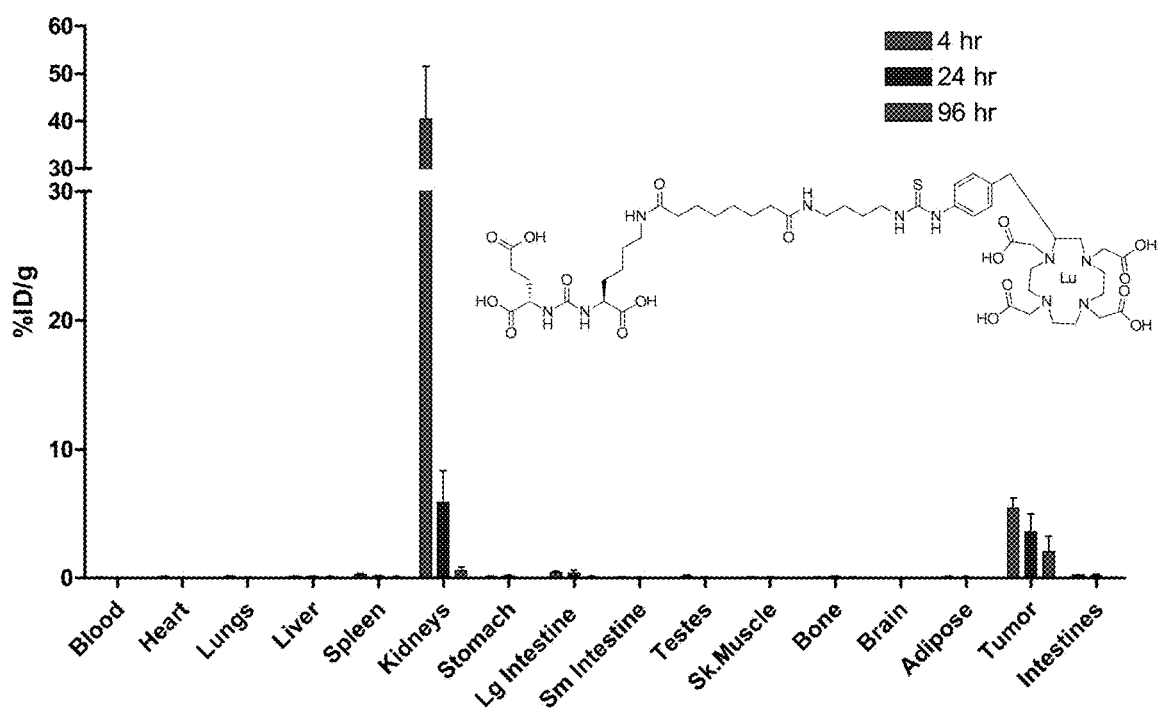
FIG. 3 illustrates tissue biodistribution of the $^{177}$Lu-complex of (21S,25S)-8,15,23-trioxo-1-(4-((1,4,7,10-tetrakis(carboxymethyl)-1,4,7,10-tetraazacyclododecan-2-yl)methyl)phenylamino)-1thioxo-2,7,16,22,24-pentaazaheptacosane-21,25,27-tricarboxylic acid used as a control in LNCap Xenograft mice.

FIG. 1 and FIG. 2 illustrate results of a bio-distribution study of a GUL-[piperazine-triazinyl-p-aminobenzyl]-DOTA-$^{177}$Lu complexes according to Formula I or Formula II in LNCap xenograft mice, while FIG. 3 illustrates results of a bio-distribution study of a GUL-[alkylene thiourea]-DOTA-$^{177}$Lu complex in LNCap xenograft mice.

(A)

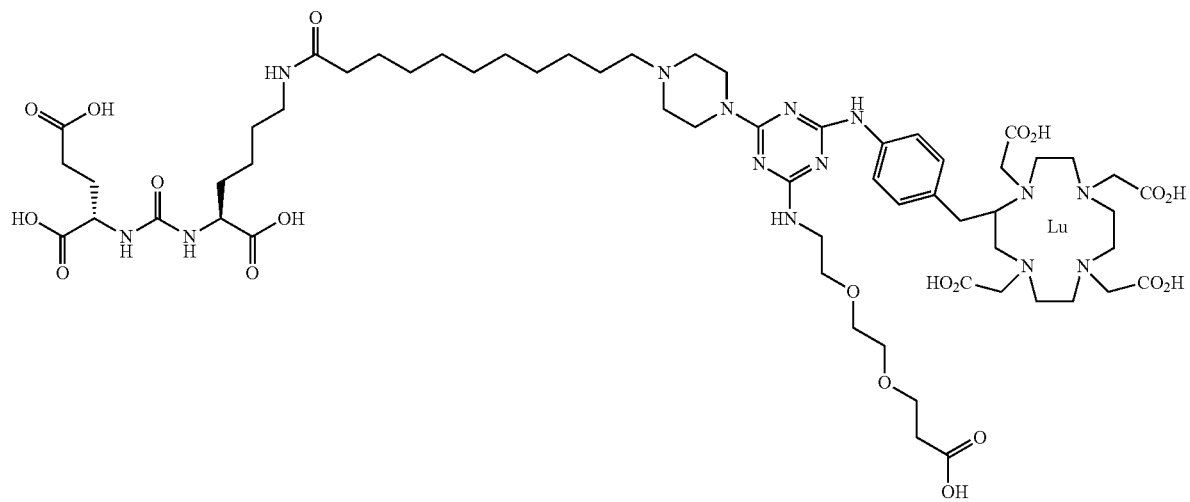

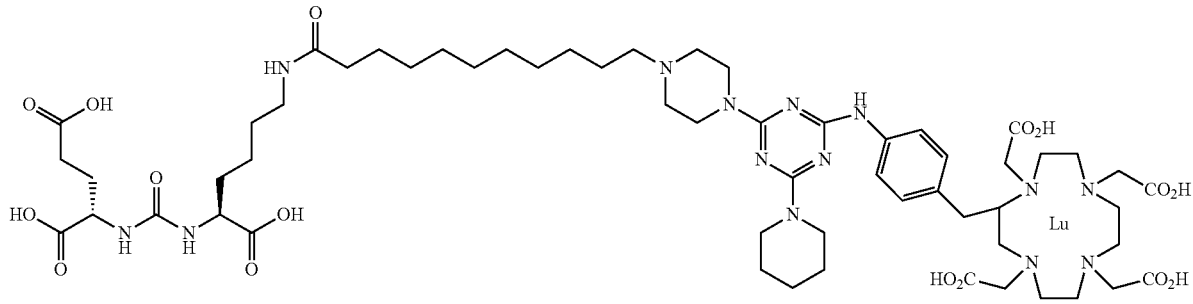

(B)

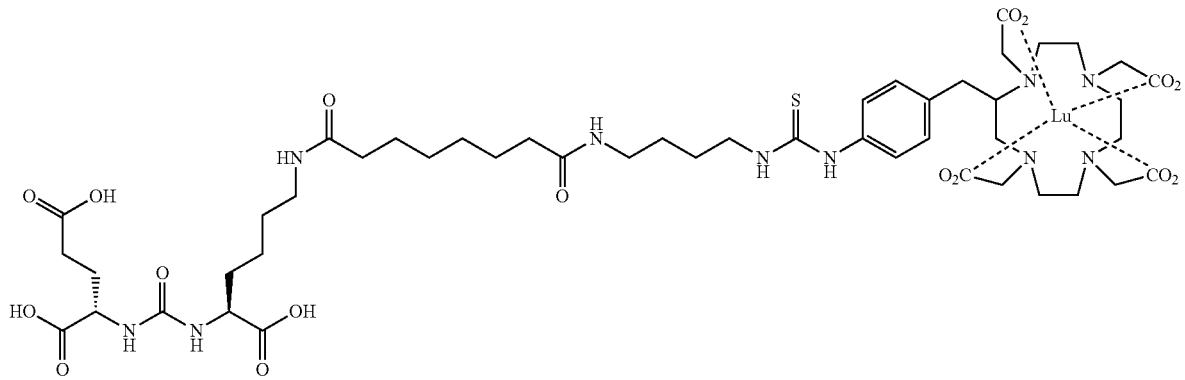

(C)

As illustrated by the bar graphs in these figures, complexes (A), (B) and (C) concentrate in kidneys and tumor to a greater extent than other tissues. In fact, at 4 hours post administration, the observed concentration for each complex (A), (B) and (C) was greater in kidneys than in tumor. As illustrated by FIGS. 1-3, however, at 24 hours and 96 hours post administration the concentration of the inventive GUL-[piperazine-triazinyl-p-aminobenzyl]-DOTA-$^{177}$Lu complexes (A) and (B) in LNCap tumor cells remained unchanged while the concentration of complex (C) used as a control decreases in LNCAP tumor cells at these longer intervals of time.

These results were unexpected and suggest a greater ability for radionuclide complexes of Formula I or Formula II compounds to concentrate in tumor cells. Moreover, as illustrated in FIGS. 1 and 2, inventive complexes (A) and (B) are rapidly cleared from the kidneys. Because radionuclide complexes of Formula I or Formula II compounds concentrate in tumor and are rapidly cleared by the kidneys, radionuclide complexes of Formula I or Formula II compounds are candidate therapeutics for treating cancer, for example, prostate cancer.

Further confirmation that the inventive complexes concentrate in LNCaP tumors but are more rapidly cleared from other tissues including kidneys post administration to LNCaP tumor bearing mice was obtained in a separate extended biodistribution study using the GUL-[piperazine-triazinyl-p-aminobenzyl]-DOTA-$^{177}$Lu complex (D), illustrated below.

(D)

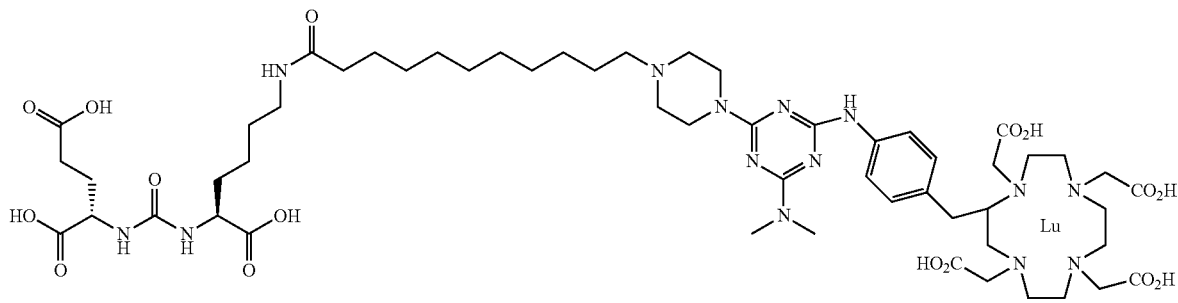

Figure 4:
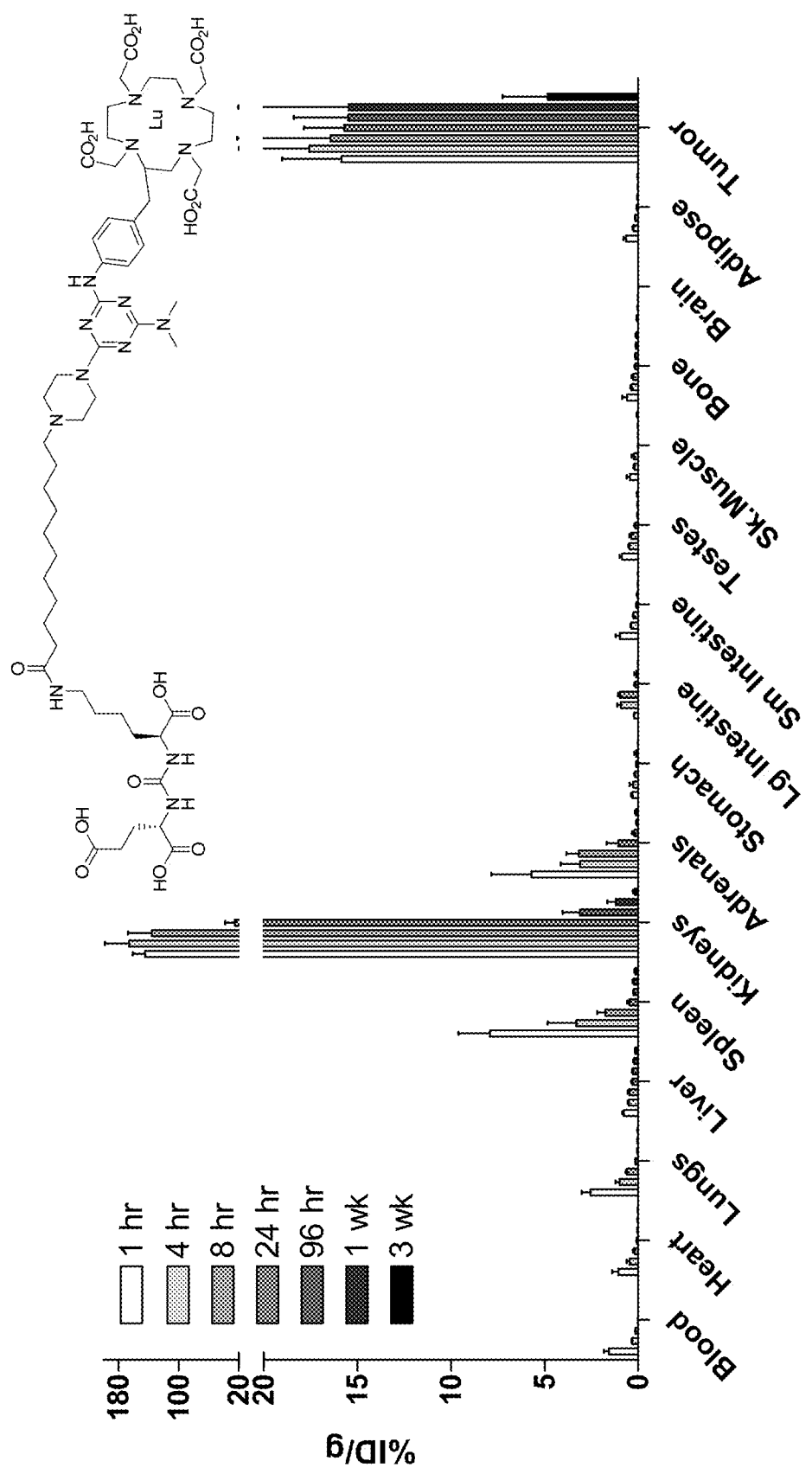
FIG. 4 illustrates tissue biodistribution of the $^{177}$Lu-complex of (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido) pentanedioic acid according to the present invention in LNCap Xenograft mice.

As illustrated by the bar graph in FIG. 4, the inventive complex concentrates to a greater extent in kidneys and tumor than other tissues at shorter time intervals post administration. For instance, there is a gradual increase in the concentration of complex (D) in kidneys and tumor as a function of time over the first eight hours post administration. At longer time intervals, for example between 24 hours to 96 hours however, the concentration of complex (D) in kidney decreases while there is no observable change in the concentration of complex (D) in tumor.

To further investigate the pharmacokinetics of tumor retention and renal clearance, the biodistribution study was extended to 3 weeks. Tissue analysis at 1 week post administration of complex (D) indicated no appreciable change in the intracellular concentration of this complex in LNCaP tumor cells. The intrarenal concentration at 1 week post administration of complex (D) is significantly lower than the intrarenal concentration of complex (D) at earlier time intervals, for example, within eight hours post administration.

At 3 weeks post administration, tissue analysis indicates a decrease in the intratumoral concentration of complex (D). However, the decrease in the concentration of the inventive complex in tumor is less compared to the decrease in the intrarenal concentration of complex (D). As mentioned above, the extended biodistribution study confirmed initial observations that within the same period of time there is a more rapid decrease in the concentration of complex (D) from the kidneys than tumor. Taken together, these results illustrate a greater affinity for the inventive radionuclide complexes that comport with Formula I or Formula II for tumor cells than non-tumor tissue, such as blood, heart, lungs, liver, spleen, stomach, large and small intestines, testes, skeletal muscle, bone, brain, and adipose tissue.

Accordingly, Formula I and Formula II compounds are candidate therapeutic or imaging agents for selectively imaging LNCap tumor cells.

The compounds of Formula I or Formula II were screened in a human prostate cancer cell competitive binding assay using PSMA positive (+), LnCap cells against the known inhibitor of PSMA, (7S,14S,18S)-7-amino-1-(1-(carboxymethyl)-1H-imidazol-2-yl)-2-((1-(carboxymethyl)-1H-imidazol-2-yl)methyl)-8,16-dioxo-2,9,15,17-tetraazaicosane-14,18,20-tricarboxylic acid ($^{99m}$Tc-MIP-1405), and $IC_{50}$ values were calculated.

Briefly, LNCaP human prostate cancer cells were obtained from American Type Culture Collection, Rockville, Md. LNCaP cells were maintained in RPMI-1640 medium supplemented with 10% fetal bovine serum (FBS). Binding of the radiolabeled compound and competition with cold derivatives to LNCaP cells was performed according to published methods. Cells were plated in 12-well plates at approximately $4 \times 10^5$ cells/well and incubated for 48 hours in a humidified incubator at 37° C./5% carbon dioxide prior to addition of compound. Solutions of the Formula I or Formula II compounds were prepared and diluted in serum-free cell culture medium containing 0.5% bovine serum albumin (BSA) in combination with 3 nM $^{99m}$Tc-MIP-1405 (known inhibitor). Total binding was determined by incubating $^{99m}$Tc-MIP-1405 without test compound. Plates were incubated at room temperature for 1 hour. Cells were removed from the plates and transferred to eppendorff tubes. Samples were microcentrifuged for 15 seconds at 10K x g. The medium was aspirated and the pellet was washed twice by dispersal in fresh assay medium followed by microcentrifugation. Cell binding of $^{99m}$Tc-MIP-1405 was determined by counting the cell pellet in an automated gamma counter. Table 3 illustrates the $IC_{50}$ values of representative Formula II non-radioactive $^{175}$Lu complexes.

TABLE 3

| Complex | $IC_{50}$ (nM) |
|---|---|
| [chemical structure] | 7.2 |
| [chemical structure] | 11 |

TABLE 3-continued

| Complex | IC$_{50}$ (nM) |
|---|---|
| [structure] | 20 |
| [structure] | 6.7 |
| [structure] | 47 |
| [structure] | 1.3 |

TABLE 3-continued

| Complex | IC$_{50}$ (nM) |
|---|---|
| (structure) | 13 |
| (structure) | 10 |
| (structure) | 40 |
| (structure) | 129 |
| (structure) | 90 |

TABLE 3-continued

| Complex | IC$_{50}$ (nM) |
|---|---|
| (structure) | 121 |
| (structure) | 22 |
| (structure) | 20 |
| (structure) | 17 |
| (structure) | 6 |

As illustrated above, Formula I and Formula II compounds of the invention bind to PSMA expressed on the surface of prostate cancer cells with IC$_{50}$ values in the nanomolar range. The inventive compounds, therefore, are candidate radiotherapeutic agents for inhibiting the growth of prostate cancer tumor. Please note that in some structures depicted above and elsewhere in this disclosure there may or may not be dashed or solid lines showing putative interactions between certain functional groups and a metal radionuclide. These depictions are merely illustrative of possible bonding interactions, but by no means should they be interpreted as the only possible or actual metal-ligand interaction(s) present for the particular metal complex depicted. For example, it is possible, perhaps even probably, that one or more of the macrocylic aza groups are contributing to the overall bonding interactions between the metal ion and the chelating ligand.

Figure 5:
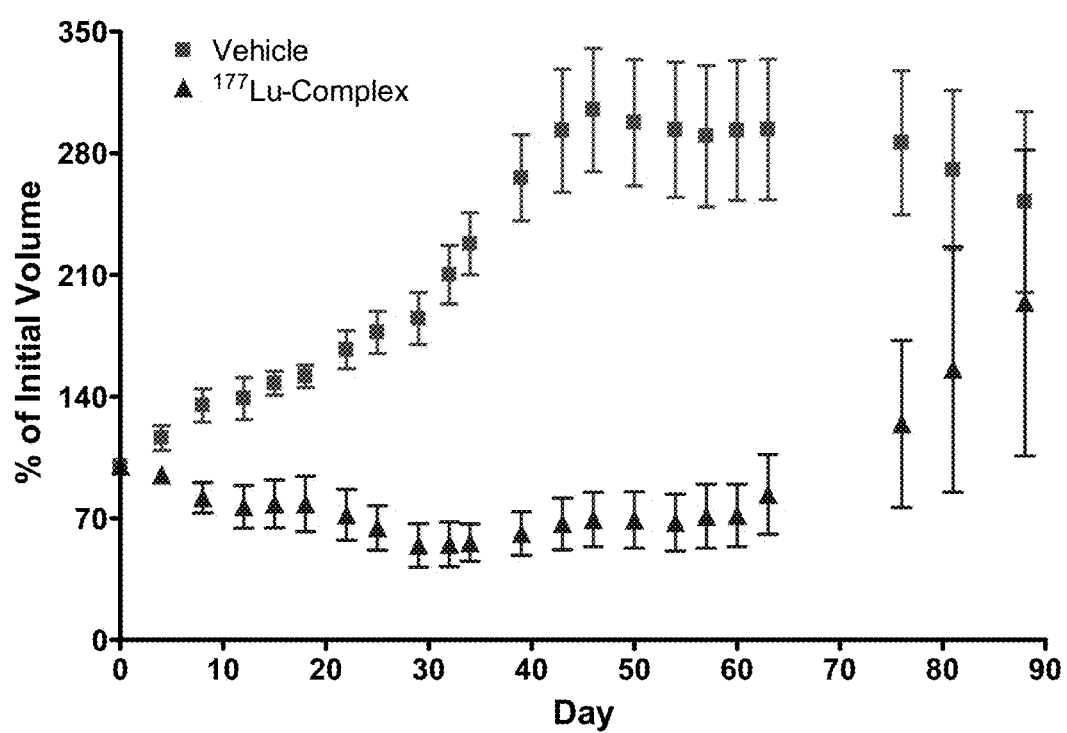
FIG. 5 illustrates in vivo inhibition of LNCaP tumor growth by $^{177}$Lu-complex of (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid.

FIG. 5 illustrates the in vivo efficacy of an exemplary lutetium complex of the invention to inhibit the growth of LNCaP tumors in mice. Arrest of tumor growth was determined by administering 450 µCi of the lutetium complex of (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl) piperazin-1-yl)undecanamido)pentyl)ureido)pentanedioic acid to each mouse in the study group. Mice in the control group were administered saline. Tumor volumes in the test and control group of mice were measured twice weekly. Tumor volumes of mice receiving the lutetium complex according to the invention, were significantly lower than the tumor volumes of mice in the control group.

In fact, as illustrated in FIG. 5, LNCaP tumor volumes of mice in the test group were observed to decrease to values lower than the tumor volume at the start of the study upon administration of the inventive complex. In contrast, there was an increase in the volume of LNCaP tumors in mice receiving saline. These observations indicate that radionuclide complexes of the inventive Formula I and Formula II compounds are effective at arresting the growth of prostate cancer in vivo.

Figure 6:
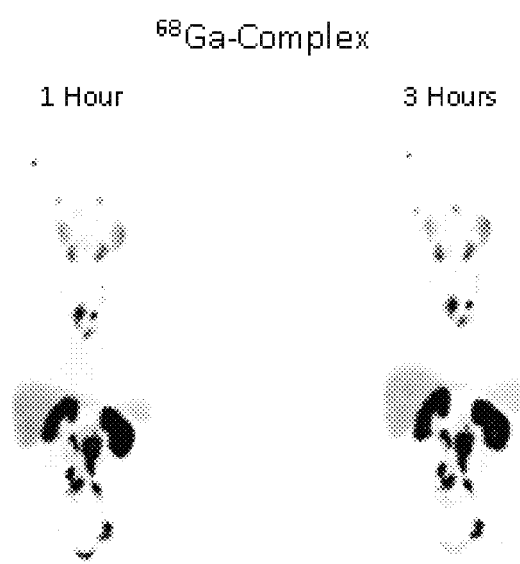
FIG. 6 illustrates a radiographic image obtained by administering to a subject having prostate cancer a $^{68}$Ga complex of (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido) pentanedioic acid.

According to another embodiment of the invention, radiometal complexes of Formula I and Formula II compounds were used for imaging prostate cancer and accompanying metastasis in a subject. Briefly, $^{68}$Ga was complexed to (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl) piperazin-1-yl)undecanamido)pentyl)ureido) pentanedioic acid and the resultant complex was administered to a subject having prostate cancer. The subject was then imaged at 1 hour and 3 hours post administration of the inventive $^{68}$Ga complex using, for example, a $^{68}$Ga-PSMA PET/CT scanner. As illustrated in FIG. 6, PSMA specific lesions were detected in the lymph nodes and bone, in addition to the prostate tissue itself. Some imaging agent was also visible in the subject's bladder at hour 1, which was cleared by the 3-hour scan. The radiographic image in FIG. 6 further indicates that the inventive complex accumulates in the lacrimal and salivary glands, kidney, liver, and urinary bladder. Overall, this imaging study supports the use of radiometal complexes of the inventive compounds as suitable agents for radioimaging of cancers, such as prostate cancer.

Because Formula I and Formula II compounds and their radionuclide complexes can have one or more chiral centers, the present invention encompasses both enantiomers, as well as all of the diasteroisomers. Moreover, both L and D-forms of the natural amino acids can be used for synthesizing the Formula I and Formula II compounds. That is, the present invention encompasses stereoisomers, tautomers, and prodrugs of Formula I and Formula II compounds and their radionuclide complexes.

As noted above, radionuclide complexes of Formula I or Formula II compounds may contain one or more radionuclides which are suitable for use as radio-imaging agents or as radio-therapeutics for the treatment of diseases associated with the uncontrolled and rapid proliferation of cells, for example, PSMA expressing prostate cancer cells. Accordingly, in one embodiment, a pharmaceutical composition is provided including a complex that includes a metal and a compound of Formula I or Formula II, a salt, solvate, stereoisomer, or tautomer thereof, and a pharmaceutically acceptable carrier.

In general, metal complexes of a Formula I or a Formula II compound or pharmaceutical compositions thereof, may be administered orally, or via a parenteral route, usually by injection. Parenteral routes include, but are not limited to, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. In some embodiments, the compound, or pharmaceutical composition thereof, is administered orally. Such compositions may take the form of tablets, pills, capsules, semisolids, powders, solutions, suspensions, elixirs, aerosols, or any other appropriate compositions.

According to another aspect, a pharmaceutical composition is provided, which is suitable for in vivo imaging and radiotherapy. Suitable pharmaceutical compositions may contain a radio imaging agent, or a radiotherapeutic agent that has a radionuclide either as an element, i.e. radioactive iodine, or a radioactive metal chelate complex of the compound of Formula I or Formula II in an amount sufficient for imaging, together with a pharmaceutically acceptable radiological vehicle. The radiological vehicle should be suitable for injection or aspiration, such as human serum albumin; aqueous buffer solutions, e.g., tris(hydromethyl) aminomethane (and its salts), phosphate, citrate, bicarbonate, etc; sterile water; physiological saline; and balanced ionic solutions containing chloride and or dicarbonate salts or normal blood plasma cations such as calcium, potassium, sodium, and magnesium.

The concentration of the imaging agent or the therapeutic agent in the radiological vehicle should be sufficient to provide satisfactory imaging. For example, when using an aqueous solution, the dosage is about 1.0 to 50 millicuries. The actual dose administered to a patient for imaging or therapeutic purposes, however, is determined by the physician administering treatment. The imaging agent or therapeutic agent should be administered so as to remain in the patient for about 1 to 24 hours, although both longer and shorter time periods are acceptable. Therefore, convenient ampoules containing 1 to 10 mL of aqueous solution may be prepared.

Imaging may be carried out in the normal manner, for example by injecting a sufficient amount of the imaging composition to provide adequate imaging and then scanning with a suitable machine, such as a gamma camera. In certain embodiments, a method of imaging a region in a patient, for example, imaging one or more tissues that express prostate-specific membrane antigen (PSMA) includes the steps of: (i) administering to a patient a diagnostically effective amount of a Formula I, Formula II or Formula III compound complexed with a radionuclide so as to contact the one or more tissues expressing PSMA with a radionuclide complex of a Formula I, Formula II or Formula III compound; and (ii) recording a radiographic image of the one or more tissues. In one embodiment the tissue imaged is a prostate tissue or a prostate cancer tissue. According to the inventive methodology, imaging can be carried out by administering to a patient a diagnostically effective amount of a Formula I compound complexed to a radionuclide, a Formula II compound complexed to a radionuclide or a Formula III compound complexed to a radionuclide, or a pharmaceutically acceptable salt or solvate of the inventive complexes.

In one embodiment, therefore, imaging is carried out using a radionuclide complex of a Formula III compound.

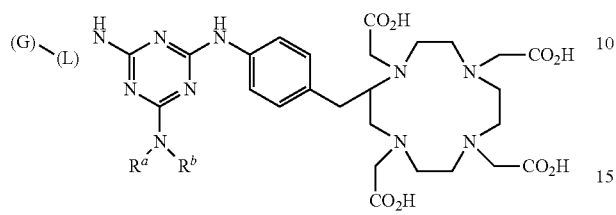

III

In Formula III, G is

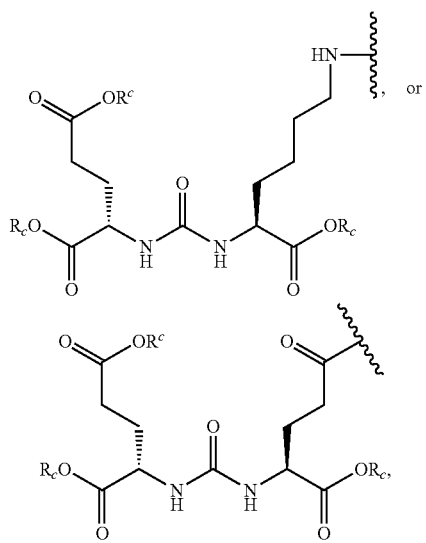

is selected from —NH—$(C_1$-$C_{10})$alkylene-, —NH—$(C_1$-$C_{10})$alkylene-C(O)—, —C(O)—$(C_1$-$C_{10})$alkylene-, —C(O)—$(C_1$-$C_{10})$alkylene-C(O)— or

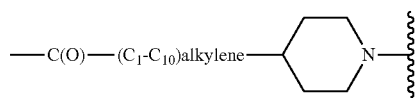

and variables $R^a$ and $R^b$ are each independently selected from the group consisting of H, —OH, —$(C_1$-$C_{10})$alkyl, —[$CH_2$—$CH_2$—O]$_n$—$(CH_2)_2$-T, —C(O)—$(C_1$-$C_{10})$alkyl, —$(C_1$-$C_{10})$alkylene-C(O)—, —$(C_1$-$C_{10})$alkylene-C(O)—Z, benzyl, —$(C_3$-$C_{10})$cycloalkyl, —$(C_3$-$C_{10})$aryl-$(C_1$-$C_{10})$alkylene, —$(C_3$-$C_{10})$aryl, halo-$(C_1$-$C_{10})$alkyl, hydroxy-$(C_1$-$C_{10})$alkyl, —NH—$(C_1$-$C_{10})$alkyl, and —$(C_1$-$C_{10})$alkylene-NR$^d$R$^e$—, or $R^a$ and $R^b$ together with the nitrogen to which they are bonded form a $(C_3$-$C_6)$-heteroaryl or $(C_3$-$C_6)$-heterocycloalkyl that can further comprise one or more heteroatoms selected from N, S, or O.

Z in Formula III is selected from —OH, —O$(C_1$-$C_{10})$alkyl,

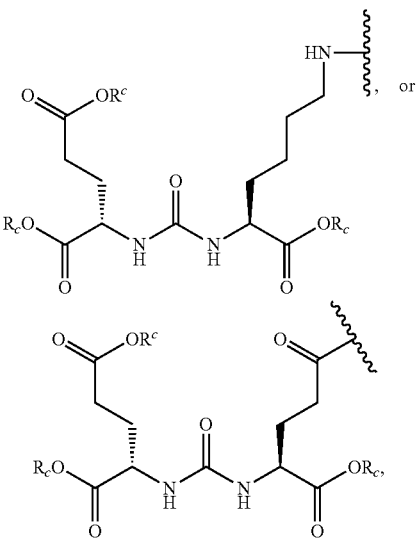

while $R^d$ and $R^e$ are each independently selected from H, bond, —OH, —$(C_1$-$C_{10})$alkyl, or —$(C_3$-$C_{10})$heteroaryl-$(C_1$-$C_{10})$alkylene. Subscript "n" is an integer selected from 0, 1, 2, 3, 4, 5, 6, 7, 8 9, or 10. For Formula III compounds, any alkyl, alkylene, aryl, arylene, heteroaryl, heteroarylene, cycloalkyl, cycloalkylene, heterocycloalkyl, or heterocycloalkylene is optionally substituted with 1, 2, or 3 substituent groups selected from the group consisting of —$(C_1$-$C_{10})$alkyl, —$(C_1$-$C_{10})$haloalkyl, —$(C_1$-$C_{10})$ aminoalkyl, —$(C_1$-$C_{10})$alkylene-COOH, —$(C_1$-$C_{10})$hydroxyalkyl, —$NH_2$, —COOH, —C(O)—$(C_1$-$C_{10})$alkyl, —$(C_1$-$C_{10})$alkylene-C(O)—, —$(C_1$-$C_{10})$alkylene-C(O)—X, —NH—$(C_1$-$C_{10})$alkyl, and —$(C_1$-$C_{10})$alkylene-NR$^d$R$^e$—, and —NR$^d$R$^e$.

The metal used to form the complex is a radionuclide selected from $^{111}$In, $^{90}$Y, $^{68}$Ga, $^{64}$Cu, $^{153}$Gd, $^{155}$Gd, $^{157}$Gd, $^{59}$Fe, $^{225}$Ac, $^{212}$Bi, $^{213}$Bi, $^{55}$Co, $^{67}$Cu, $^{165}$Dy, $^{166}$Ho, $^{192}$Ir, $^{223}$Ra, $^{186}$Re, $^{188}$Re, $^{105}$Rh, $^{212}$Pb, $^{213}$Pb, $^{149}$Tb, $^{227}$Th, $^{153}$Sm, $^{89}$Sr, $^{117m}$Sn, $^{169}$Yb, $^{90}$Y, $^{86}$Y, $^{89}$Zr and $^{177}$Lu.

The amount of a Formula I, Formula II or Formula III compound, or a formulation comprising a complex of a radiometal and a compound according to Formula I or Formula II, or its salt, solvate, stereoisomer, or tautomer that is administered to a patient depends on several physiological factors that are routinely used by the physician, including the nature of imaging to be carried out, tissue to be targeted for imaging and the body weight and medical history of the patient to be imaged.

Also described is a method for treating a patient diagnosed with cancer by administering to such a patient a therapeutically effective amount of a prostate-specific membrane antigen (PSMA) binding complex comprising a triazinylene linker. In one embodiment of this methodology, the prostate-specific membrane antigen (PSMA) binding complex comprising a triazinylene linker is a Formula I, Formula II or Formula III compound complexed to a radionuclide, or a pharmaceutically acceptable salt or solvate of the complex. Radionuclide complexes of Formula I, Formula II and Formula III compounds, as described above, are preferentially retained in PSMA-expressing tumor tissue than non-PSMA expressing tissues such as kidney, liver, spleen, heart, blood, lungs, muscle, bone, large intestine, small intestine, brain, or fat. In addition to prostate cancer, radionuclide complexes of Formula I or Formula II compounds are also candidate therapeutics for treating breast cancer, colon cancer, brain cancer, lung cancer, liver cancer or kidney cancer.

The present invention, thus generally described, will be understood more readily by reference to the following examples, which are provided by way of illustration and are not intended to be limiting of the present invention.

EXAMPLES

General Protocol for Cell Culture

Human prostate cancer LNCaP cells were obtained from the American Type Culture Collection. Cell culture supplies were from Invitrogen unless otherwise noted. LNCaP cells were maintained in RPMI-1640 medium supplemented with 10% fetal bovine serum (Hyclone), 4 mM L-glutamine, 1 mM sodium pyruvate, 10 mM hepes, 2.5 mg/mL D-glucose, and 50 µg/mL gentamicin in a humidified incubator at 37° C./5% $CO_2$. Cells were removed from flasks for passage, inoculation of mice or for transfer to 12-well assay plates by incubating them with 0.25% trypsin/EDTA.

General Protocol for Competitive Binding

The ability of non-radioactive lutetium containing PSMA inhibitors to compete with $^{99m}$Tc-((7S,14S,18S)-7-amino-1-(1-(carboxymethyl)-1H-imidazol-2-yl)-2-((1-(carboxymethyl)-1H-imidazol-2-yl)methyl)-8,16-dioxo-2,9,15,17-tetraazaicosane-14,18,20-tricarboxylic acid) for binding to PSMA in LNCaP cells was examined. LNCaP cells ($4 \times 10^5$ cells/well in 12-well plates in triplicate) were incubated for 1 hour with 3 nM of the $^{99m}$Tc-complex in RPMI medium containing 0.5% BSA in the presence of 1-10,000 nM test compounds. Cells were removed to Eppendorf tubes by gently pipetting, washed twice with RPMI+0.5% BSA and counted.

Mouse Studies

All animal studies were approved by the Institute for Animal Care and Use Committee in accordance with the guidelines set forth by the U.S. Public Health Service *Policy on Humane Care and Use of Laboratory Animals*. Mice were housed under standard conditions in approved facilities with 12 hour light/dark cycles and given food and water ad libitum. Male athymic NCr-nu/nu mice were purchased from Taconic. For inoculation in mice, LNCaP cells were resuspended at $10^7$ cells/ml in a 1:1 mixture of cell culture medium:Matrigel (BD Biosciences). Each mouse was injected in the right flank with 0.25 ml of the cell suspension. Mice were used for tissue distribution studies when the tumors reached approximately 100-400 mm$^3$.

Tissue Distribution

A quantitative analysis of the tissue distribution of $^{177}$Lu-labeled compounds was performed in separate groups of male NCr-nu/nu mice bearing LNCaP cell xenografts. The compounds were administered via the tail vein as a bolus injection (approximately 10 µCi/mouse) in a constant volume of 0.05 mL. The animals (n=5/time point) were euthanized by asphyxiation with carbon dioxide at the indicated time points after injection. Tissues, for example, blood, heart, lungs, liver, spleen, kidneys, stomach, large and small intestines (with contents), testes, skeletal muscle, bone, brain, adipose, and tumor were dissected, excised, weighed wet, and counted in an automated γ-counter. Tissue time-radioactivity levels were expressed as percent injected dose per gram of tissue (% ID/g).

In Vivo Efficacy

Mice bearing LNCaP xenografts having an average volume of ~100-500 mm$^3$, were randomly assigned to a control group or a treatment group (n=10 mice per group). Mice in the control group were administered saline while mice in the test group received 450 µCi/mouse of $^{177}$Lu-complex of the inventive Formula I or Formula II compound. Each animal was administered the test article intravenously in a volume of 0.05 mL. Tumor dimensions were measured twice weekly with digital calipers and tumor volumes were calculated using the formula $(4/3 \times \Pi \times width^2 \times length)/6$. Measurements were made until tumor volumes in the vehicle group reached the maximum allowed by IACUC guidelines (1,500 mm$^3$).

General Synthetic Methods.

General procedure for the synthesis of Formula I compounds and for complexation of a Formula I compound with a radionuclide are described. While a protocol for complexing lutetium to a Formula I compound is exemplified below, it is to be understood that a similar synthetic procedure can be followed for complexing other radionuclides. Therefore, while lutetium may specifically be shown in various examples described below, complexes with other radionuclides such as In, Y, Zr, Ga, Lu, Cu, Gd, Ac Fe, Bi Co, Dy Ho, Ir, Ra, Re, Rh, Sr or Sm are within the scope of the present invention. Additionally, it is to be understood that various isotopes of these elements may be complexed for example $^{111}$In, $^{90}$Y, $^{68}$Ga, $^{64}$Cu, $^{153}$Gd, $^{155}$Gd, $^{157}$Gd, $^{59}$Fe, $^{225}$Ac, $^{212}$Bi, $^{213}$Bi, $^{55}$Co, $^{67}$Cu, $^{165}$Dy, $^{166}$Ho, $^{192}$Ir, $^{223}$Ra, $^{186}$Re, $^{188}$Re, $^{105}$Rh, $^{212}$Pb, $^{213}$Pb, $^{149}$Tb, $^{227}$Th, $^{153}$Sm, $^{89}$Sr, $^{117m}$Sn, $^{169}$Yb, $^{90}$Y, $^{86}$Y, $^{89}$Zr and $^{177}$Lu.

General Experimental Conditions for the Formation of the lutetium Complexes

The lutetium complexes of Formula I compounds were conveniently isolated from the reactions that involve contacting commercially available $LuCl_3$ with a compound according to Formula I. Briefly, a $10^{-6}$ M-$10^{-4}$ M solution of the desired Formula I or Formula II compound in an equal volume mixture of 1:1 acetonitrile and phosphate buffer was contacted with $LuCl_3$ in a sealed vial. The reaction mixture was heated at 100° C. for 30 to 45 minutes. Upon cooling, the reaction was analyzed for completion and purity by reverse-phase high pressure liquid chromatography (RP-HPLC) and if required was purified using RP-HPLC or a C18 Sep Pak column. The overall average yield of the lutetium complexed product following purification was in the range from about 20% to about 99%. The radiochemical purity (RCP), after HPLC purification, however, was consistently≥95%.

Initial results demonstrated radiolabeling of a Formula I or a Formula II compound at concentrations as low as $10^{-6}$ M, the radiochemical yield (RCY) at this concentration of reagents was approximately ≤80%. To achieve a higher RCY, greater than 95%, the reaction temperature and concentration of reagents in the reaction mixture were increased to $10^{-4}$ M.

A similar synthetic strategy was used to incorporate other radionuclides. Moreover, the introduction of a radionuclide can be made either prior to deprotection of a Formula I or Formula II compound, or after deprotecting a Formula I compound.

Synthesis of Exemplary Triazine-Piperazine Based Formula I, Formula II, or Formula III Compounds Schemes A, B and C illustrate general synthetic protocols for exemplary Formula I compounds. Briefly, p-aminobenzyl DOTA is contacted with cyanuric chloride followed by reaction of the resultant product with an amine. The product thus formed is then contacted with a GUG- or GUL-linker-piperazine moiety to obtain a Formula I compound.

Scheme A.
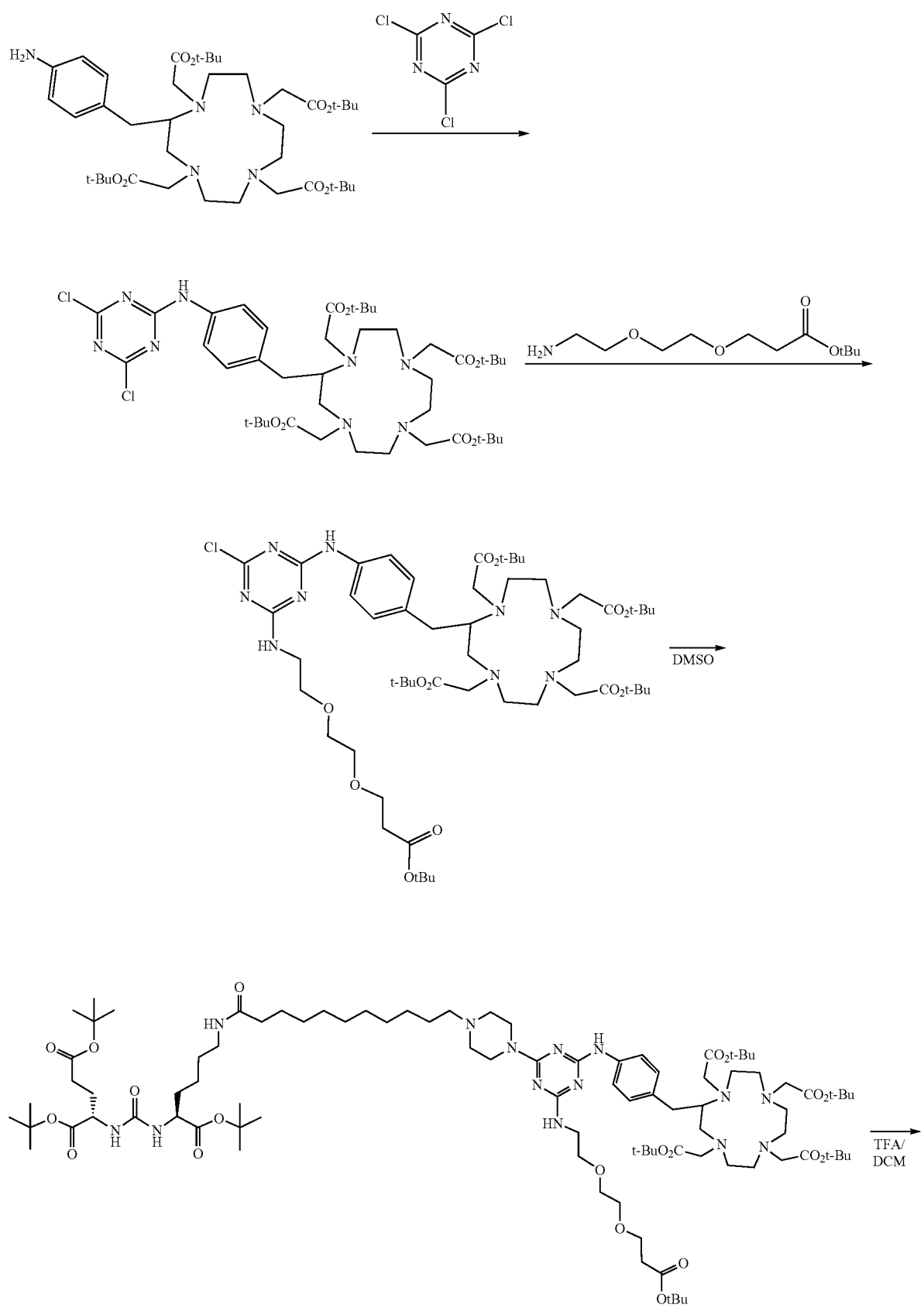

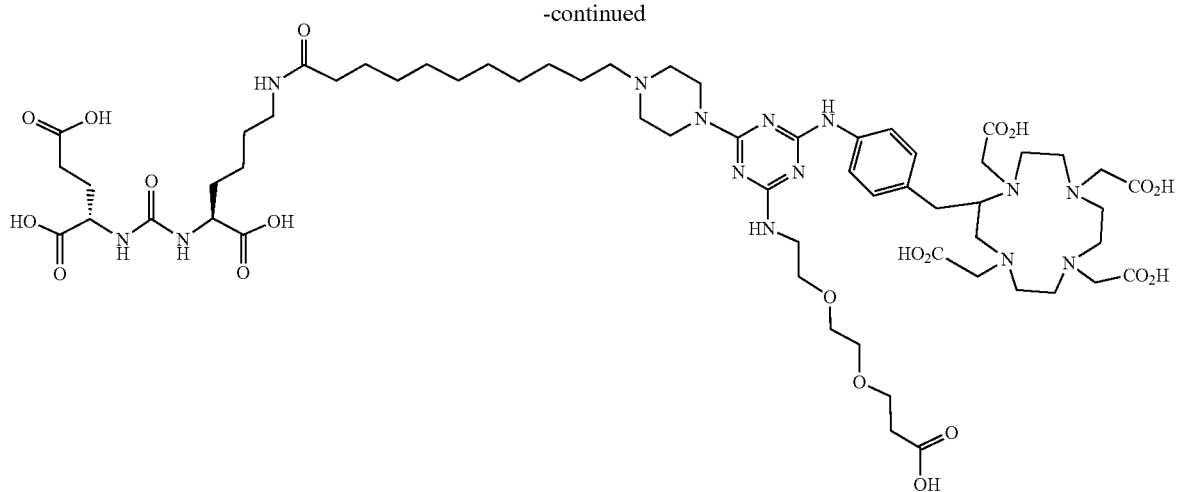
-continued
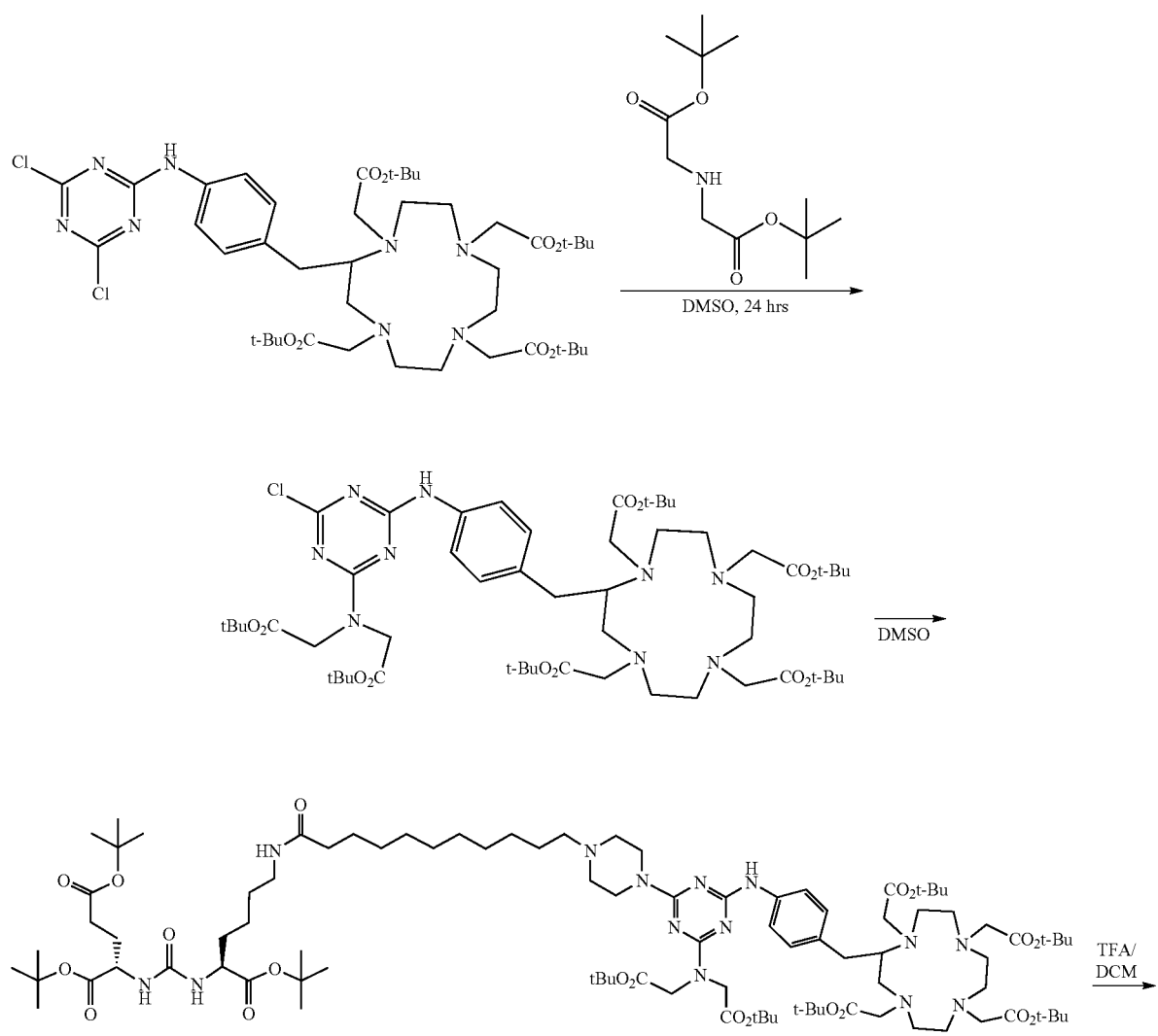
Scheme B

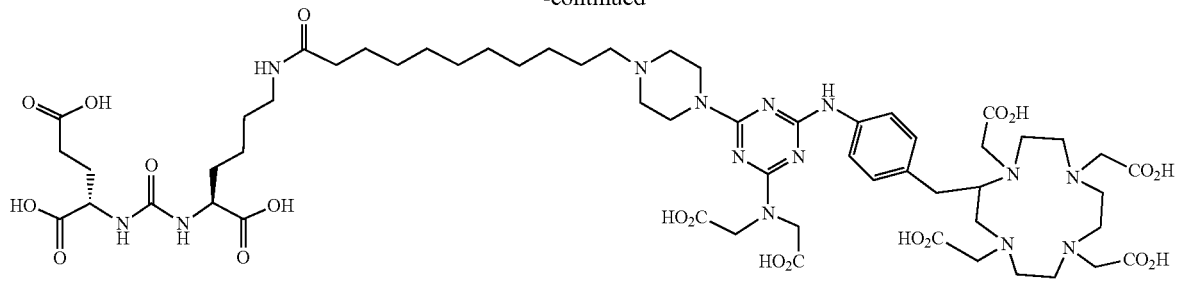
Scheme C
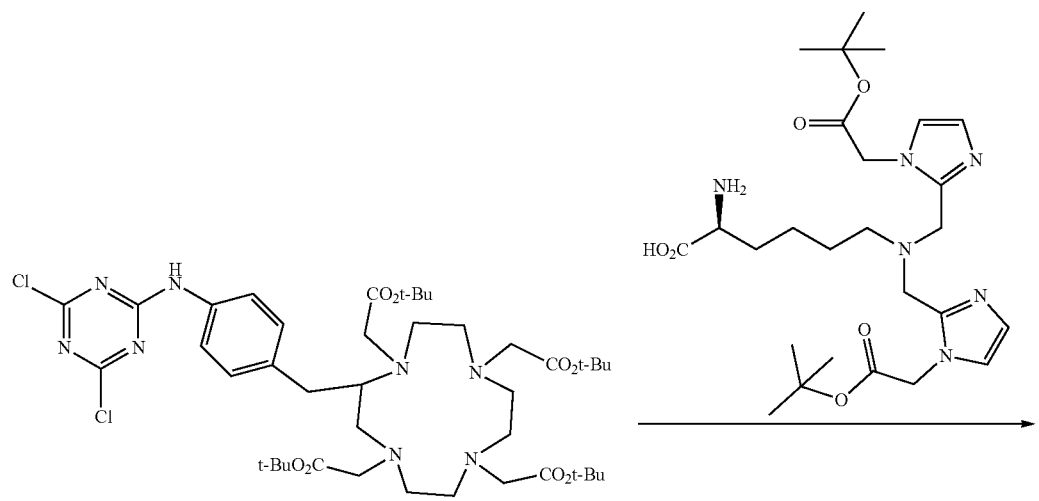
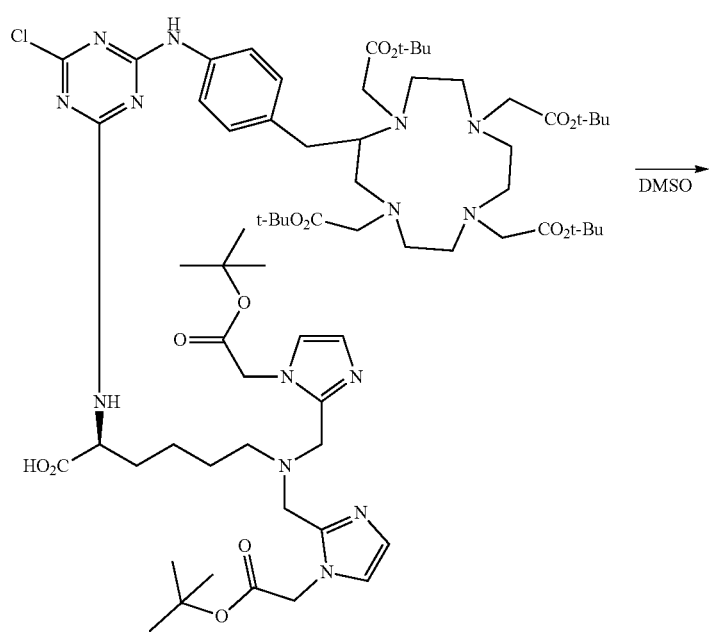

-continued
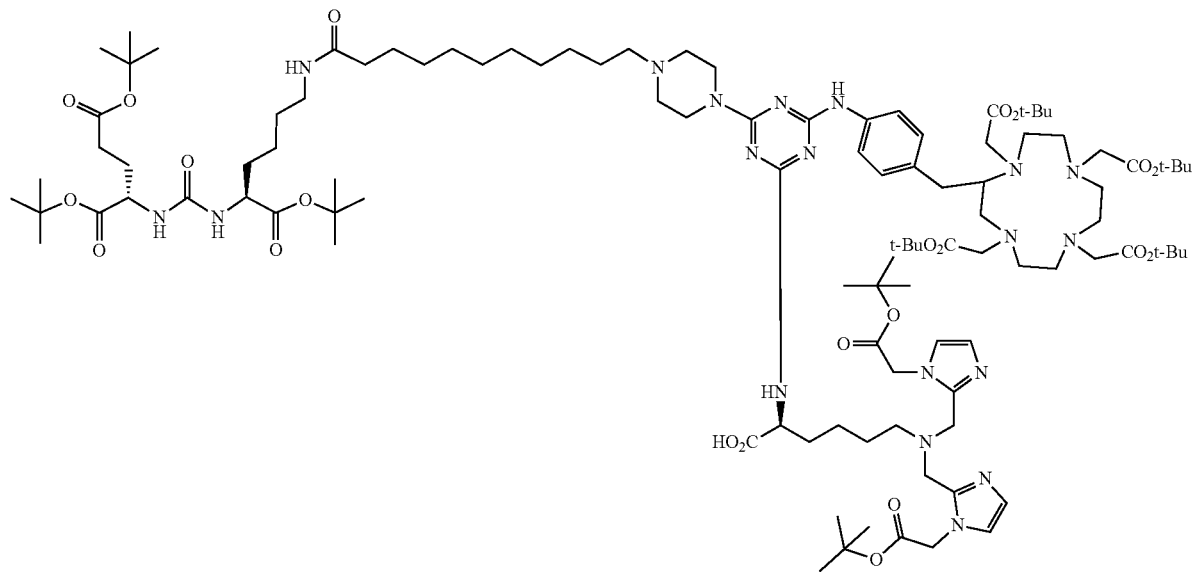
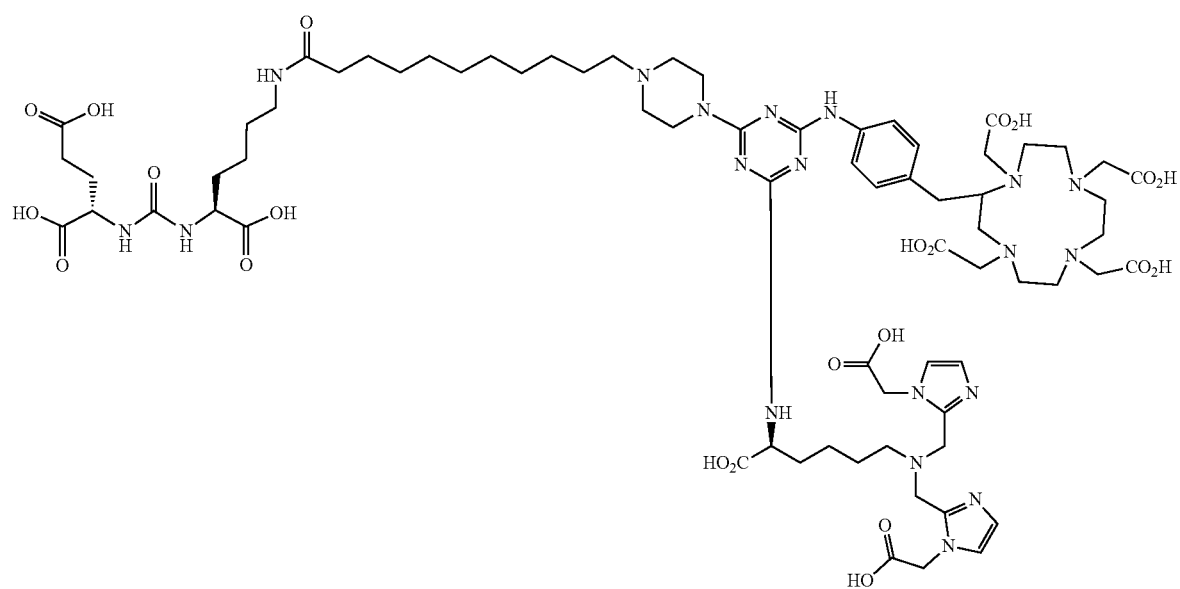

Example 1: (2S)-2-(3-((1S)-1-carboxy-5-(8-((4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl)amino)octanamido)pentyl)ureido) pentanedioic Acid Lutetium Complex

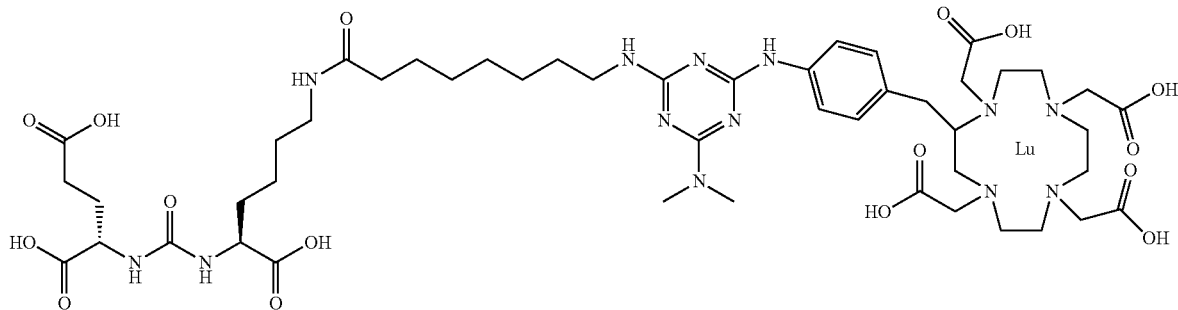

Step 1. (18S,22S)-tri-tert-butyl 1-(9H-fluoren-9-yl)-3,12,20-trioxo-2-oxa-4,13,19,21-tetraazatetracosane-18,22,24-tricarboxylate

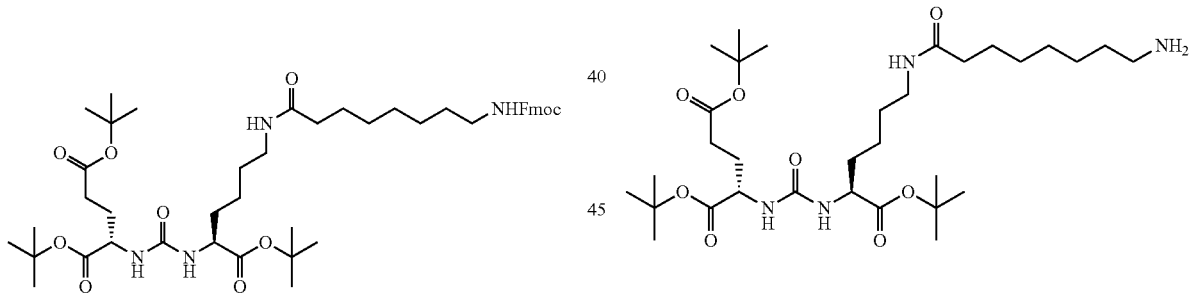

A solution of (S)-di-tert-butyl 2-(3-((S)-6-amino-1-(tert-butoxy)-1-oxohexan-2-yl)ureido)pentanedioate (1.9677 g, 4.03 mmol), 8-((((9H-fluoren-9-yl)methoxy)carbonyl)amino)octanoic acid (1.84 g, 4.84 mmol), 1-ethyl-3-(3-dimethylaminopropyl)carbodiimide) (EDCI; (0.770 g, 4.03 mmol), HOBt (0.544 g, 4.03 mmol) and N,N-diisopropylethylamine (DIPEA; (2.0 mL)) in DCE (100 mL) was stirred at room temperature for overnight. The solvent was evaporated to give a residue, which was purified by silica gel column chromatography (Biotage) using a mixture of DCM/MeOH as the eluent to give (18S,22S)-tri-tert-butyl 1-(9H-fluoren-9-yl)-3,12,20-trioxo-2-oxa-4,13,19,21-tetraazatetracosane-18,22,24-tricarboxylate (2.099 g, 61%) as a white solid. MS (ESI), 851.2 (M+H)$^+$.

Step 2. (S)-di-tert-butyl 2-(3-((S)-6-(8-aminooctanamido)-1-(tert-butoxy)-1-oxohexan-2-yl)ureido)pentanedioate To a solution of (18S,22S)-tri-tert-butyl 1-(9H-fluoren-9-yl)-3,12,20-trioxo-2-oxa-4,13,19,21-tetraazatetracosane-18,22,24-tricarboxylate (1.983 mg, 2.333 mmol) in DMF (4.0 mL) was added piperidine (4.0 mL). The mixture was stirred at room temperature for 3 hrs following which the solvent was evaporated under reduce pressure to afford a residue, which was purified by column chromatography using a Biotage SP4 column and gradient elution using 100% DCM to a 1:1 mixture of DCM:methanol as the eluting solvent. The product (S)-di-tert-butyl-2-(3-((S)-6-(8-aminooctanamido)-1-(tert-butoxy)-1-oxohexan-2-yl)ureido)pentanedioate (1.039 mg, 71%), thus obtained was characterized using $^1$H NMR and mass spectrometry. $^1$H NMR (400 MHz, DMSO-d$_6$) 7.71 (t, J=5.2 Hz, 1H), 6.29 (d, J=8.0 Hz, 1H), 6.25 (d, J=8.4 Hz, 1H), 5.74 (brs, 2H), 4.05-3.91 (m, 2H), 3.01-2.88 (m, 2H), 2.63 (t, J=6.8 Hz, 2H), 2.20-1.22 (m, 49H); MS (ESI), 629.3 (M+H)$^+$.

Step 3. (2S)-2-(3-((1S)-1-carboxy-5-(8-(4-(dimethylamino)-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic Acid

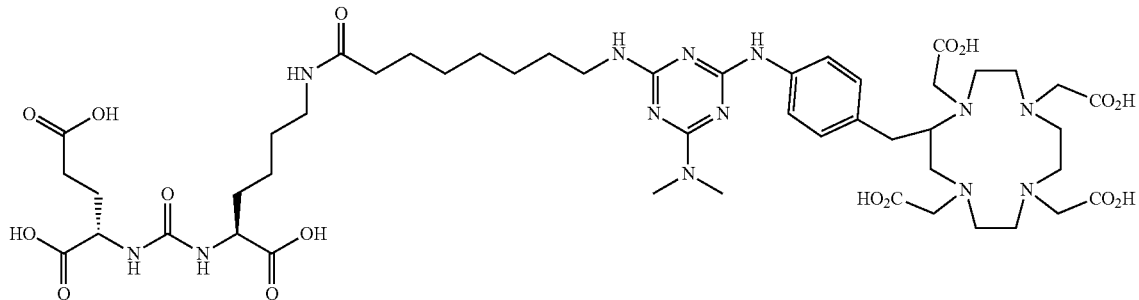 [SMILES: CN(C)c1nc(NCCCCCCCC(=O)NCCCC[C@H](NC(=O)N[C@@H](CCC(=O)O)C(=O)O)C(=O)O)nc(Nc2ccc(CC3CN(CC(=O)O)CCN(CC(=O)O)CCN(CC(=O)O)CCN3CC(=O)O)cc2)n1]

To a solution of p-NH2-Bn-DOTA-tetra(t-Bu-ester) (67.8 mg, 0.080 mmol) and cyanuric chloride (14.7 mg, 0.080 mmol) in DCM (4.0 mL) was added DIPEA (0.10 mL). This solution was stirred at room temperature for 3 hrs, following which the solvent was removed under a stream of nitrogen to give a residue. To a DMSO (4.0 mL) solution of the residue was added (S)-di-tert-butyl 2-(3-((S)-6-(8-aminooctanamido)-1-(tert-butoxy)-1-oxohexan-2-yl)ureido)pentanedioate (50.3 mg, 0.08 mmol) and $K_2CO_3$ (100 mg). The suspension was stirred at room temperature for about 2 hrs and then a tetrahydrofuran solution of dimethylamine (0.3 mL, 2.0 M in THF) was added to the reaction mixture. After stirring at room temperature continuously for 16 hrs, the reaction mixture was lyophilized to afford the crude triazine intermediate. The crude product was deprotected by the addition of TFA (4.0 mL) and DCM (1.0 mL) and stirring the reaction mixture at room temperature for 4 hours. Removal of the solvent using a stream of nitrogen gas gave a residue, which was purified using Biotage SP4 via C18 cartridge to give (2S)-2-(3-((1S)-1-carboxy-5-(8-(4-(dimethylamino)-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic acid (67 mg) as a white solid. $^1$H NMR (400 MHz, DMSO-$d_6$) □7.83-7.60 (m, 3H), 7.17 (d, J=8.0 Hz, 2H), 6.32 (d, J=8.0 Hz, 1H), 6.28 (d, J=8.4 Hz, 1H), 4.10-1.27 (m, 61H); MS (ESI), 1091.4 (M+H)$^+$.

Step 4. (2S)-2-(3-((1S)-1-carboxy-5-(8-(4-(dimethylamino)-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic Acid Lutetium Complex To solid (2S)-2-(3-((1S)-1-carboxy-5-(8-(4-(dimethylamino)-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic acid (5.7 mg, 0.00522 mmol) was added $LuCl_3$ (1.46 mL of a 0.00357 mmol/mL, 0.00522 mmol) and acetonitrile (0.50 mL). The reaction mixture was heated at 95° C. for 1 hour and then lyophilized to give (2S)-2-(3-((1 S)-1-carboxy-5-(8-(4-(dimethylamino)-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic acid lutetium complex (6.2 mg) as a white solid. MS (ESI), 1263.0 (M+H)$^+$.

Example 2. (S)-2-(3-((S)-1-Carboxy-5-(8-((4-(piperidin-1-yl)-6-((4-(((S)-1,4,7,10-tetrakis(carboxymethyl)-1,4,7,10-tetraazacyclododecan-2-yl)methyl)phenyl)amino)-1,3,5-triazin-2-yl)amino)octanamido)pentyl)ureido)pentanedioic Acid Lutetium Complex

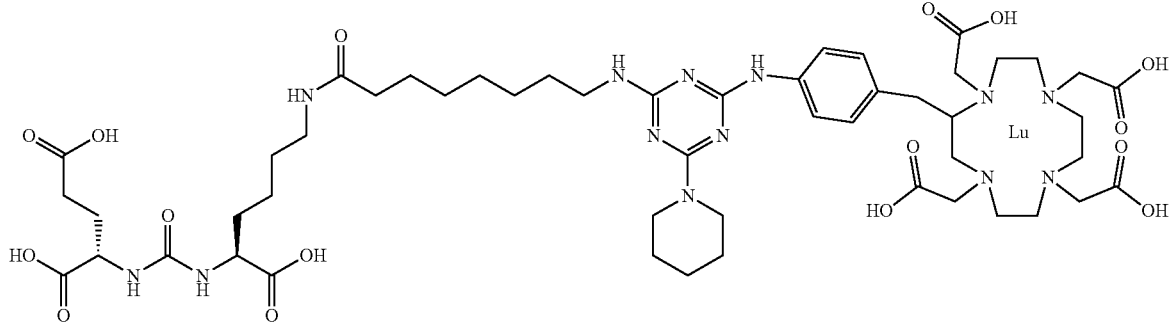

Step 1. (2S)-2-(3-((S)-1-carboxy-5-(8-(4-(piperidin-1-yl)-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido) pentanedioic Acid

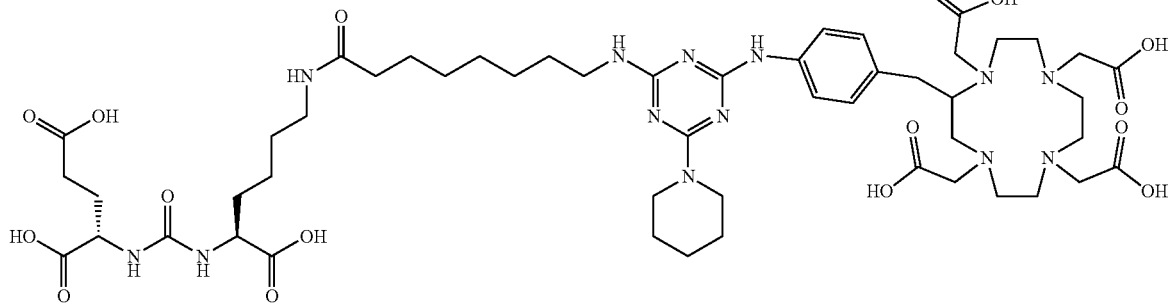

To a solution of p-NH2-Bn-DOTA-tetra(t-Bu-ester) (Macrocyclics) (42.4 mg, 0.050 mmol) and cyanuric chloride (9.2 mg, 0.050 mmol) in DCM (2.0 mL) was added DIPEA (0.10 mL). This reaction mixture was stirred at room temperature for 2 hours following which the solvent was removed using a stream of nitrogen to give a residue. The residue thus obtained was dissolved in DMSO (4.0 mL) and (S)-di-tert-butyl 2-(3-((S)-6-(8-aminooctanamido)-1-(tert-butoxy)-1-oxohexan-2-yl)ureido)pentanedioate (31.4 mg, 0.05 mmol) and $K_2CO_3$ (100 mg) were added. The suspension was stirred at room temperature for 2 hrs and then piperidine (0.10 mL) was added. The reaction mixture was stirred at room temperature for an additional 14 hrs and then lyophilized to afford a triazine intermediate, which was deprotected by the addition of TFA (2.0 mL) in DCM (1.0 mL). Deprotection was carried out by stirring the reaction mixture at room temperature for 4 hours. Following deprotection, the solvent was removed using a stream of nitrogen to give a residue, which was purified by Biotage SP4 using C18 cartridge to give pure (2S)-2-(3-((S)-1-carboxy-5-(8-(4-(piperidin-1-yl)-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido) pentanedioic acid (25.8 mg) as a white solid. $^1$H NMR (400 MHz, DMSO-$d_6$) 7.75-7.60 (m, 3H), 7.18 (d, J=7.2 Hz, 2H), 6.33 (d, J=7.6 Hz, 1H), 6.30 (d, J=8.0 Hz, 1H), 4.12-1.24 (m, 65H); MS (ESI), 1131.2 (M+H)$^+$.

Step 2. (2S)-2-(3-((S)-1-carboxy-5-(8-(4-(piperidin-1-yl)-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido) pentanedioic Acid Lutetium Complex To solid (2S)-2-(3-((S)-1-carboxy-5-(8-(4-(piperidin-1-yl)-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic acid (9.2 mg, 0.00814 mmol) was added $LuCl_3$ (1.60 mL, of a 0.00513 mmol/mL, 0.0082 mmol) and acetonitrile (0.50 mL). The reaction mixture was heated at 95° C. for 1 hour and then lyophilized to give (2S)-2-(3-((S)-1-carboxy-5-(8-(4-(piperidin-1-yl)-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl) ureido) pentanedioic acid lutetium complex (9.4 mg) as a white solid. MS (ESI), 1302.2 (M+H)$^+$.

Example 3. (2S)-2-(3-((1S)-1-carboxy-5-(8-(4-morpholino-6-(4-((1,4,7,10-tetrakis(carboxymethyl)-1,4,7,10-tetraazacyclododecan-2-yl)methyl)phenylamino)-1,3,5-triazin-2-ylamino)octanamido) pentyl)ureido)pentanedioic Acid Lutetium Complex

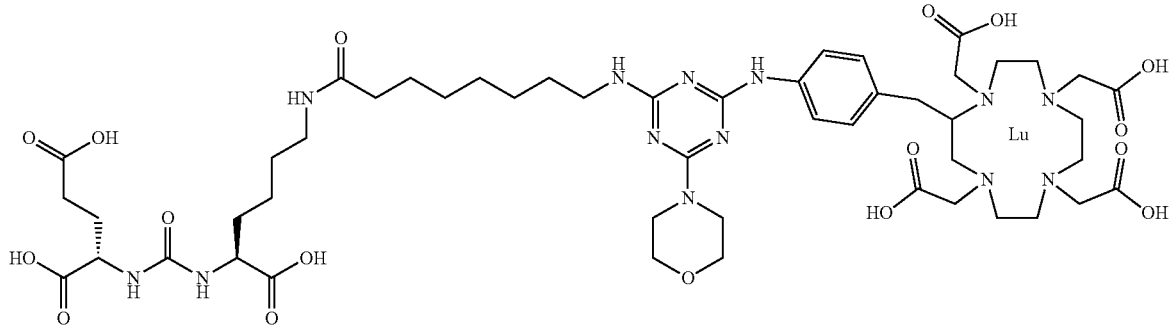

Step 1. (2S)-2-(3-((1S)-1-carboxy-5-(8-(4-morpholino-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic Acid

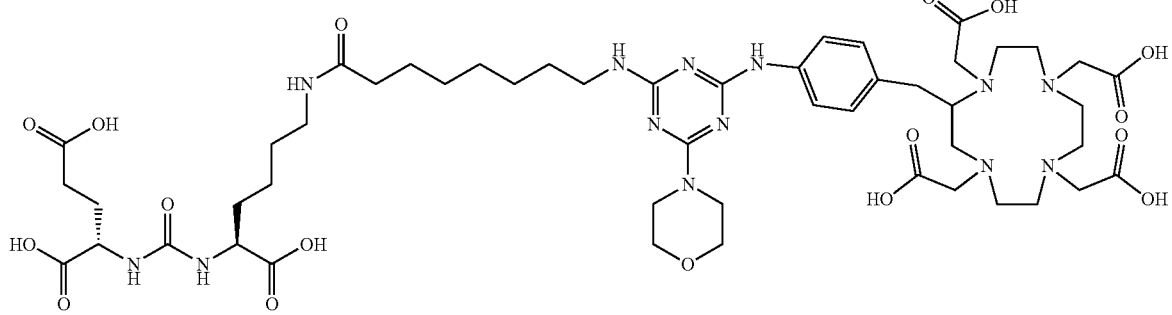

To a solution of p-NH2-Bn-DOTA-tetra(t-Bu-ester) (Macrocyclics) (42.4 mg, 0.050 mmol) and cyanuric chloride (9.2 mg, 0.050 mmol) in DCM (2.0 mL) was added DIPEA (0.10 mL). The reaction was stirred at room temperature for 2 hours and the solvent was then removed using a stream of nitrogen to give a residue. The residue was dissolved in DMSO (4.0 mL) and (S)-di-tert-butyl 2-(3-((S)-6-(8-aminooctanamido)-1-(tert-butoxy)-1-oxohexan-2-yl)ureido)pentanedioate (31.4 mg, 0.05 mmol) and $K_2CO_3$ (100 mg) were then added to the DMSO solution. The suspension was stirred at room temperature for 2 hours following which morpholine (0.10 mL) was added and the reaction mixture was stirred at room temperature for an additional 14 hours. The reaction mixture was lyophilized to afford a triazine intermediate to which was added TFA (2.0 mL) and DCM (1.0 mL). This mixture was stirred at room temperature for 4 hours to effect deprotection following which the solvent was removed using a stream of nitrogen to give a residue of the crude product. Purification was effected using a Biotage SP4 and a C18 cartridge to give (2S)-2-(3-((1S)-1-carboxy-5-(8-(4-morpholino-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic acid (29.8 mg) as a white solid. $^1$H NMR (400 MHz, DMSO-$d_6$) 7.75-7.65 (m, 3H), 7.14 (m, 2H), 6.55 (m, 2H), 6.33 (d, J=8.0 Hz, 1H), 6.30 (d, J=8.4 Hz, 1H), 4.10-1.27 (m, 61H); MS (ESI), 1133.2 (M+H)$^+$.

Step 2. (2S)-2-(3-((1S)-1-carboxy-5-(8-(4-morpholino-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic Acid Lutetium Complex To solid (2S)-2-(3-((1S)-1-carboxy-5-(8-(4-morpholino-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic acid (10.4 mg, 0.0092 mmol) was added $LuCl_3$ (1.80 mL, 0.00513 mmol/mL, 0.0092 mmol) and acetonitrile (0.50 mL). The reaction mixture was heated at 95° C. for 1 hour and then lyophilized to to give (2S)-2-(3-((1S)-1-carboxy-5-(8-(4-morpholino-6-(4-((1,4,7,10-tetrakis(carboxymethyl)-1,4,7,10-tetraazacyclododecan-2-yl)methyl)phenylamino)-1,3,5-triazin-2-ylamino)octanamido)pentyl)ureido)pentanedioic acid lutetium complex (9.9 mg) as a white solid. MS (ESI), 1304.9 (M+H)$^+$.

Example 4. (2S)-2-(3-((1S)-1-carboxy-5-(8-(4-(4-((4-carboxy-1,7,10-tris(carboxymethyl)-1,4,7,10-tetraazacyclododecan-2-yl)methyl)phenylamino)-6-(piperazin-1-yl)-1,3,5-triazin-2-ylamino)octanamido)pentyl)ureido)pentanedioic Acid Lutetium Complex

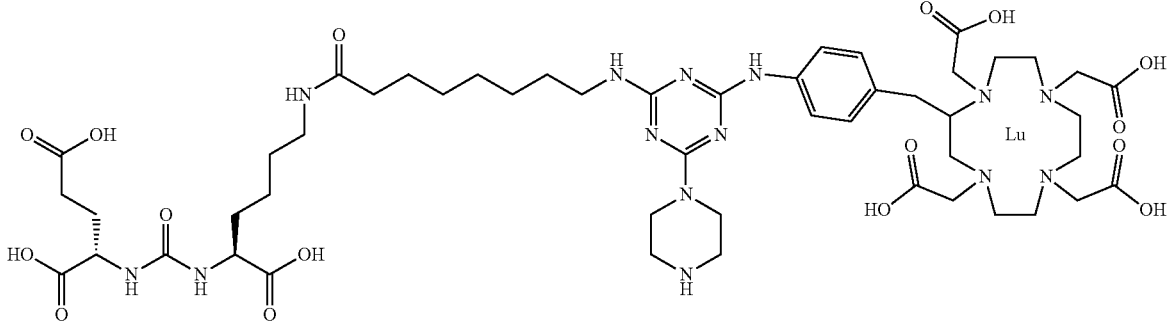

Step 1. (2S)-2-(3-((1S)-1-carboxy-5-(8-(4-(4-((4-carboxy-1,7,10-tris(carboxymethyl)-1,4,7,10-tetraazacyclododecan-2-yl)methyl)phenylamino)-6-(piperazin-1-yl)-1,3,5-triazin-2-ylamino)octanamido)pentyl)ureido)pentanedioic Acid

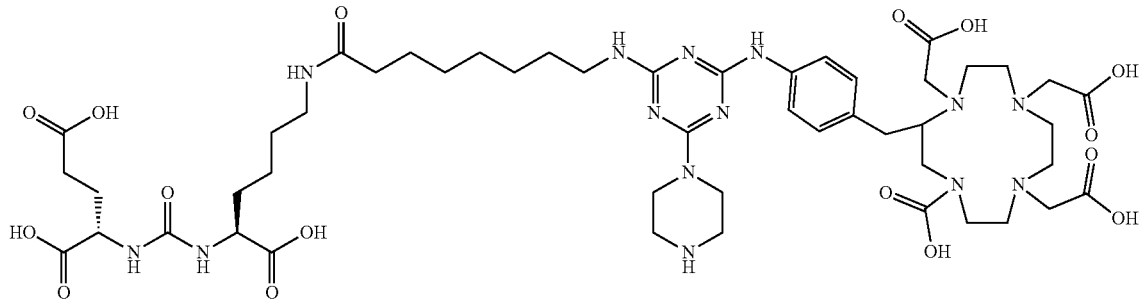 [SMILES: O=C(O)CC[C@H](NC(=O)N[C@@H](CCCCNC(=O)CCCCCCCNc1nc(Nc2ccc(CC3CN(C(=O)O)CCN(CC(=O)O)CCN(CC(=O)O)CCN3CC(=O)O)cc2)nc(N2CCNCC2)n1)C(=O)O)C(=O)O]

To a solution of p-NH2-Bn-DOTA-tetra(t-Bu-ester) (Macrocyclics) (42.4 mg, 0.050 mmol) and cyanuric chloride (9.2 mg, 0.050 mmol) in DCM (2.0 mL) was added DIPEA (0.10 mL). The reaction was stirred at room temperature for 2 hrs. The solvent was then removed using a stream of nitrogen to give a residue, which was dissolved in DMSO (4.0 mL) and (S)-di-tert-butyl 2-(3-((S)-6-(8-aminooctanamido)-1-(tert-butoxy)-1-oxohexan-2-yl)ureido)pentanedioate (31.43 mg, 0.05 mmol) and K$_2$CO$_3$ (100 mg) were then added to the DMSO solution. The resultant suspension was stirred at room temperature for 2 hrs following which piperazine (100 mg) was added and stirring was continued at room temperature for an additional 16 hrs. The crude reaction was then lyophilized and the triazine intermediate thus obtained was added deprotected using TFA (2.0 mL) and DCM (1.0 mL). Deprotection was carried out by stirring the mixture at room temperature overnight, following which the solvent was removed using a stream of nitrogen to give a residue of the crude product which was purified by Biotage SP4 using a C18 cartridge to give (2S)-2-(3-((1S)-1-carboxy-5-(8-(4-(4-((4-carboxy-1,7,10-tris(carboxymethyl)-1,4,7,10-tetraazacyclododecan-2-yl)methyl)phenylamino)-6-(piperazin-1-yl)-1,3,5-triazin-2-ylamino)octanamido)pentyl)ureido)pentanedioic acid (18.9 mg) as a white solid. $^1$H NMR (400 MHz, DMSO-d$_6$) 8.85 (m, 2H), 7.75-7.65 (m, 4H), 7.16 (m, 2H), 6.55 (m, 2H), 6.32 (d, J=8.8 Hz, 1H), 6.29 (d, J=8.4 Hz, 1H), 4.11-1.23 (m, 61H); MS (ESI), 1132.2 (M+H)$^+$.

Step 2. (2S)-2-(3-((1S)-1-carboxy-5-(8-(4-(4-((4-carboxy-1,7,10-tris(carboxymethyl)-1,4,7,10-tetraazacyclododecan-2-yl)methyl)phenylamino)-6-(piperazin-1-yl)-1,3,5-triazin-2-ylamino)octanamido)pentyl)ureido)pentanedioic Acid Lutetium Complex To solid (2S)-2-(3-((1S)-1-carboxy-5-(8-(4-(4-((4-carboxy-1,7,10-tris(carboxymethyl)-1,4,7,10-tetraazacyclododecan-2-yl)methyl)phenylamino)-6-(piperazin-1-yl)-1,3,5-triazin-2-ylamino)octanamido)pentyl)ureido)pentanedioic acid (7.8 mg, 0.0069 mmol) was added LuCl$_3$ (1.80 mL of a 0.00385 mmol/mL, 0.0069 mmol and acetonitrile (0.5 mL). The reaction mixture was heated at 95° C. for 1 hour and then lyophilized to give (2S)-2-(3-((1S)-1-carboxy-5-(8-(4-(4-((4-carboxy-1,7,10-tris(carboxymethyl)-1,4,7,10-tetraazacyclododecan-2-yl)methyl)phenylamino)-6-(piperazin-1-yl)-1,3,5-triazin-2-ylamino)octanamido)pentyl) ureido)pentanedioic acid lutetium complex (8.3 mg) as a white solid. MS (ESI), 1303.6 (M+H)$^+$.

Example 5. (2S)-2-(3-((1S)-1-carboxy-5-(8-(4-(4-(3-carboxypropyl)piperidin-1-yl)-6-(4-((1,4,7,10-tetrakis(carboxymethyl)-1,4,7,10-tetraazacyclododecan-2-yl)methyl)phenylamino)-1,3,5-triazin-2-ylamino) octanamido) pentyl)ureido)pentanedioic Acid Lutetium Complex

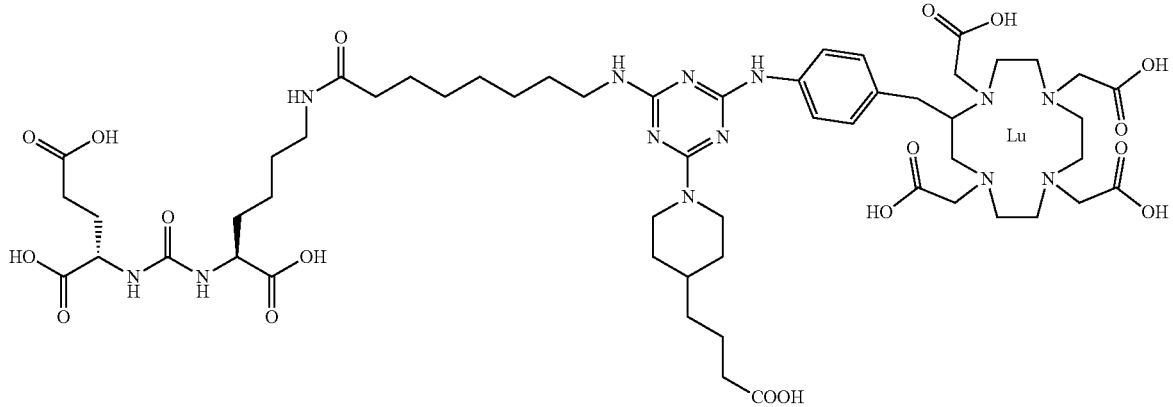

Step 1. (2S)-2-(3-((1S)-1-carboxy-5-(8-(4-(4-(3-carboxypropyl)piperidin-1-yl)-6-(4-((1,4,7,10-tetrakis(carboxymethyl)-1,4,7,10-tetraazacyclododecan-2-yl)methyl)phenylamino)-1,3,5-triazin-2-ylamino) octanamido) pentyl)ureido)pentanedioic Acid

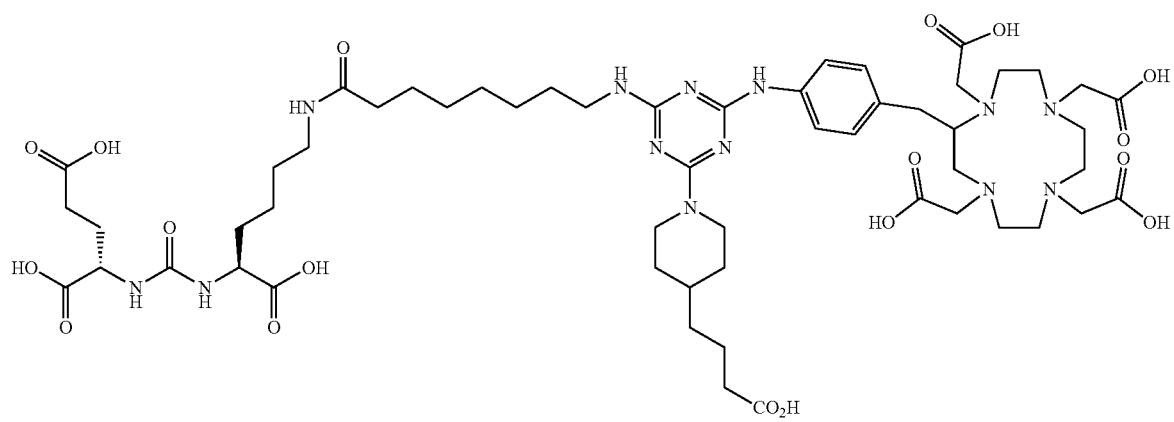 [SMILES: O=C(O)CCCC1CCN(c2nc(NCCCCCCCC(=O)NCCCC[C@H](NC(=O)N[C@@H](CCC(=O)O)C(=O)O)C(=O)O)nc(Nc3ccc(CC4CN(CC(=O)O)CCN(CC(=O)O)CCN(CC(=O)O)CCN4CC(=O)O)cc3)n2)CC1]

DIPEA (0.10 mL) was added to a solution of p-NH2-Bn-DOTA-tetra(t-Bu-ester) (Macrocyclics) (42.4 mg, 0.050 mmol) and cyanuric chloride (9.2 mg, 0.050 mmol) in DCM (2.0 mL) and mixture was stirred at room temperature for 2 hrs. The solvent was then removed using a stream of nitrogen to give a residue, which was dissolved in DMSO (4.0 mL). (S)-di-tert-butyl 2-(3-((S)-6-(8-aminooctanamido)-1-(tert-butoxy)-1-oxohexan-2-yl)ureido)pentanedioate (31.43 mg, 0.05 mmol) and K₂CO₃ (100 mg) were added to the DMSO solution and the resultant suspension was stirred at room temperature for 2 hrs following which 4-(piperidin-4-yl)butanoic acid (30 mg) was added. After stirring at room temperature for an additional 16 hours the reaction mixture was lyophilized to afford a triazine intermediate which was deprotected using TFA (2.0 mL) and DCM (1.0 mL). After stirring at room temperature overnight the solvent was removed using a stream of nitrogen to give a residue of the titled crude. Purification was effected using Biotage SP4 and a C18 cartridge to obtain (2S)-2-(3-((1S)-1-carboxy-5-(8-(4-(4-(3-carboxypropyl)piperidin-1-yl)-6-(4-((1,4,7,10-tetrakis(carboxymethyl)-1,4,7,10-tetraazacyclododecan-2-yl)methyl)phenylamino)-1,3,5-triazin-2-ylamino)octanamido) pentyl)ureido)pentanedioic acid (18.8 mg) as a white solid. MS (ESI), 608.8 (M/2+H)⁺.

Step 2. (2S)-2-(3-((1S)-1-carboxy-5-(8-(4-(4-(3-carboxypropyl)piperidin-1-yl)-6-(4-((1,4,7,10-tetrakis(carboxymethyl)-1,4,7,10-tetraazacyclododecan-2-yl)methyl)phenylamino)-1,3,5-triazin-2-ylamino) octanamido) pentyl)ureido)pentanedioic Acid Lutetium Complex To solid (2S)-2-(3-((1S)-1-carboxy-5-(8-(4-(4-(3-carboxypropyl)piperidin-1-yl)-6-(4-((1,4,7,10-tetrakis(carboxymethyl)-1,4,7,10-tetraazacyclododecan-2-yl)methyl) phenylamino)-1,3,5-triazin-2-ylamino)octanamido) pentyl) ureido)pentanedioic acid (7.4 mg, 0.006086 mmol) was added LuCl₃ (1.58 mL of a 0.00385 mmol/mL, 0.006086 mmol). The reaction mixture was heated at 95° C. for 1 hour and then lyophilized to give (2S)-2-(3-((1S)-1-carboxy-5-(8-(4-(4-(3-carboxypropyl)piperidin-1-yl)-6-(4-((1,4,7,10-tetrakis(carboxymethyl)-1,4,7,10-tetraazacyclododecan-2-yl)methyl)phenylamino)-1,3,5-triazin-2-ylamino) octanamido) pentyl)ureido)pentanedioic acid lutetium complex (9.0 mg) as a white solid. MS (ESI), 1388.8 (M+H)⁺.

Example 6. ((2S,2'S)-2,2'-(((((1S,1'S)-((8,8'-((6-((4-((1,4,7,10-tetrakis(carboxymethyl)-1,4,7,10-tetraaza-cyclododecan-2-yl)methyl)phenyl)amino)-1,3,5-triazine-2,4-diyl)bis(azanediyl))bis(octanoyl))bis(azanediyl))bis(1-carboxypentane-5,1-diyl))bis(azanediyl))bis(carbonyl))bis(azanediyl)) dipentanedioic Acid Lutetium Complex

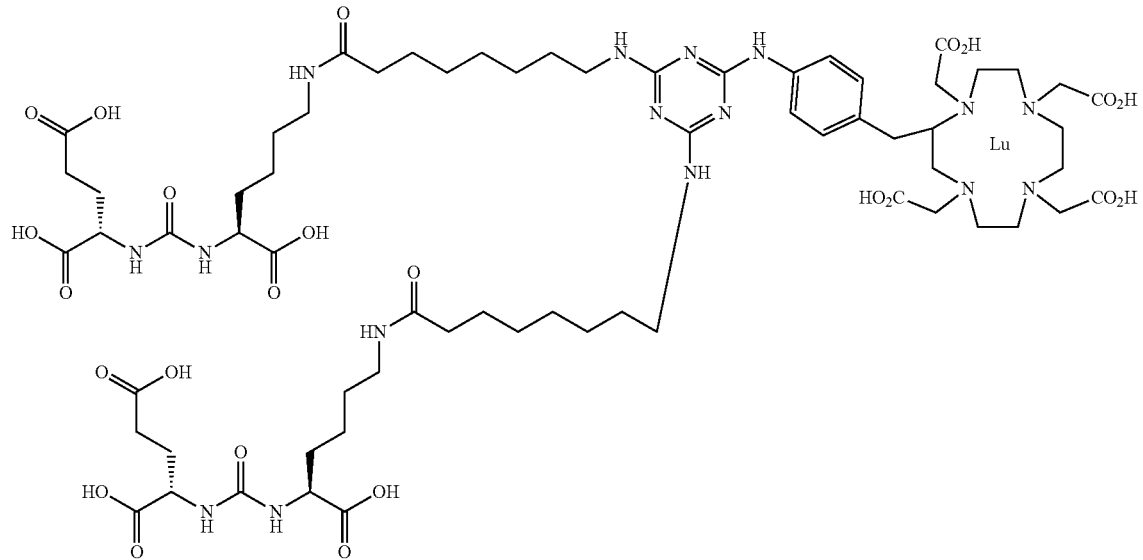

Step 1. ((2S,2'S)-2,2'-(((((1S,1'S)-((8,8'-((6-((4-((1,4,7,10-tetrakis(carboxymethyl)-1,4,7,10-tetraazacyclododecan-2-yl)methyl)phenyl)amino)-1,3,5-triazine-2,4-diyl)bis(azanediyl))bis(octanoyl))bis(azanediyl))bis(1-carboxypentane-5,1-diyl))bis(azanediyl))bis(carbonyl))bis(azanediyl)) dipentanedioic Acid

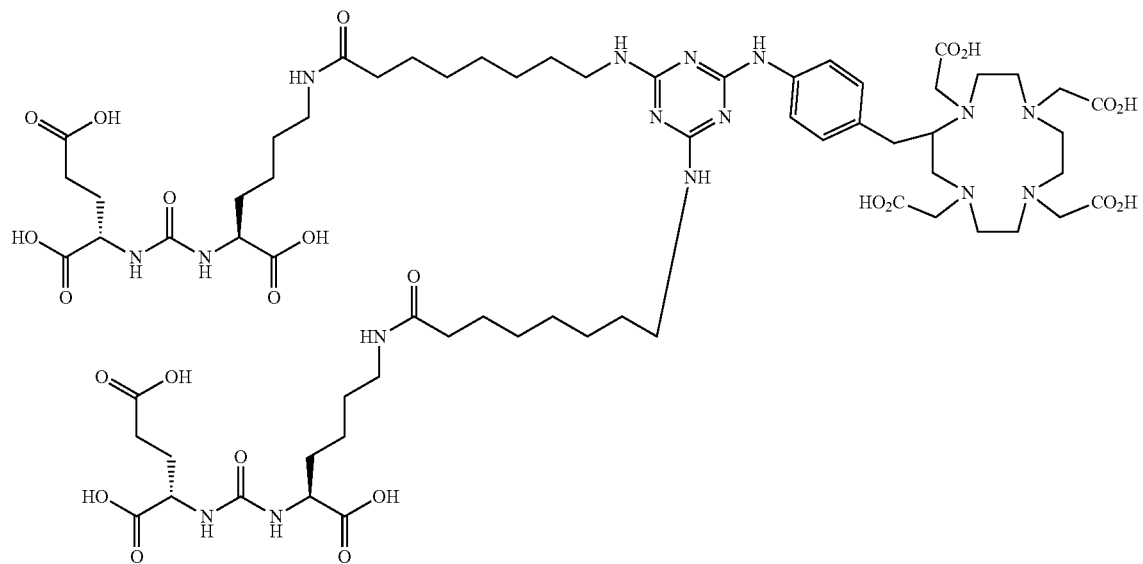 [SMILES: O=C(O)CC[C@H](NC(=O)N[C@@H](CCCCNC(=O)CCCCCCCNc1nc(NCCCCCCCC(=O)NCCCC[C@H](NC(=O)N[C@@H](CCC(=O)O)C(=O)O)C(=O)O)nc(Nc2ccc(CC3CN(CC(=O)O)CCN(CC(=O)O)CCN(CC(=O)O)CCN3CC(=O)O)cc2)n1)C(=O)O)C(=O)O]

To a solution of p-NH2-Bn-DOTA-tetra(t-Bu-ester) (Macrocyclics) (42.4 mg, 0.050 mmol) and cyanuric chloride (9.2 mg, 0.050 mmol) in DCM (2.0 mL) was added DIPEA (0.10 mL) and the mixture stirred at room temperature for 2 hours. Following stirring, the solvent was removed using a stream of nitrogen to give a residue. This residue was dissolved in DMSO (4.0 mL) and (S)-di-tert-butyl 2-(3-((S)-6-(8-aminooctanamido)-1-(tert-butoxy)-1-oxohexan-2-yl)ureido)pentanedioate (62.8 mg, 0.10 mmol) and $K_2CO_3$ (100 mg) were added to the resultant DMSO solution. The suspension thus obtained was stirred at room temperature for 72 hours and then lyophilized to afford a triazine intermediate which was deprotected using TFA (4.0 mL) and DCM (1.0 mL). The TFA/DCM mixture was stirred at room temperature overnight following which the solvent was removed using a stream of nitrogen to afford the titled crude as a solid. The crude was purified by Biotage SP4 using C18 cartridge to give pure ((2S,2'S)-2,2'-((((((1S,1'S)-((8,8'-((6-((4-((1,4,7,10-tetrakis(carboxymethyl)-1,4,7,10-tetraazacyclododecan-2-yl)methyl)phenyl)amino)-1,3,5-triazine-2,4-diyl)bis(azanediyl))bis(octanoyl))bis(azanediyl))bis(1-carboxypentane-5,1-diyl))bis(azanediyl))bis(carbonyl))bis(azanediyl))dipentanedioic acid (10.0 mg) as a white solid. MS (ESI), 753.2 (M/2+H)$^+$.

Step 2. ((2S,2'S)-2,2'-((((((1S,1'S)-((8,8'-((6-((4-((1,4,7,10-tetrakis(carboxymethyl)-1,4,7,10-tetraazacyclododecan-2-yl)methyl)phenyl)amino)-1,3,5-triazine-2,4-diyl)bis(azanediyl))bis(octanoyl))bis(azanediyl))bis(1-carboxypentane-5,1-diyl))bis(azanediyl))bis(carbonyl))bis(azanediyl)) dipentanedioic Acid Lutetium Complex To solid (((2S,2'S)-2,2'-((((((1S,1'S)-((8,8'-((6-((4-((1,4,7,10-tetrakis(carboxymethyl)-1,4,7,10-tetraazacyclododecan-2-yl)methyl)phenyl)amino)-1,3,5-triazine-2,4-diyl)bis(azanediyl))bis(octanoyl))bis(azanediyl))bis(1-carboxypentane-5,1-diyl))bis(azanediyl))bis(carbonyl))bis(azanediyl))dipentanedioic acid (8.5 mg, 0.005646 mmol) was added $LuCl_3$ (1.47 mL of a 0.00385 mmol/mL, 0.005646 mmol). The reaction mixture was heated at 70° C. for 1 hour and then lyophilized to to give (2S,2'S)-2,2'-((((((1S,1'S)-((8,8'-((6-((4-((1,4,7,10-tetrakis(carboxymethyl)-1,4,7,10-tetraazacyclododecan-2-yl)methyl)phenyl)amino)-1,3,5-triazine-2,4-diyl)bis(azanediyl))bis(octanoyl))bis(azanediyl))bis(1-carboxypentane-5,1-diyl))bis(azanediyl))bis(carbonyl))bis(azanediyl)) dipentanedioic acid lutetium complex (8.6 mg) as a white solid. MS (ESI), 1678.0 (M+H)$^+$.

Example 7. (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex

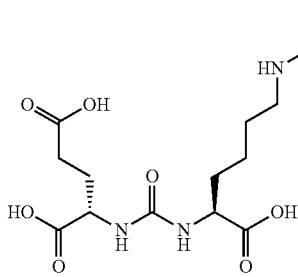
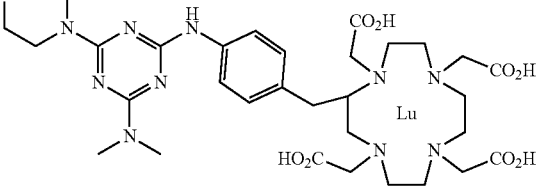

Step 1. (S)-di-tert-butyl 2-(3-((S)-6-(11-(4-((benzyloxy)carbonyl)piperazin-1-yl)undecanamido)-1-(tert-butoxy)-1-oxohexan-2-yl)ureido)pentanedioate

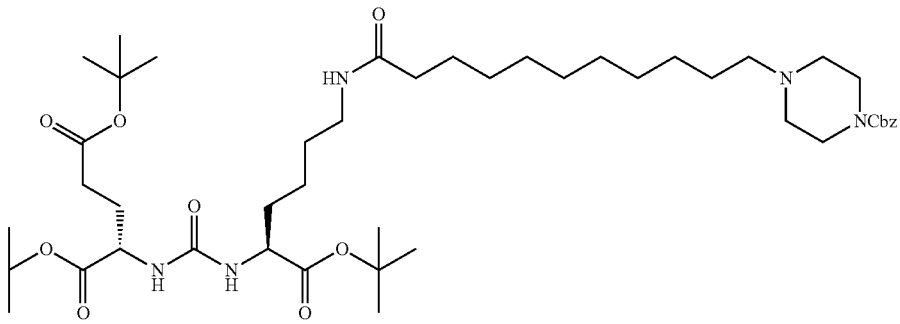 [SMILES: CC(C)OC(=O)[C@H](CCC(=O)OC(C)(C)C)NC(=O)N[C@@H](CCCCNC(=O)CCCCCCCCCCN1CCN(C(=O)OCc2ccccc2)CC1)C(=O)OC(C)(C)C]

A solution of (S)-di-tert-butyl 2-(3-((S)-6-amino-1-(tert-butoxy)-1-oxohexan-2-yl)ureido)pentanedioate (1.023 g, 2.097 mmol), 11-(4-((benzyloxy)carbonyl)piperazin-1-yl) undecanoic acid (0.77 g, 1.9059 mmol), EDCI (0.40 g, 2.097 mmol), HOBt (0.27 g, 2.097 mmol) and DIPEA (1.0 mL) in dichloroethane (DCE; 25 mL) was stirred at room temperature overnight. The following day, the solvent was evaporated to give a residue, which was purified using Biotage column chromatography and a mixture of DCM/MeOH as the eluant to give (S)-di-tert-butyl 2-(3-((S)-6-(11-(4-((benzyloxy)carbonyl)piperazin-1-yl)undecanamido)-1-(tert-butoxy)-1-oxohexan-2-yl)ureido)pentanedioate (1.52 g, 91%) as a yellowish solid. MS (ESI), 874.3 (M+H)$^+$.

Step 2. (S)-di-tert-butyl 2-(3-((S)-1-(tert-butoxy)-1-oxo-6-(11-(piperazin-1-yl)undecanamido)hexan-2-yl)ureido)pentanedioate

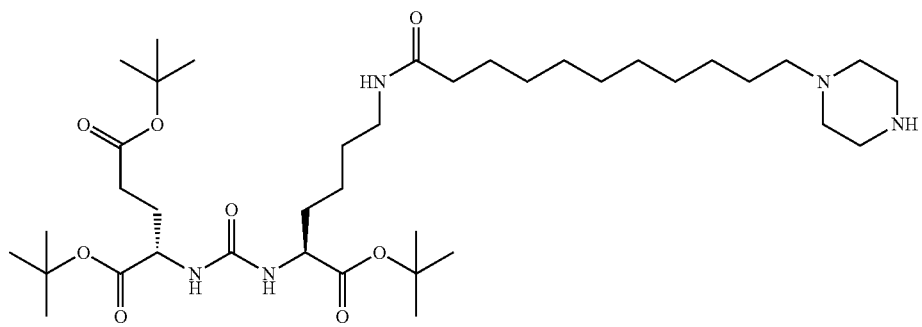 [SMILES: CC(C)(C)OC(=O)CC[C@H](NC(=O)N[C@@H](CCCCNC(=O)CCCCCCCCCCN1CCNCC1)C(=O)OC(C)(C)C)C(=O)OC(C)(C)C]

To a solution of (S)-di-tert-butyl 2-(3-((S)-6-(11-(4-((benzyloxy)carbonyl)piperazin-1-yl)undecanamido)-1-(tert-butoxy)-1-oxohexan-2-yl)ureido)pentanedioate (1.50 g, 1.72 mmol) and ammonium formate (1.0 g) in ethanol (60 mL) was added palladium on carbon (300 mg). The reaction mixture was stirred at room temperature for overnight and filtered through a pad of celite followed by washing of the celite pad using ethyl acetate (EtOAc). The solvent was removed under reduced pressure and the residue dissolved in dichloromethane (DCM). The DCM solution was was washed using saturated sodium bicarbonate and then partitioned to separate the organic layer from the aqueous layer. Concentration pf the organic layer under reduced pressure afforded the titled product as a yellowish solid (1.2345 g, 97% yield). MS (ESI), 740.4 (M+H)$^+$.

Step 3. (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl) phenyl)amino)-1,3,5-triazin-2-yl)piperazin-1-yl) undecanamido)pentyl) ureido)pentanedioic Acid

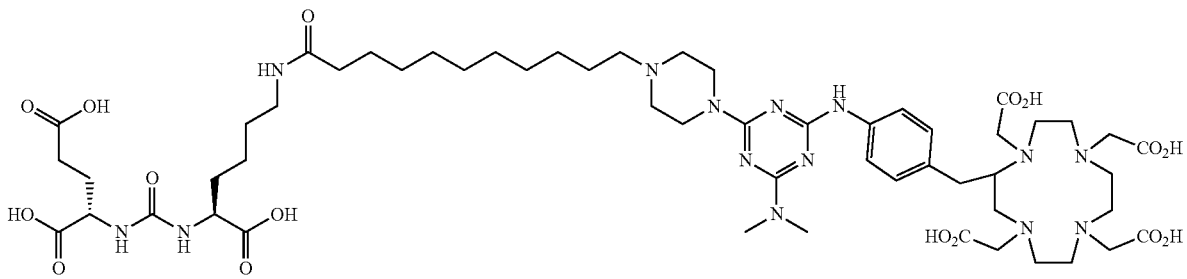 [SMILES: CN(C)c1nc(Nc2ccc(CC3CN(CC(=O)O)CCN(CC(=O)O)CCN(CC(=O)O)CCN3CC(=O)O)cc2)nc(N2CCN(CCCCCCCCCCC(=O)NCCCC[C@H](NC(=O)N[C@@H](CCC(=O)O)C(=O)O)C(=O)O)CC2)n1]

To a solution of p-NH2-Bn-DOTA-tetra(t-Bu-ester) (Macrocyclics) (42.4 mg, 0.050 mmol) and cyanuric chloride (9.2 mg, 0.050 mmol) in DCM (2.0 mL) was added DIPEA (0.10 mL) and resultant mixture was stirred at room temperature for 2 hrs. Following stirring, the solvent was removed under a stream of nitrogen to give a residue, which was dissolved in DMSO (1.0 mL) prior to the addition of (S)-di-tert-butyl 2-(3-((S)-1-(tert-butoxy)-1-oxo-6-(11-(piperazin-1-yl)undecanamido)hexan-2-yl)ureido)pentanedioate (34 mg, 0.05 mmol) and $K_2CO_3$ (50 mg). The resultant suspension was stirred at room temperature for 2 hrs, following which a tetrahydrofuran solution of dimethylamine (0.2 mL, 2.0 M in THF) was added. After additional stirring of the reaction mixture at room temperature for 16 hours, the reaction was lyophilized to afford the crude triazine intermediate. Deprotection of the crude using TFA (2.0 mL) and DCM (1.0 mL) was carried out at room temperature overnight. The following day, the solvent was removed under a stream of nitrogen to give a residue, which was purified by Biotage SP4 using C18 cartridge to give (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (24 mg) as a white solid. MS (ESI), 601.2 (M/2+H)+.

Step 4. (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex To solid (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (9.4 mg, 0.00783 mmol) was added $LuCl_3$ (1.02 mL of a 0.00770 mmol/mL, 0.00783 mmol). The reaction mixture was heated at 90° C. for 1 hour and then lyophilized to to give (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid lutetium complex (11.1 mg) as a white solid. MS (ESI), 1373.7 (M+H)+.

Example 8. (2S)-2-(3-((1S)-1-carboxy-5-(11-(4-(4-(piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex

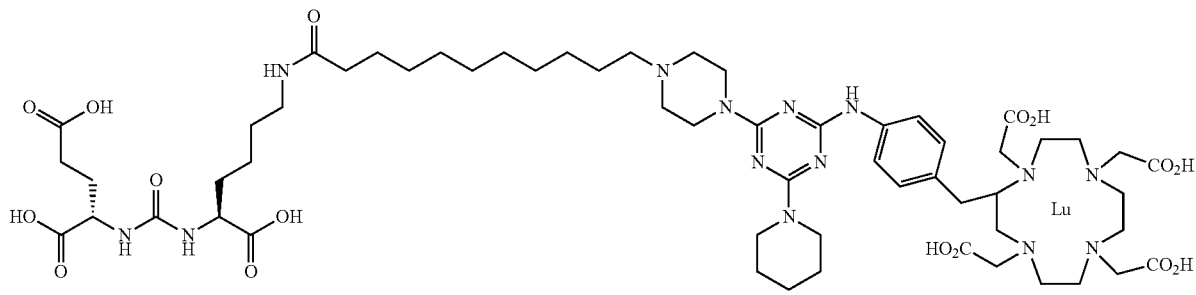

Step 1. ((2S)-2-(3-((1S)-1-carboxy-5-(11-(4-(4-(piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid

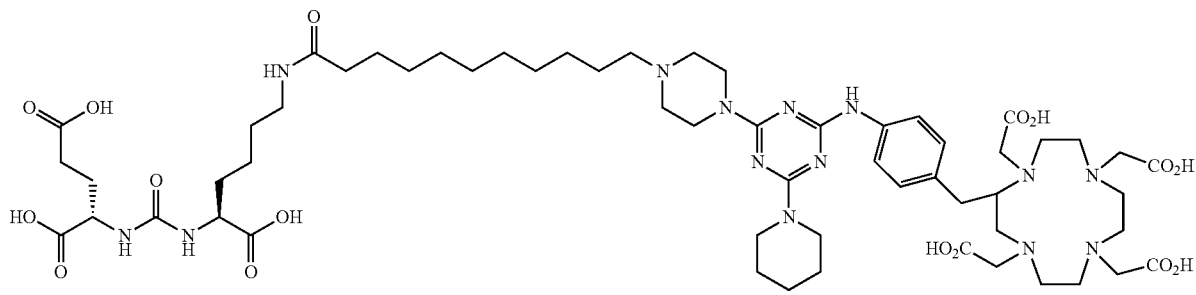 [SMILES: O=C(O)CC[C@H](NC(=O)N[C@@H](CCCCNC(=O)CCCCCCCCCCN1CCN(c2nc(Nc3ccc(CC4CN(CC(=O)O)CCN(CC(=O)O)CCN(CC(=O)O)CCN4CC(=O)O)cc3)nc(N3CCCCC3)n2)CC1)C(=O)O)C(=O)O]

To a solution of p-NH2-Bn-DOTA-tetra(t-Bu-ester) (Macrocyclics) (42.4 mg, 0.050 mmol) and cyanuric chloride (9.2 mg, 0.050 mmol) in DCM (2.0 mL) was added DIPEA (0.10 mL) and the solution was stirred at room temperature for 2 hrs. The solvent was then removed using a stream of nitrogen to give a residue, which was dissolved in DMSO (1.0 mL) prior to the addition of piperidine (4.25 mg, 0.05 mmol). The resultant suspension was stirred at room temperature for 2 hours following which (S)-di-tert-butyl 2-(3-((S)-1-(tert-butoxy)-1-oxo-6-(11-(piperazin-1-yl)undecanamido)hexan-2-yl)ureido)pentanedioate (37 mg, 0.05 mmol) and K$_2$CO$_3$ (50 mg) were added to the DMSO solution. After additional stirring at room temperature for 16 hours and the mixture was lyophilized to afford the crude triazine intermediate, which was deprotected using TFA (2.0 mL) and DCM (1.0 mL). Deprotection was carried out by stirring the crude at room temperature overnight and the following day the solvent was removed using a stream of nitrogen to give a residue which was purified by Biotage SP4 using a C18 cartridge to give ((2S)-2-(3-((1S)-1-carboxy-5-(11-(4-(4-(piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (22 mg) as a white solid. MS (ESI), 621.2 (M/2+H)$^+$.

Step 2. (2S)-2-(3-((1S)-1-carboxy-5-(11-(4-(4-(piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex To solid (2S)-2-(3-((1S)-1-carboxy-5-(11-(4-(4-(piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (12.4 mg, 0.01 mmol) was added LuCl$_3$ (1.30 mL of a 0.00770 mmol/mL, 0.01 mmol). The reaction mixture was heated at 90° C. for 1 hour and then lyophilized to to give (2S)-2-(3-((1S)-1-carboxy-5-(11-(4-(4-(piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid lutetium complex (14.0 mg) as a white solid. MS (ESI), 1413.7 (M+H)$^+$.

Example 9. (2S)-2-(3-((1S)-1-carboxy-5-(11-(4-(4-((2-(2-(2-carboxyethoxy)ethoxy)ethyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex

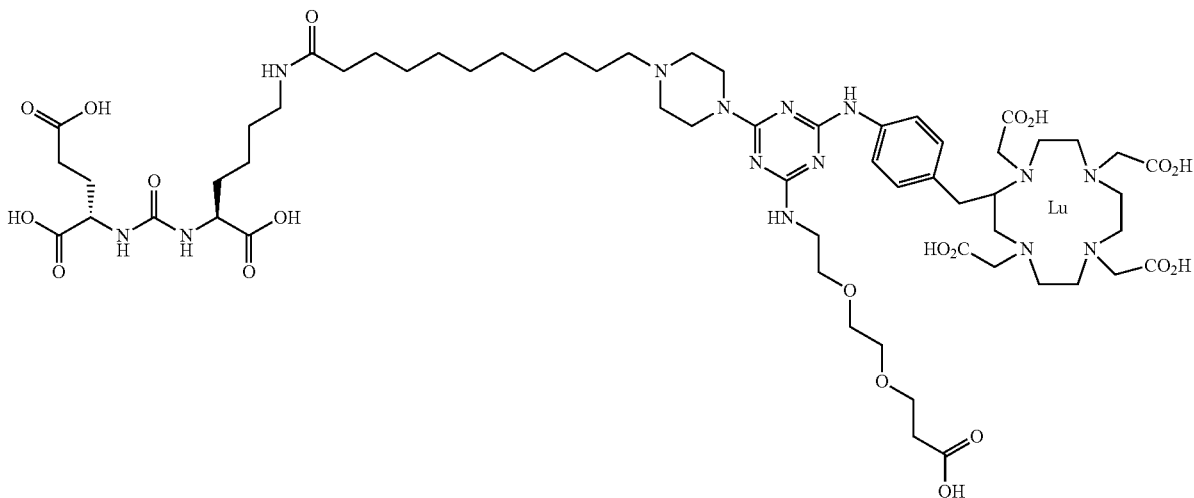

Step 1. (2S)-2-(3-((1S)-1-carboxy-5-(11-(4-(4-((2-(2-(2-carboxyethoxy)ethoxy)ethyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid

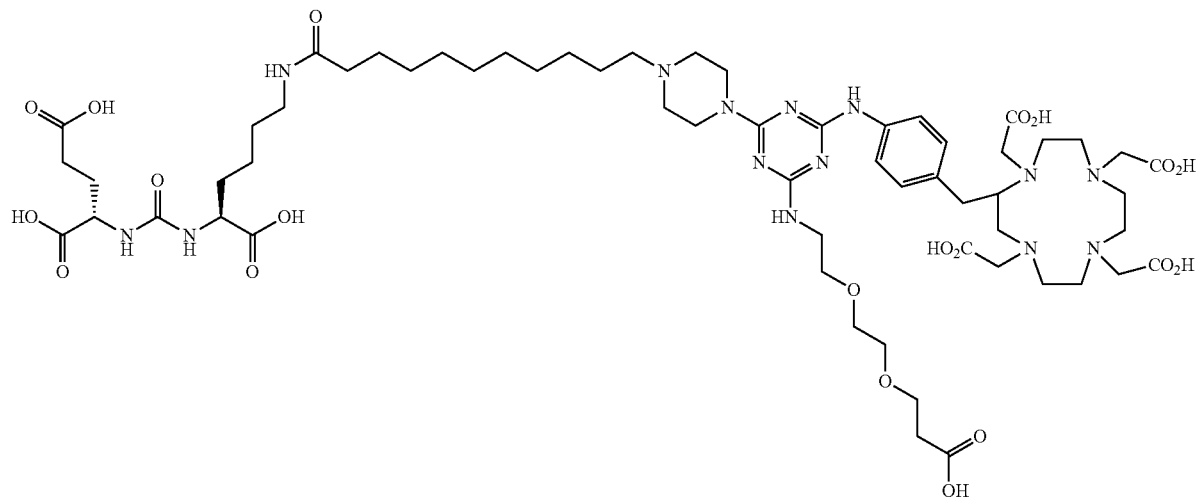 [SMILES: O=C(O)CCOCCOCCNc1nc(Nc2ccc(CC3CN(CC(=O)O)CCN(CC(=O)O)CCN(CC(=O)O)CCN3CC(=O)O)cc2)nc(N2CCN(CCCCCCCCCCC(=O)NCCCC[C@H](NC(=O)N[C@@H](CCC(=O)O)C(=O)O)C(=O)O)CC2)n1]

To a DCM solution (2.0 mL) of p-NH2-Bn-DOTA-tetra (t-Bu-ester) (Macrocyclics) (42.4 mg, 0.050 mmol) and cyanuric chloride (9.2 mg, 0.050 mmol) was added DIPEA (0.10 mL). After stirring at room temperature for 2 hours the solvent was removed under a stream of nitrogen to give a residue, which was dissolved in DMSO (1.0 mL). Tert-butyl 3-(2-(2-aminoethoxy)ethoxy)propanoate (11.67 mg, 0.05 mmol) and $K_2CO_3$ (50 mg) were then added to the DMSO solution and the resultant suspension was stirred at room temperature for 2 hours. (S)-di-tert-butyl 2-(3-((S)-1-(tert-butoxy)-1-oxo-6-(11-(piperazin-1-yl)undecanamido)hexan-2-yl)ureido)pentanedioate (37 mg, 0.05 mmol) was then added. After stirring for 16 hours the reaction mixture was lyophilized to afford the crude triazine intermediate which was deprotected using TFA (2.0 mL) and DCM (1.0 mL). Deprotection was carried out by stirring the crude at room temperature overnight and the following day the solvent was removed using a stream of nitrogen to give a residue which was purified by Biotage SP4 using C18 cartridge to give (2S)-2-(3-((1S)-1-carboxy-5-(11-(4-(4-((2-(2-(2-carboxyethoxy)ethoxy)ethyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (29.4 mg) as a white solid. MS (ESI), 667.2 (M/2+H)$^+$.

Step 2. (2S)-2-(3-((1S)-1-carboxy-5-(11-(4-(4-((2-(2-(2-carboxyethoxy)ethoxy)ethyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex To solid (2S)-2-(3-((1S)-1-carboxy-5-(11-(4-(4-((2-(2-(2-carboxyethoxy)ethoxy)ethyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (13.1 mg, 0.01 mmol) was added $LuCl_3$ (1.30 mL of a 0.00770 mmol/mL, 0.01 mmol). The reaction mixture was heated at 90° C. for 1 hour and lyophilized to to give (2S)-2-(3-((1S)-1-carboxy-5-(11-(4-(4-((2-(2-(2-carboxyethoxy)ethoxy)ethyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid lutetium complex (14.5 mg) as a white solid. MS (ESI), 1505.7 (M+H)$^+$.

Example 10. (2S)-2-(3-((1S)-1-carboxy-5-(11-(4-(4-((26-carboxy-3,6,9,12,15,18,21,24-octaoxahexacosyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex

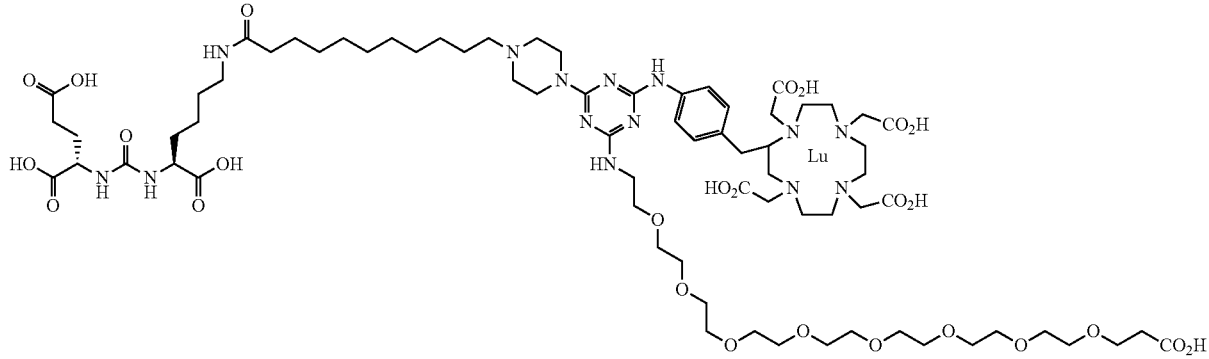

Step 1. (2S)-2-(3-((1S)-1-carboxy-5-(11-(4-(4-((26-carboxy-3,6,9,12,15,18,21,24-octaoxahexacosyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid

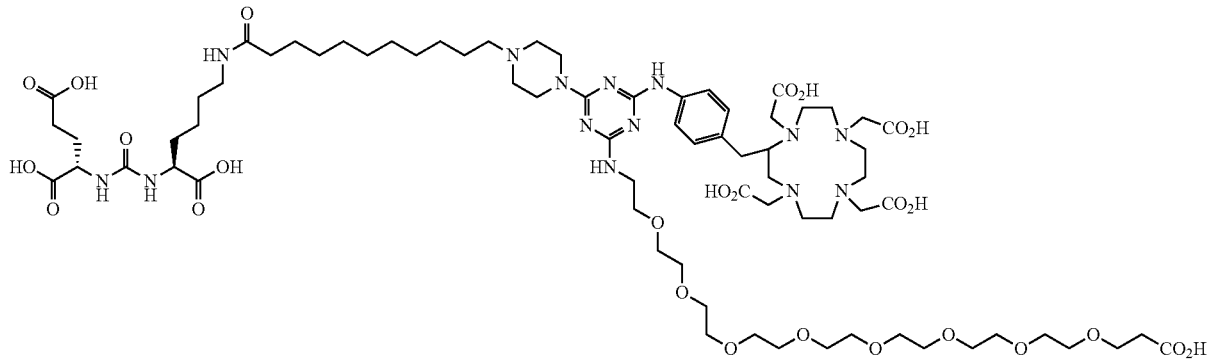 [SMILES: O=C(O)CCOCCOCCOCCOCCOCCOCCOCCOCCNc1nc(Nc2ccc(CC3CN(CC(=O)O)CCN(CC(=O)O)CCN(CC(=O)O)CCN3CC(=O)O)cc2)nc(N2CCN(CCCCCCCCCCC(=O)NCCCC[C@H](NC(=O)N[C@@H](CCC(=O)O)C(=O)O)C(=O)O)CC2)n1]

To a solution of p-NH2-Bn-DOTA-tetra(t-Bu-ester) (Macrocyclics) (42.4 mg, 0.050 mmol) and cyanuric chloride (9.2 mg, 0.050 mmol) in DCM (2.0 mL) was added DIPEA (0.10 mL). The reaction was stirred at room temperature for 2 hrs and the solvent removed following stirring using a stream of nitrogen. The residue thus obtained was dissolved in DMSO (1.0 mL) and 1-amino-3,6,9,12,15,18,21,24-octaoxaheptacosan-27-oic acid (22.1 mg, 0.05 mmol) and $K_2CO_3$ (50 mg) were added to the DMSO solution. The resultant suspension was stirred at room temperature for 2 hrs following which (S)-di-tert-butyl 2-(3-((S)-1-(tert-butoxy)-1-oxo-6-(11-(piperazin-1-yl)undecanamido)hexan-2-yl)ureido)pentanedioate (37 mg, 0.05 mmol) was then added. After stirring for an additional 16 hours at room temperature the crude reaction was lyophilized to afford the triazine intermediate, which was deprotected overnight at room temperature using TFA (2.0 mL) and DCM (1.0 mL). The crude product was purified by Biotage SP4 using a C18 cartridge to give (2S)-2-(3-((1S)-1-carboxy-5-(11-(4-(4-((26-carboxy-3,6,9,12,15,18,21,24-octaoxahexacosyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (31.4 mg) as a white solid. MS (ESI), 799.3 $(M/2+H)^+$.

Step 2. (2S)-2-(3-((1S)-1-carboxy-5-(11-(4-(4-((26-carboxy-3,6,9,12,15,18,21,24-octaoxahexacosyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex $LuCl_3$ (0.69 mL of a 0.00770 mmol/mL, 0.00532 mmol) was added to solid (2S)-2-(3-((1S)-1-carboxy-5-(11-(4-(4-((26-carboxy-3,6,9,12,15,18,21,24-octaoxahexacosyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)

pentanedioic acid (8.5 mg, 0.00532 mmol). The reaction mixture was heated at 90° C. for 1 hour and then lyophilized to to give 2S)-2-(3-((1S)-1-carboxy-5-(11-(4-(4-((26-carboxy-3,6,9,12,15,18,21,24-octaoxahexacosyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid lutetium complex (8.2 mg) as a white solid. MS (ESI), 885.2 (M/2+H)$^+$.

Example 11. (2S)-2-(3-((1S)-5-(11-(4-(4-(((S)-5-(bis((1-(carboxymethyl)-1H-imidazol-2-yl)methyl)amino)-1-carboxypentyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic Acid Lutetium Complex

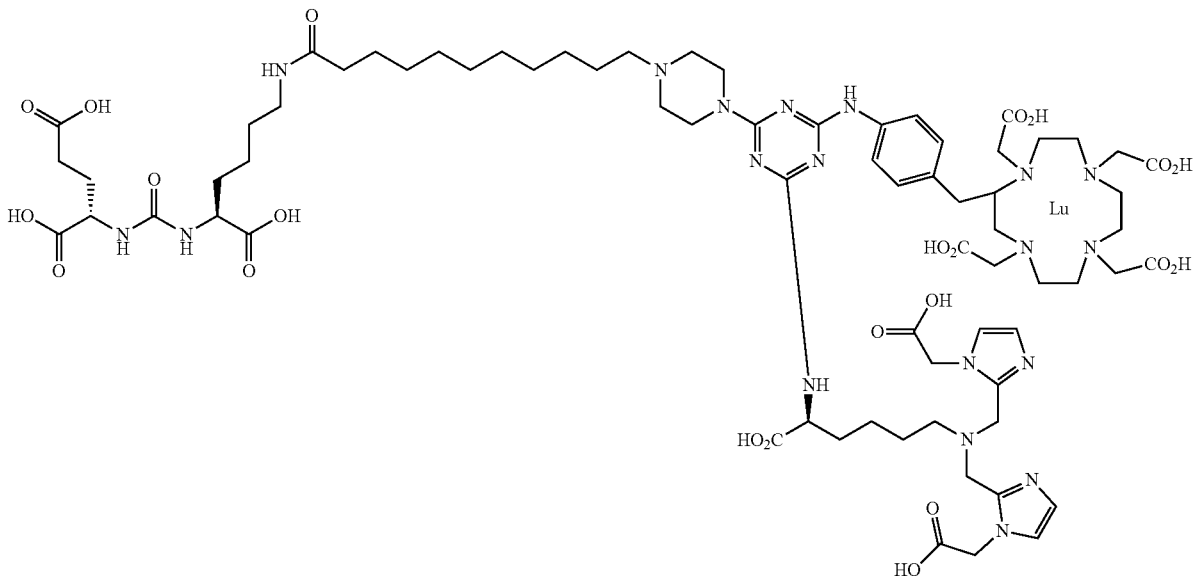

Step 1. (2S)-2-(3-((1S)-5-(11-(4-(4-(((S)-5-(bis((1-(carboxymethyl)-1H-imidazol-2-yl)methyl)amino)-1-carboxypentyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic Acid

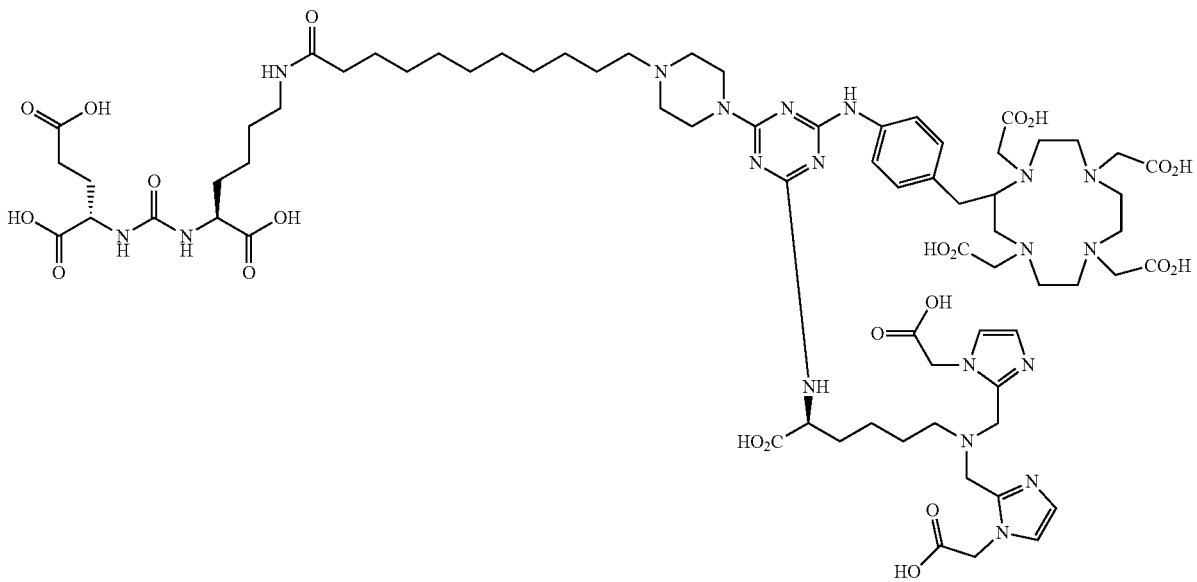 [SMILES: O=C(O)CC[C@H](NC(=O)N[C@@H](CCCCNC(=O)CCCCCCCCCCN1CCN(c2nc(Nc3ccc(CC4CN(CC(=O)O)CCN(CC(=O)O)CCN(CC(=O)O)CCN4CC(=O)O)cc3)nc(N[C@@H](CCCCN(Cc3nccn3CC(=O)O)Cc3nccn3CC(=O)O)C(=O)O)n2)CC1)C(=O)O)C(=O)O]

To a solution of p-NH2-Bn-DOTA-tetra(t-Bu-ester) (Macrocyclics) (42.4 mg, 0.050 mmol) and cyanuric chloride (9.2 mg, 0.050 mmol) in DCM (2.0 mL) was added DIPEA (0.10 mL). After stirring at room temperature for 2 hours the solvent was removed using a stream of nitrogen gas to give a residue. This residue was dissolved in DMSO (1.0 mL) and (S)-2-amino-6-(bis((1-(2-(tert-butoxy)-2-oxoethyl)-1H-imidazol-2-yl)methyl)amino)hexanoic acid (26.7 mg, 0.05 mmol) and K$_2$CO$_3$ (50 mg) were then added. The resultant suspension was stirred at room temperature overnight. The following day (S)-di-tert-butyl 2-(3-((S)-1-(tert-butoxy)-1-oxo-6-(11-(piperazin-1-yl)undecanamido)hexan-2-yl)ureido)pentanedioate (37 mg, 0.05 mmol) was added and the reaction mixture was stirred at room temperature for an additional 24 hours. Lyophilization afforded the crude triazine intermediate which was deprotected overnight at room temperature using TFA (3.0 mL) and DCM (1.0 mL). The deprotected crude final product was purified by Biotage SP4 using a C18 cartridge to give (2S)-2-(3-((1S)-5-(11-(4-(4-(((S)-5-(bis((1-(carboxymethyl)-1H-imidazol-2-yl)methyl)amino)-1-carboxypentyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic acid (41.5 mg) as a white solid. MS (ESI), 789.6 (M/2+H)$^+$.

Step 2. (2S)-2-(3-((1S)-5-(11-(4-(4-(((S)-5-(bis((1-(carboxymethyl)-1H-imidazol-2-yl)methyl)amino)-1-carboxypentyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic Acid Lutetium Complex To solid (2S)-2-(3-((1S)-5-(11-(4-(4-(((S)-5-(bis((1-(carboxymethyl)-1H-imidazol-2-yl)methyl)amino)-1-carboxypentyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic acid (16.3 mg, 0.0103 mmol) was added LuCl$_3$ (1.0 mL, 0.0103 mmol/mL, 0.0103 mmol. The reaction mixture was heated at 90° C. for 1 hour and then lyophilized to to give (2S)-2-(3-((1S)-5-(11-(4-(4-(((S)-5-(bis((1-(carboxymethyl)-1H-imidazol-2-yl)methyl)amino)-1-carboxypentyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic acid lutetium complex (15.7 mg) as a white solid. MS (ESI), 875.6 (M/2+H)$^+$.

Example 12. (2S)-2-(3-((1S)-5-(11-(4-(4-(bis(carboxymethyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic Acid Lutetium Complex

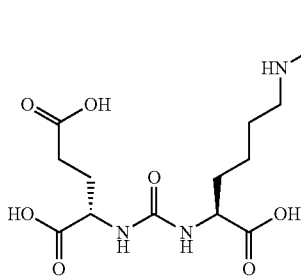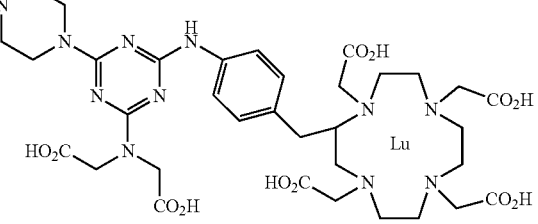

Step 1. (2S)-2-(3-((1S)-5-(11-(4-(4-(bis(carboxymethyl)amino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic Acid

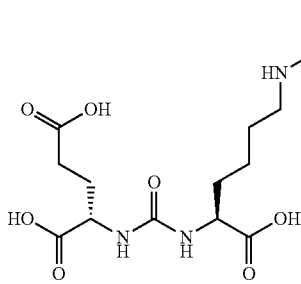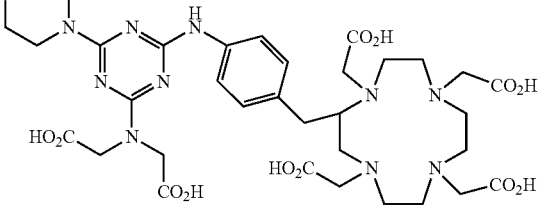

To a DCM (2.0 mL) solution of p-NH2-Bn-DOTA-tetra (t-Bu-ester) (Macrocyclics) (42.4 mg, 0.050 mmol) and cyanuric chloride (9.2 mg, 0.050 mmol) was added DIPEA (0.10 mL) and resultant mixture was stirred at room temperature for 2 hrs. Removal of the solvent using a stream of nitrogen gave a residue which was dissolved in DMSO (1.0 mL) prior to the addition of di-tert-butyl 2,2'-azanediyldiacetate (24.5 mg, 0.10 mmol) and $K_2CO_3$ (50 mg) were added. The resultant suspension was stirred at room temperature for overnight and the following day (S)-di-tert-butyl 2-(3-((S)-1-(tert-butoxy)-1-oxo-6-(11-(piperazin-1-yl)undecanamido) hexan-2-yl)ureido)pentanedioate (37 mg, 0.05 mmol) was added and the stirring continued at room temperature for 24 hours. Lyophilization of this suspension afforded the triazine intermediate, which was deprotected at room temperature overnight using TFA (3.0 mL) and DCM (1.0 mL). The deprotected crude product was purified by Biotage SP4 using a C18 cartridge to give (2S)-2-(3-((1S)-5-(11-(4-(4-(bis(carboxymethyl)amino)-6-((4-((1,4,7,10-tetrakis(carboxymethyl)-1,4,7,10-tetraazacyclododecan-2-yl)methyl) phenyl)amino)-1,3,5-triazin-2-yl)piperazin-1-yl) undecanamido)-1-carboxypentyl)ureido)pentanedioic acid (27.0 mg) as a white solid. MS (ESI), 645.2 $(M/2+H)^+$.

Step 2. (2S)-2-(3-((1S)-5-(11-(4-(4-(bis(carboxymethyl)amino)-6-((4-((1,4,7,10-tetrakis(carboxymethyl)-1,4,7,10-tetraazacyclododecan-2-yl)methyl) phenyl)amino)-1,3,5-triazin-2-yl)piperazin-1-yl) undecanamido)-1-carboxypentyl)ureido) pentanedioic Acid Lutetium Complex $LuCl_3$ (0.89 mL of a 0.0103 mmol/mL, 0.00915 mmol) was added to solid reagent of (2S)-2-(3-((1S)-5-(11-(4-(4-(bis(carboxymethyl)amino)-6-((4-((1,4,7,10-tetrakis(carboxymethyl)-1,4,7,10-tetraazacyclododecan-2-yl)methyl) phenyl)amino)-1,3,5-triazin-2-yl)piperazin-1-yl) undecanamido)-1-carboxypentyl)ureido)pentanedioic acid (11.8 mg, 0.00915 mmol). The reaction mixture was heated at 90° C. for 1 hour and then lyophilized to to give (2S)-2-(3-((1S)-5-(11-(4-(4-(bis(carboxymethyl)amino)-6-((4-((1,4,7,10-tetrakis(carboxymethyl)-1,4,7,10-tetraazacyclododecan-2-yl)methyl)phenyl)amino)-1,3,5-triazin-2-yl) piperazin-1-yl)undecanamido)-1-carboxypentyl)ureido) pentanedioic acid lutetium complex (12.0 mg) as a white solid. MS (ESI), 731.2 $(M/2+H)^+$.

Example 13. (2S)-2-(3-((1S)-1-carboxy-5-(11-(4-(4-(methylamino)-6-((4-((1,4,7,10-tetrakis(carboxymethyl)-1,4,7,10-tetraazacyclododecan-2-yl)methyl) phenyl)amino)-1,3,5-triazin-2-yl)piperazin-1-yl) undecanamido)pentyl)ureido)pentanedioic Acid Lutetium Complex

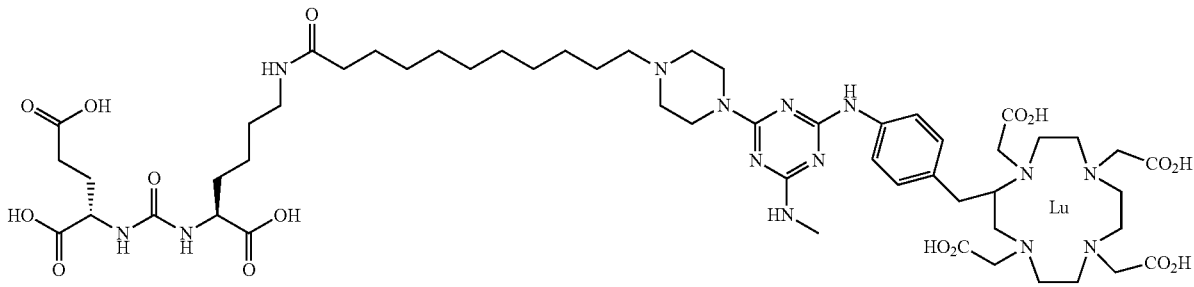

Step 1. (2S)-2-(3-((1S)-1-carboxy-5-(11-(4-(4-(methylamino)-6-((4-((1,4,7,10-tetrakis(carboxymethyl)-1,4,7,10-tetraazacyclododecan-2-yl)methyl) phenyl)amino)-1,3,5-triazin-2-yl)piperazin-1-yl) undecanamido)pentyl)ureido)pentanedioic Acid

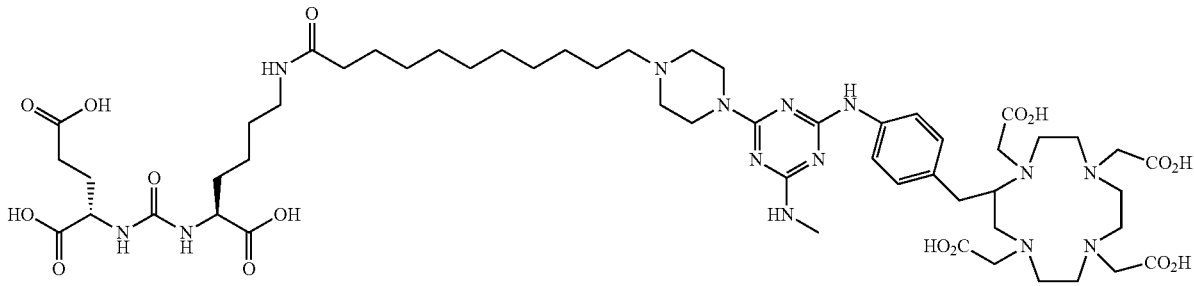 [SMILES: CNc1nc(Nc2ccc(CC3CN(CC(=O)O)CCN(CC(=O)O)CCN(CC(=O)O)CCN3CC(=O)O)cc2)nc(N2CCN(CCCCCCCCCCC(=O)NCCCC[C@H](NC(=O)N[C@@H](CCC(=O)O)C(=O)O)C(=O)O)CC2)n1]

To a DCM (2.0 mL) solution of p-NH2-Bn-DOTA-tetra (t-Bu-ester) (Macrocyclics) (42.4 mg, 0.050 mmol) and cyanuric chloride (9.2 mg, 0.050 mmol) was added DIPEA (0.10 mL) and the solution stirred at room temperature for 2 hours. After stirring the solvent was removed using a stream of nitrogen gas to give a residue. This residue was dissolved in DMSO (1.0 mL) and the solution was contacted with methanamine (0.10 mL, 2.0 M in THF) and $K_2CO_3$ (50 mg). The resultant suspension was stirred at room temperature for 4 hours. (S)-di-tert-butyl 2-(3-((S)-1-(tert-butoxy)-1-oxo-6-(11-(piperazin-1-yl)undecanamido)hexan-2-yl)ureido)pentanedioate (37 mg, 0.05 mmol) was added then added to the DMSO solution and the reaction mixture was stirred at room temperature for an additional 24 hrs prior to lyophilization to afford the crude triazine intermediate. Deprotection using TFA (3.0 mL) and DCM (1.0 mL) at room temperature, overnight followed by removal of the solvent using a stream of nitrogen gave crude product which was purified by Biotage SP4 using a C18 cartridge to give (2S)-2-(3-((1S)-1-carboxy-5-(11-(4-(4-(methylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (10.8 mg) as a white solid. MS (ESI), 594.2 $(M/2+H)^+$.

Step 2. (2S)-2-(3-((1S)-1-carboxy-5-(11-(4-(4-(methylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex To solid (2S)-2-(3-((1S)-1-carboxy-5-(11-(4-(4-(methylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid, (7.7 mg, 0.00649 mmol) was added $LuCl_3$ (0.63 mL of a 0.0103 mmol/mL, 0.00649 mmol). The reaction mixture was heated at 90° C. for 1 hour and then lyophilized to to give (2S)-2-(3-((1S)-1-carboxy-5-(11-(4-(4-(methylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid lutetium complex (7.9 mg) as a white solid. MS (ESI), 680.2 $(M/2+H)^+$.

Example 14. (2S)-2-(3-((1S)-5-(11-(4-(4-(4-(3-aminopropyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic Acid Lutetium Complex

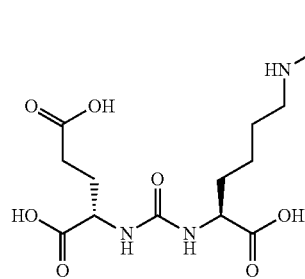

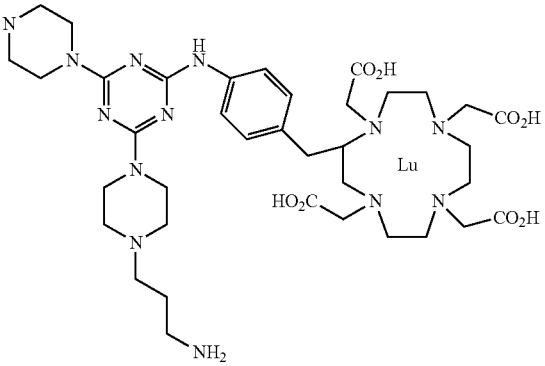

Step 1. (2S)-2-(3-((1S)-5-(11-(4-(4-(4-(3-aminopropyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic Acid

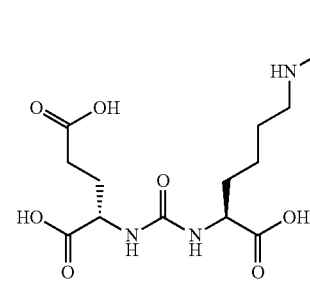

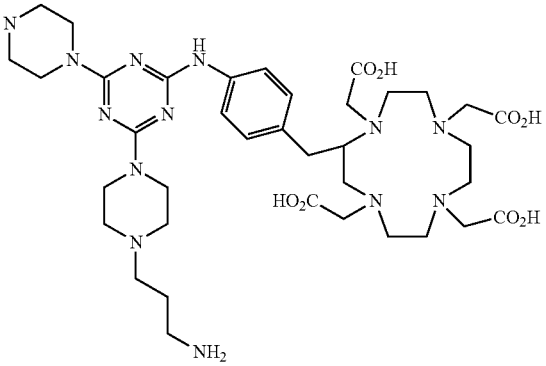

To a solution of p-NH2-Bn-DOTA-tetra(t-Bu-ester) (Macrocyclics) (42.4 mg, 0.050 mmol) and cyanuric chloride (9.2 mg, 0.050 mmol) in DCM (2.0 mL) was added DIPEA (0.10 mL) and the solution was stirred at room temperature for 2 hours. After stirring the solvent was removed under a stream of nitrogen to give a residue which was dissolved in DMSO (1.0 mL) prior to the addition of (S)-di-tert-butyl 2-(3-((S)-1-(tert-butoxy)-1-oxo-6-(11-(piperazin-1-yl)undecanamido)hexan-2-yl)ureido)pentanedioate (37 mg, 0.05 mmol) and K₂CO₃ (50 mg). The resultant suspension was stirred at room temperature for 2 hours and 3-(piperazin-1-yl)propan-1-amine (47 mg) was then added following which the reaction mixture was stirred for an additional 16 hours at room temperature. Lyophilization after 16 hours afforded the crude triazine intermediate which was deprotected at room temperature, overnight using TFA (2.0 mL) and DCM (1.0 mL). The deprotected product was purified by Biotage SP4 using a C18 cartridge to give (2S)-2-(3-((1S)-5-(11-(4-(4-(4-(3-aminopropyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic acid (25 mg) as a white solid. MS (ESI), 650.3 (M/2+H)⁺.

Step 2. (2S)-2-(3-((1S)-5-(11-(4-(4-(4-(3-aminopropyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido) pentanedioic Acid Lutetium Complex To solid (2S)-2-(3-((1S)-5-(11-(4-(4-(4-(3-aminopropyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic acid (10.7 mg, 0.00824 mmol) was added LuCl₃ (0.80 mL of a 0.0103 mmol/mL, 0.00824 mmol). The reaction mixture was heated at 90° C. for 1 hour and then lyophilized to give (2S)-2-(3-((1S)-5-(11-(4-(4-(4-(3-aminopropyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)-1-carboxypentyl)ureido)pentanedioic acid lutetium complex (10.2 mg) as a white solid. MS (ESI), 736.2 (M/2+H)⁺.

Example 15. (2S)-2-(3-((1S)-1-carboxy-5-(11-(4-(4-(4-(carboxymethyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl) piperazin-1-yl)undecanamido)pentyl)ureido) pentanedioic Acid Lutetium Complex

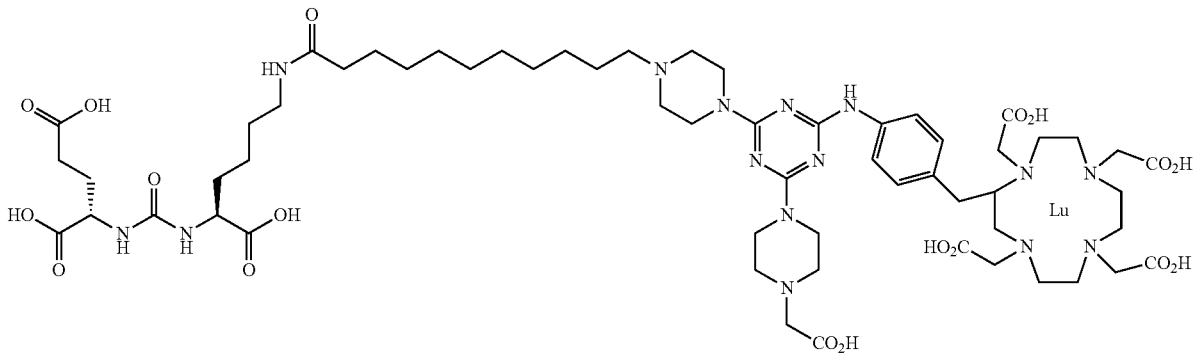

Step 1. (2S)-2-(3-((1S)-1-carboxy-5-(11-(4-(4-(4-(carboxymethyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl) piperazin-1-yl)undecanamido)pentyl)ureido) pentanedioic Acid

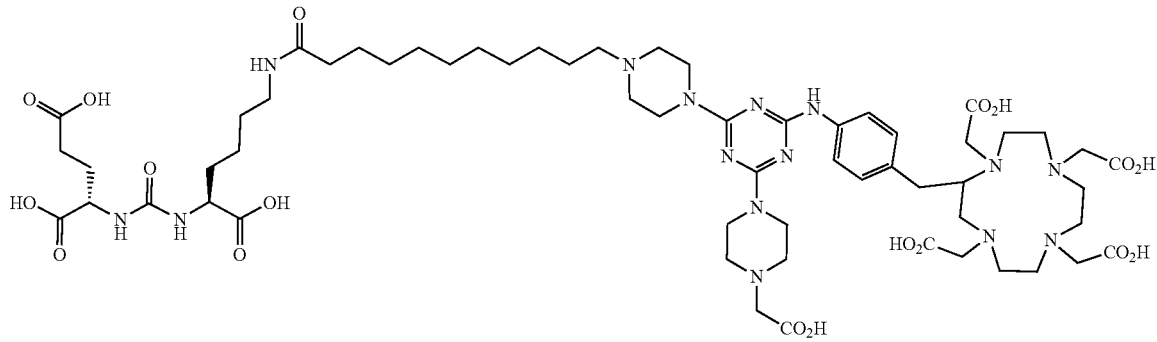 [SMILES: O=C(O)CC[C@H](NC(=O)N[C@@H](CCCCNC(=O)CCCCCCCCCCN1CCN(c2nc(Nc3ccc(CC4CN(CC(=O)O)CCN(CC(=O)O)CCN(CC(=O)O)CCN4CC(=O)O)cc3)nc(N3CCN(CC(=O)O)CC3)n2)CC1)C(=O)O)C(=O)O]

To a DCM solution (2.0 mL) of p-NH2-Bn-DOTA-tetra (t-Bu-ester) (Macrocyclics), (42.4 mg, 0.050 mmol) and cyanuric chloride (9.2 mg, 0.050 mmol) was added DIPEA (0.10 mL) the resultant solution was stirred at room temperature for 2 hours. After stirring, the solvent was removed using a stream of nitrogen to give a residue which was dissolved in DMSO (1.0 mL) prior to the addition of (S)-di-tert-butyl 2-(3-((S)-1-(tert-butoxy)-1-oxo-6-(11-(piperazin-1-yl)undecanamido)hexan-2-yl)ureido)pentanedioate (37 mg, 0.05 mmol) and $K_2CO_3$ (50 mg). The suspension thus obtained was stirred at room temperature for 2 hrs and tert-butyl 2-(piperazin-1-yl)acetate (50 mg) was then added to the reaction mixture and stirring was continued at room temperature for an additional 16 hours. Lyophilization of the reaction mixture at the end of 16 hours afforded a residue of the protected final product. This residue was contacted with TFA (2.0 mL) and DCM (1.0 mL) at room temperature overnight to cause removal of protecting groups, following which the solvent was removed under a stream of nitrogen to give crude deprotected product that was purified by Biotage SP4 using a C18 cartridge. The titled compound (2S)-2-(3-((1S)-1-carboxy-5-(11-(4-(4-(4-(carboxymethyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (14 mg) as obtained as a white solid. MS (ESI), 650.8 (M/2+H)+.

Step 2. (2S)-2-(3-((1S)-1-carboxy-5-(11-(4-(4-(4-(carboxymethyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex To solid (2S)-2-(3-((1S)-1-carboxy-5-(11-(4-(4-(4-(carboxymethyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (6.0 mg, 0.00426 mmol) was added $LuCl_3$ (0.45 mL of a 0.0103 mmol/mL, 0.00462 mmol). The reaction mixture was heated at 90° C. for 1 hour and lyophilized to to give (2S)-2-(3-((1S)-1-carboxy-5-(11-(4-(4-(4-(carboxymethyl)piperazin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid lutetium complex (5.6 mg) as a white solid. MS (ESI), 736.8 (M/2+H)+.

Example 16. (2S)-2-(3-((1S)-1-carboxy-5-(11-(4-(4-(4-(3-carboxypropyl)piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex

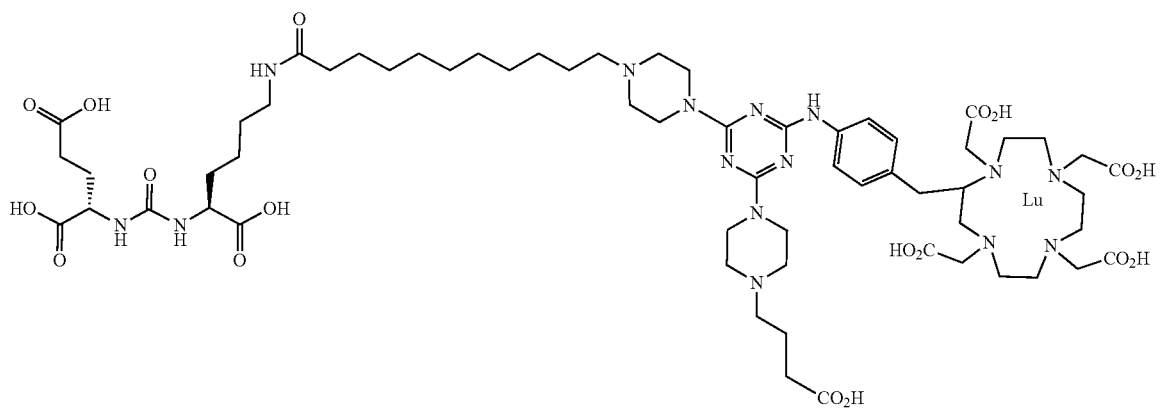

Step 1. (2S)-2-(3-((1S)-1-carboxy-5-(11-(4-(4-(4-(3-carboxypropyl)piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid

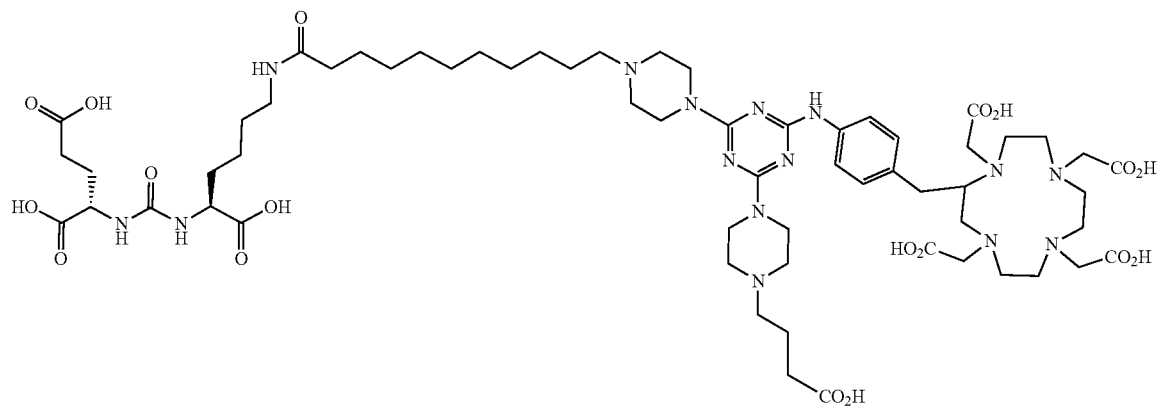 [SMILES: O=C(O)CCCN1CCN(c2nc(Nc3ccc(CC4CN(CC(=O)O)CCN(CC(=O)O)CCN(CC(=O)O)CCN4CC(=O)O)cc3)nc(N3CCN(CCCCCCCCCCC(=O)NCCCC[C@H](NC(=O)N[C@@H](CCC(=O)O)C(=O)O)C(=O)O)CC3)n2)CC1]

To a solution of p-NH2-Bn-DOTA-tetra(t-Bu-ester) (Macrocyclics), (42.4 mg, 0.050 mmol) and cyanuric chloride (9.2 mg, 0.050 mmol) in DCM (2.0 mL) was added DIPEA (0.10 mL). Following stirring at room temperature for 2 hrs, the solvent was removed using a stream of nitrogen to give a residue which was dissolved in DMSO (1.0 mL) prior to the addition of (S)-di-tert-butyl 2-(3-((S)-1-(tert-butoxy)-1-oxo-6-(11-(piperazin-1-yl)undecanamido)hexan-2-yl)ureido)pentanedioate (37 mg, 0.05 mmol) and $K_2CO_3$ (50 mg). The suspension formed was stirred at room temperature for 2 hrs and 4-(piperidin-4-yl)butanoic acid (160 mg) was then added to the suspension. After continuous stirring at room temperature for 72 hrs, the reaction was stopped by lyophilization to afford the protected triazine compound. Deprotection at room temperature, overnight using TFA (4.0 mL) and DCM (1.0 mL), followed by purification using Biotage SP4 and a C18 cartridge gave (2S)-2-(3-((1S)-1-carboxy-5-(11-(4-(4-(4-(3-carboxypropyl)piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (15.3 mg) as a white solid. MS (ESI), 650.8 $(M/2+H)^+$.

Step 2. (2S)-2-(3-((1S)-1-carboxy-5-(11-(4-(4-(4-(3-carboxypropyl)piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid Lutetium Complex To solid (2S)-2-(3-((1S)-1-carboxy-5-(11-(4-(4-(4-(3-carboxypropyl)piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid (6.9 mg, 0.00520 mmol) was added $LuCl_3$ (0.50 mL, 0.0103 mmol/mL, 0.00520 mmol). The reaction mixture was heated at 90° C. for 1 hour and lyophilized to to give (2S)-2-(3-((1S)-1-carboxy-5-(11-(4-(4-(4-(3-carboxypropyl)piperidin-1-yl)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic acid lutetium complex (7.9 mg) as a white solid. MS (ESI), 750.2 $(M/2+H)^+$.

Example 17. $^{68}$Ga Labeling of (2S)-2-(3-((1S)-1-carboxy-5-(11-(4-(4-(dimethylamino)-6-((4-((1,4,7,10-tetrakis(carboxymethyl)-1,4,7,10-tetraazacyclododecan-2-yl)methyl)phenyl)amino)-1,3,5-triazin-2-yl)piperazin-1-yl)undecanamido)pentyl)ureido)pentanedioic Acid

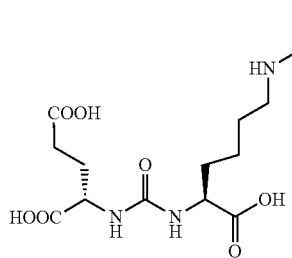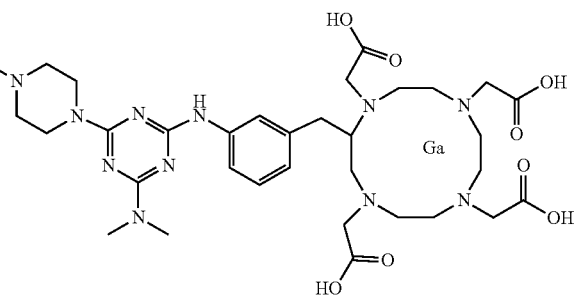

$^{68}$Ga was synthesized using a gallium-68 generator (IDB Holland). A 1 mL fraction of the generator eluate (eluted using 0.6 M HCl suprapure) containing the highest $^{68}$Ga activity was mixed with the reaction mixture that containing 2 µL of the target compound (10 mM solution in DMSO) and 10 µl of ascorbic acid (20% in water). The pH of the reaction mixture was adjusted to be in the pH range of 3.6-3.9 by the addition of approximately 290 µL of an aqueous solution of sodium acetate (2.5 M in water).

The mixture was heated at 90° C. for 10 minutes with stirring. A test sample of the reaction mixture was analyzed by HPLC to confirm complete complexation. The reaction mixture was then diluted with 2 ml saline (0.9% sodium chloride) and loaded onto a pre-conditioned Plexa Cartridge (60 mg, Varian, Bond Elut Plexa). The cartridge was rinsed with 2 mL saline prior to elution of the desired complex using 0.5 mL ethanol. The eluent was passed through a sterile filter (Millipore, Millex-GV) fitted to a syringe followed by washing of the filter by passing 5 mL of saline and 200 µL of phosphate buffer.

The radio-labelled compound was analyzed by HPLC on a Chromolith Performance RP-18e column (100×3 mm Merck KGaA, Darmstadt, Germany) using a linear gradient from 0% to 100% acetonitrile in water (both containing 0.1% TFA) over 5 min. UV absorbance was detected at 214 nm. Under these conditions $^{68}$Ga-MIP-1558 is eluted at about 2.25 min. The radiochemical yields ranged from 77%-97%, average RCP=87% (data corrected for radioactive decay).

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, including the first and last number listed for the range.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A metal complex comprising copper and a compound represented by Formula I

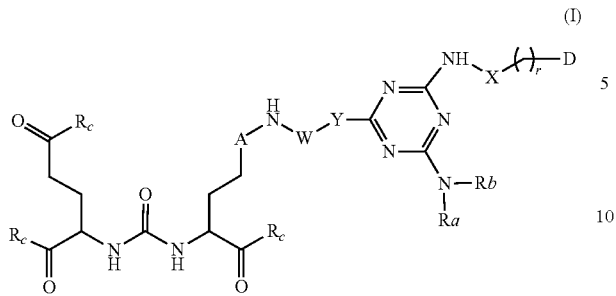
(I)

wherein:

A is $(CHR^1)_m$ or $C(O)$;

W is —C(O)—(CH$_2$)$_p$—; —C(O)[—CH$_2$—CH$_2$—O]$_n$—, —[CH$_2$—CH$_2$—O]$_n$—(CH$_2$)$_2$—, —C(O)—[CH(R$^3$)$_t$]$_q$—, —(CH$_2$)$_m$—O—(CH$_2$)$_n$—, —(CH$_2$)$_m$—S—(CH$_2$)$_n$—, —(CH$_2$)$_m$—S(O)—(CH$_2$)$_n$—, —(CH$_2$)$_m$—S(O)$_2$—(CH$_2$)$_n$—, or —(CH$_2$)$_m$—NR$_a$—(CH$_2$)$_n$—,

Y is —NH—, —NR$^2$— or;

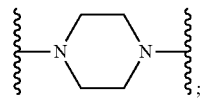

X is —(C$_1$-C$_{10}$)alkylene-(C$_3$-C$_{10}$)arylene, —(C$_3$-C$_{10}$)arylene, —(C$_3$-C$_{10}$)arylene-(C$_1$-C$_{10}$)alkylene-, phenylene, —(C$_1$-C$_{10}$)alkylene-(C$_3$-C$_{10}$)cycloalkylene, —(C$_3$-C$_{10}$)cycloalkylene, or —(C$_3$-C$_{10}$)cycloalkylene-(C$_1$-C$_{10}$)alkylene-;

$R^1$ and $R^2$ are each independently H, —(C$_1$-C$_{10}$)alkyl, —C(O)—(C$_1$-C$_{10}$)alkyl, benzyl, —(C$_3$-C$_{10}$)cycloalkyl, or —(C$_3$-C$_{10}$)aryl;

$R^a$ and $R^b$ are each independently H, —OH, —(C$_1$-C$_{10}$)alkyl, —[CH$_2$—CH$_2$—O]$_n$—(CH$_2$)$_2$-T, —C(O)—(C$_1$-C$_{10}$)alkyl, —(C$_1$-C$_{10}$)alkylene-C(O)—, —(C$_1$-C$_{10}$)alkylene-C(O)—Z, benzyl, —(C$_3$-C$_{10}$)cycloalkyl, —(C$_3$-C$_{10}$)aryl-(C$_1$-C$_{10}$)alkylene, —(C$_3$-C$_{10}$)aryl, halo-(C$_1$-C$_{10}$)alkyl, hydroxy-(C$_1$-C$_{10}$)alkyl, —NH—(C$_1$-C$_{10}$)alkyl, or —(C$_1$-C$_{10}$)alkylene-NR$^d$R$^e$—, or R$^a$ and R$^b$ together with the nitrogen to which they are bonded form a (C$_3$-C$_6$)-heteroaryl or (C$_3$-C$_6$)-heterocycloalkyl;

Z is -OH, —O(C$_1$-C$_{10}$)alkyl,

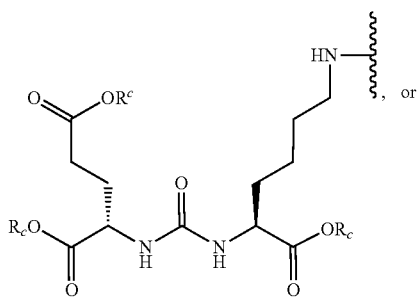

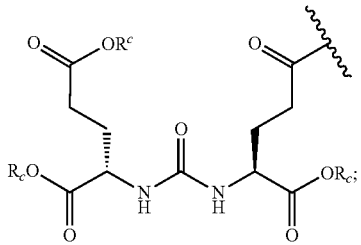

$R^c$ is —OH, —O(C$_1$-C$_{10}$)alkyl, —Obenzyl, —O(C$_3$-C$_{10}$)cycloalkyl, —O(C$_3$-C$_{10}$)aryl, —O—(C$_1$-C$_{10}$)alkylene-(C$_3$-C$_{10}$)aryl, or —O—(C$_1$-C$_{10}$)alkylene-(C$_3$-C$_{10}$)cycloalkyl, $R^3$ is H, halogen, —OH, —NH$_2$, —(CH$_2$)$_p$—COOH, or —(CH$_2$)$_p$—NH$_2$;

T is —H, —OH, —COOH, or —NR$^d$R$^e$;

$R^d$ and $R^e$ are each independently H, bond, —OH, —(C$_1$-C$_{10}$)alkyl, or —(C$_3$-C$_{10}$)heteroaryl-(C$_1$-C$_{10}$)alkylene;

m, n, p, q, t and r are each independently 0, 1, 2, 3, 4, 5, 6, 7, 8 9, or 10; and D is

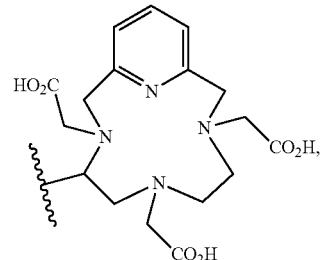

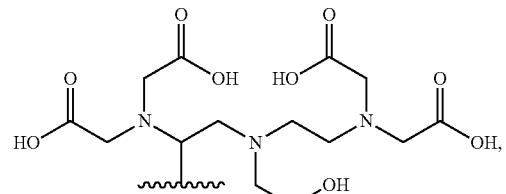

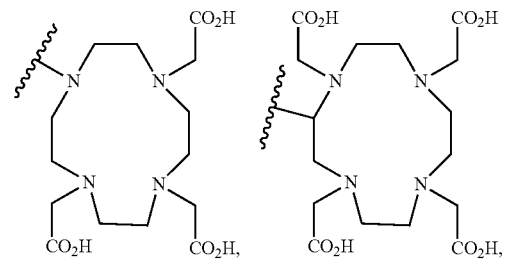

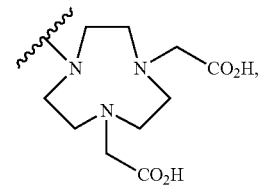

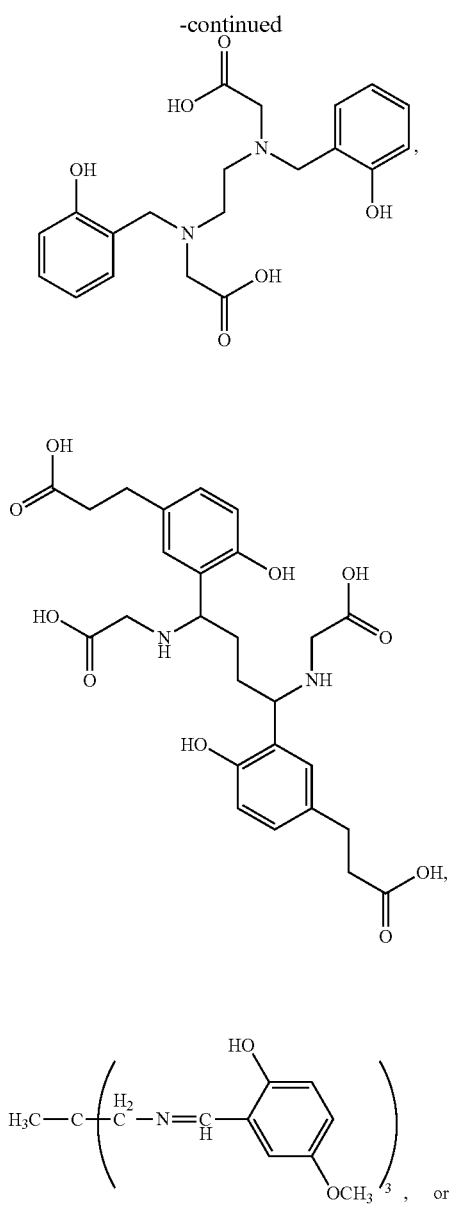

wherein any alkyl, alkylene, aryl, arylene, heteroaryl, heteroarylene, cycloalkyl, cycloalkylene, heterocycloalkyl, or heterocycloalkylene is optionally substituted with 1, 2, or 3 substituent groups selected from the group consisting of —($C_1$-$C_{10}$)alkyl, —($C_1$-$C_{10}$) haloalkyl, —($C_1$-$C_{10}$) aminoalkyl, —($C_1$-$C_{10}$)alkylene-COOH, —($C_1$-$C_{10}$)hydroxyalkyl, —OH, halogen, —$NH_2$, —COOH, —C(O)—($C_1$-$C_{10}$)alkyl, —($C_1$-$C_{10}$)alkylene-C(O)—, —($C_1$-$C_{10}$)alkylene-C(O)—X, —NH—($C_1$-$C_{10}$)alkyl, and —($C_1$-$C_{10}$)alkylene-$NR^dR^e$—, and —$NR^dR^e$.

2. The metal complex of claim 1, wherein X is phenylene, r is 1 and D is

3. The metal complex of claim 2, wherein the compound is represented by Formula (II)

wherein:

A is $(CHR^1)_m$ or $C(O)$;

W is selected from the group consisting of —C(O)—$(CH_2)_p$—; —C(O)[—$CH_2$—$CH_2$—O]$_n$—, —[$CH_2$—$CH_2$—O]$_n$—$(CH_2)_2$—, —C(O)—[CH($R^3$)]$_q$—, —$(CH_2)_m$—O—$(CH_2)_n$—, —$(CH_2)_m$—S—$(CH_2)_n$—, —$(CH_2)_m$—S(O)—$(CH_2)_n$—, —$(CH_2)_m$—S(O)$_2$—$(CH_2)_n$—, and —$(CH_2)_m$—$NR_a$—$(CH_2)_n$—, Y is selected from —NH—, —$NR^2$— or

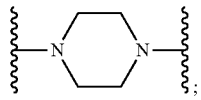

;

$R^1$ and $R^2$ are each independently selected from H, —($C_1$-$C_{10}$)alkyl, —C(O)—($C_1$-$C_{10}$)alkyl, benzyl, —($C_3$-$C_{10}$)cycloalkyl, or —($C_3$-$C_{10}$)aryl;

$R^a$ and $R^b$ are each independently selected from the group consisting of H, —OH, —($C_1$-$C_{10}$)alkyl, —[$CH_2$—$CH_2$—O]$_n$—$(CH_2)_2$-T, —C(O)—($C_1$-$C_{10}$)alkyl, —($C_1$-$C_{10}$)alkylene-C(O)—, —($C_1$-$C_{10}$)alkylene-C(O)—Z, benzyl, —($C_3$-$C_{10}$)cycloalkyl, —($C_3$-$C_{10}$)aryl-($C_1$-$C_{10}$)alkylene, —($C_3$-$C_{10}$)aryl, halo-($C_1$-$C_{10}$)alkyl, hydroxy-($C_1$-$C_{10}$)alkyl, —NH—($C_1$-$C_{10}$)alkyl, and —($C_1$-$C_{10}$)alkylene-$NR^dR^e$—, or $R^a$ and $R^b$ together with the nitrogen to which they are bonded form a ($C_3$-$C_6$)-heteroaryl or ($C_3$-$C_6$)-heterocycloalkyl;

Z is selected from —OH, —O($C_1$-$C_{10}$)alkyl,

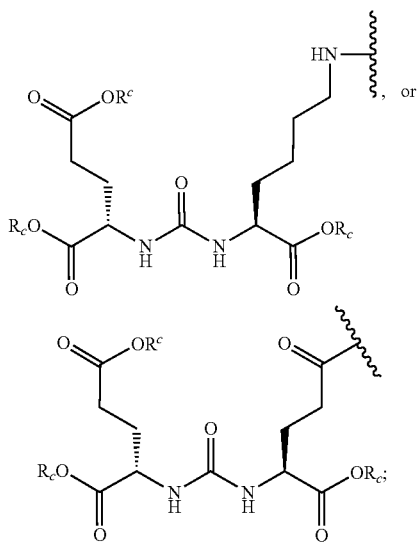

$R^c$ is selected from —OH, —O($C_1$-$C_{10}$)alkyl, —Obenzyl, —O($C_3$-$C_{10}$)cycloalkyl, —O($C_3$-$C_{10}$)aryl, —O—($C_1$-$C_{10}$)alkylene-($C_3$-$C_{10}$)aryl, or —O—($C_1$-$C_{10}$)alkylene-($C_3$-$C_{10}$)cycloalkyl, $R^3$ is selected from H, halogen, —OH, —$NH_2$, —$(CH_2)_p$—COOH, or —$(CH_2)_p$—$NH_2$;

T is selected from —H, —OH, —COOH, or —$NR^dR^e$;

$R^d$ and $R^e$ are each independently selected from H, bond, —OH, —($C_1$-$C_{10}$)alkyl, or —($C_3$-$C_{10}$)heteroaryl-($C_1$-$C_{10}$)alkylene;

m, n, p, q, t and x are each independently 0, 1, 2, 3, 4, 5, 6, 7, 8 9, or 10;

wherein any alkyl, alkylene, aryl, arylene, heteroaryl, heteroarylene, cycloalkyl, cycloalkylene, heterocycloalkyl, or heterocycloalkylene is optionally substituted with 1, 2, or 3 substituent groups selected from the group consisting of —($C_1$-$C_{10}$)alkyl, —($C_1$-$C_{10}$)haloalkyl, —($C_1$-$C_{10}$)aminoalkyl, —($C_1$-$C_{10}$)alkylene-COOH, —($C_1$-$C_{10}$)hydroxyalkyl, —$NH_2$, —COOH, —C(O)—($C_1$-$C_{10}$)alkyl, —($C_1$-$C_{10}$)alkylene-C(O)—, —($C_1$-$C_{10}$)alkylene-C(O)—X, —NH—($C_1$-$C_{10}$)alkyl, and —($C_1$-$C_{10}$)alkylene-$NR^dR^e$—, and —$NR^dR^e$.

4. The metal complex of claim 3, wherein A is $(CHR^1)_m$ and W is —C(O)—$(CH_2)_p$—.

5. The metal complex of claim 4, wherein W is —C(O)—$(CH_2)_7$— or —C(O)—$(CH_2)_{10}$—.

6. The metal complex of claim 4, wherein $R^1$ is hydrogen and m is 2.

7. The metal complex of claim 3, wherein Y is —NH— or

8. The metal complex of claim 7, wherein Y is

9. The metal complex of claim 3, wherein $R^a$ and $R^b$ are each independently hydrogen or methyl and $R^c$ is —OH.

10. The metal complex of claim 3, wherein $R^a$ and $R^b$ together with the nitrogen to which they are bonded form a ($C_3$-$C_6$)-heterocycloalkyl.

11. The metal complex of claim 10, wherein the ($C_3$-$C_6$)-heterocycloalkyl is selected from piperidine, piperazine, morpholine, thiomorpholine, isothiazolidine, isoxazolidine, pyrrolidine, immidazolidine, thiazolidine or oxazolidine.

12. The metal complex of claim 11, wherein the ($C_3$-$C_6$)-heterocycloalkyl is piperidine or 4-(piperidin-4-yl)butanoic acid.

13. The metal complex of claim 3, wherein $R^a$ is —H and $R^b$ is

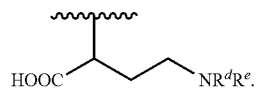

14. The metal complex of claim 3, wherein $R^d$ and $R^e$ are each independently —($C_3$-$C_{10}$)heteroaryl-($C_1$-$C_{10}$)alkylene.

15. The metal complex of claim 3, wherein $R^d$ and $R^e$ are each independently
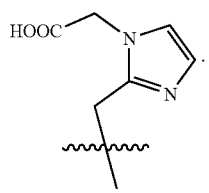 [SMILES: *Cc1nccn1CC(=O)O]
16. The metal complex of claim 1, wherein the copper is $^{64}$Cu or $^{67}$Cu.
17. A pharmaceutical composition comprising the metal complex of claim 1, or a pharmaceutically acceptable salt, solvate, or ester thereof, and a pharmaceutically acceptable carrier.
18. The metal complex of claim 1, which is:
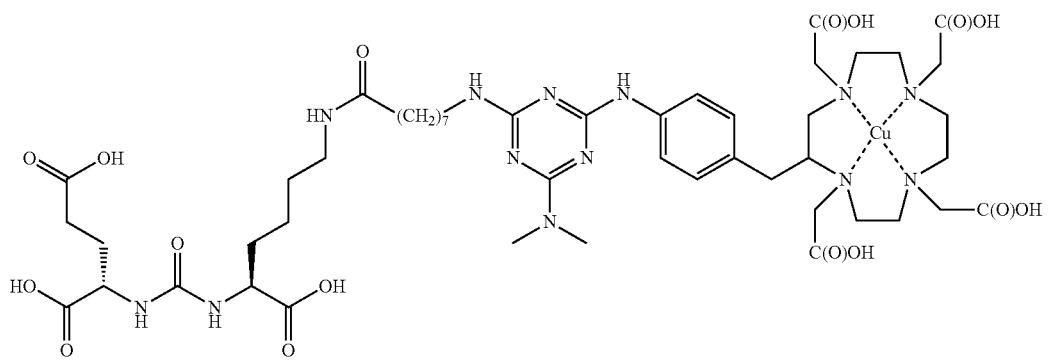
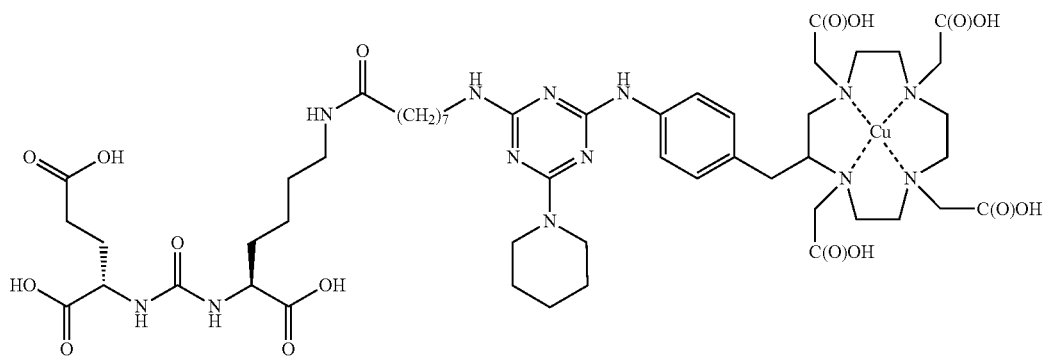
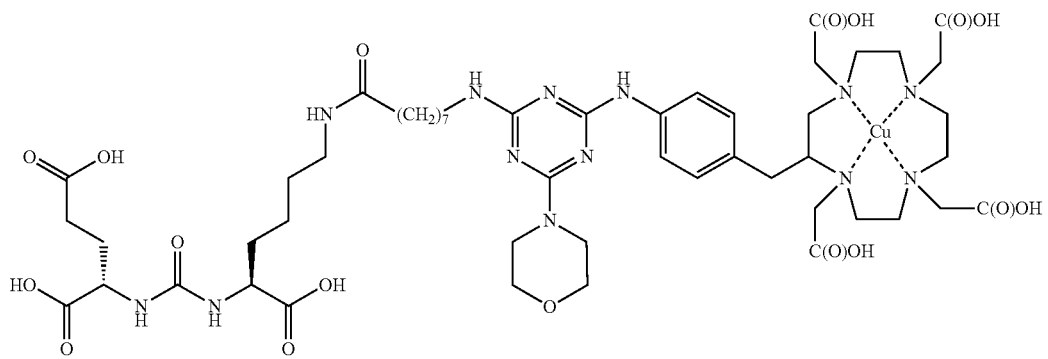

121 122
-continued
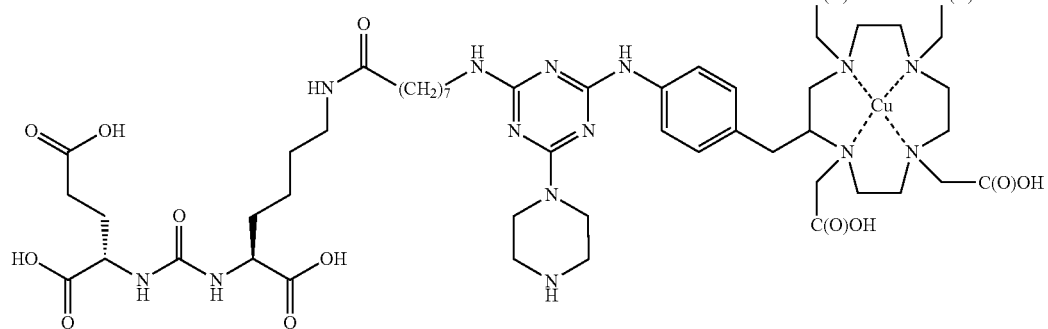
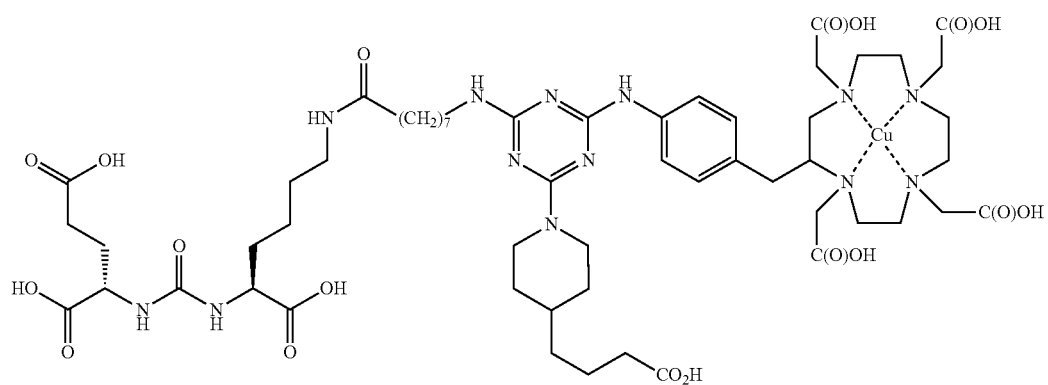
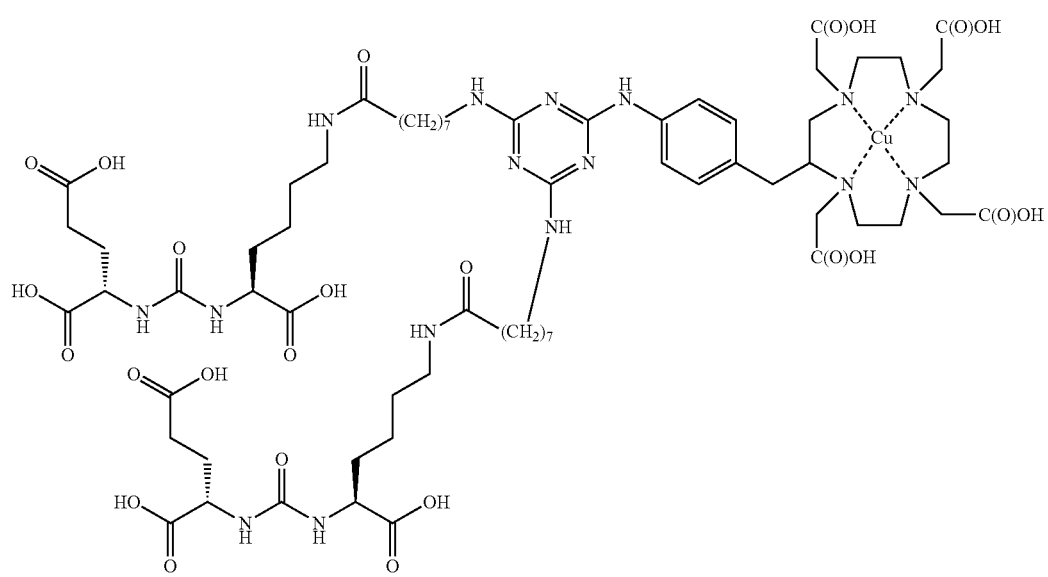
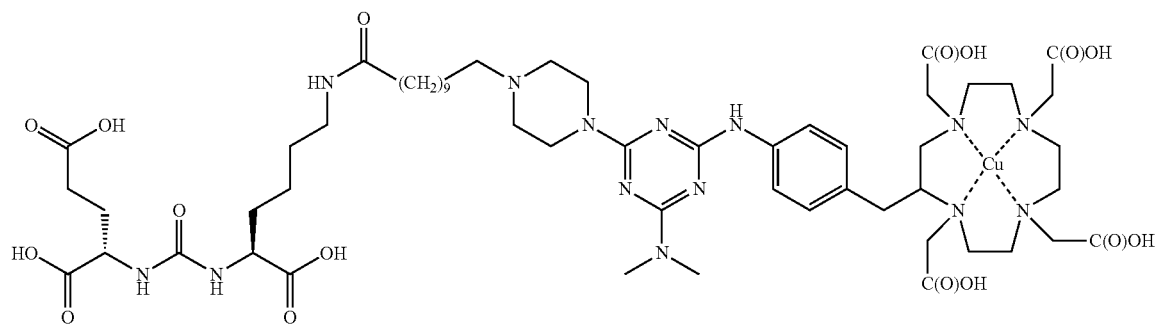

-continued
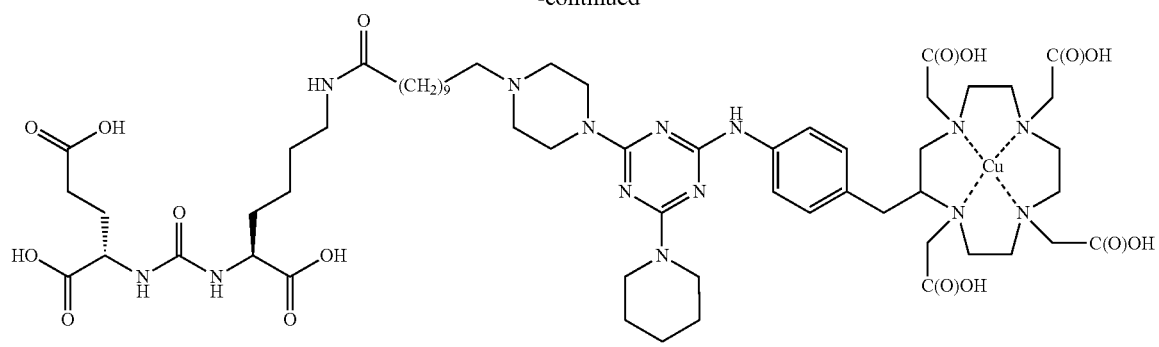
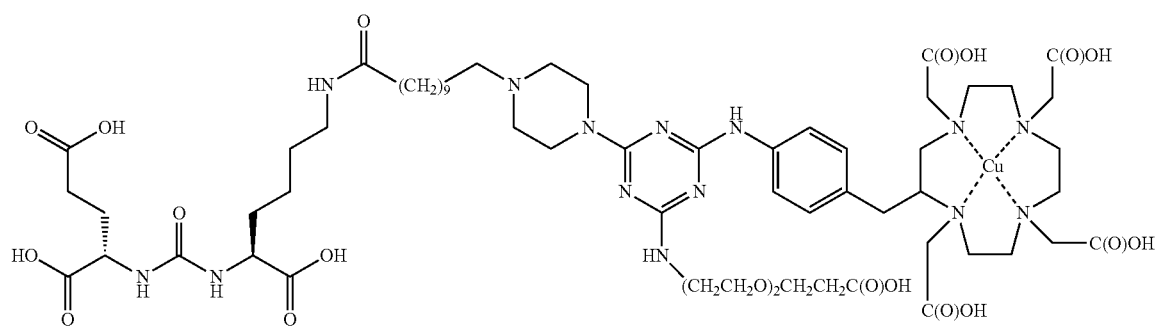
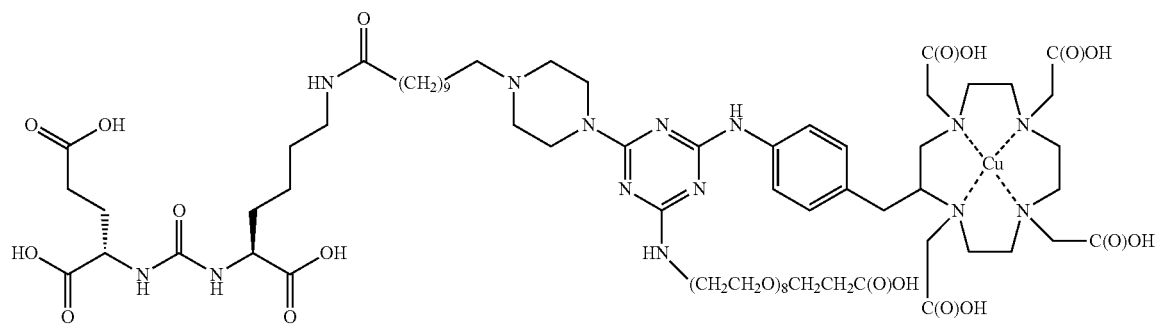
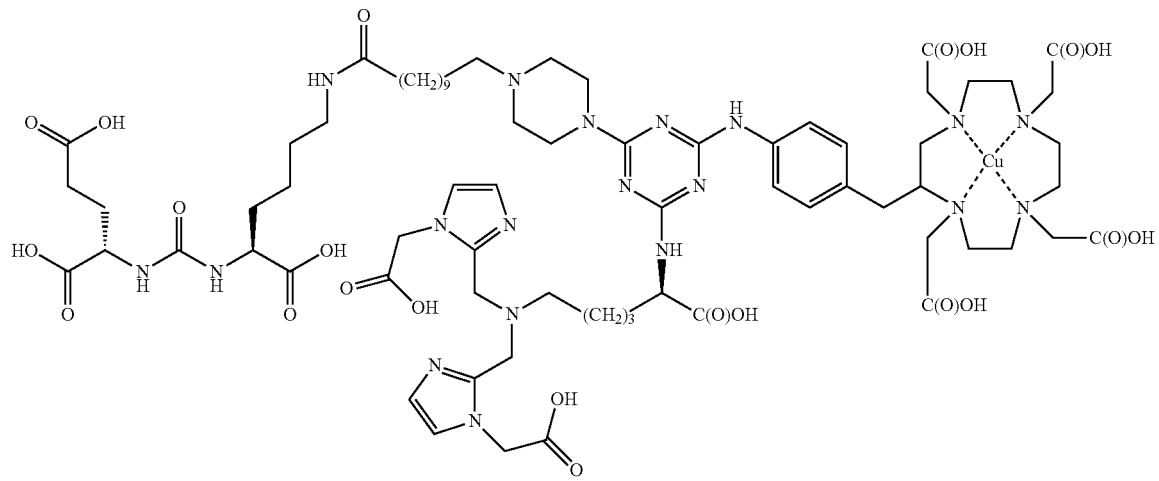

125 126
-continued
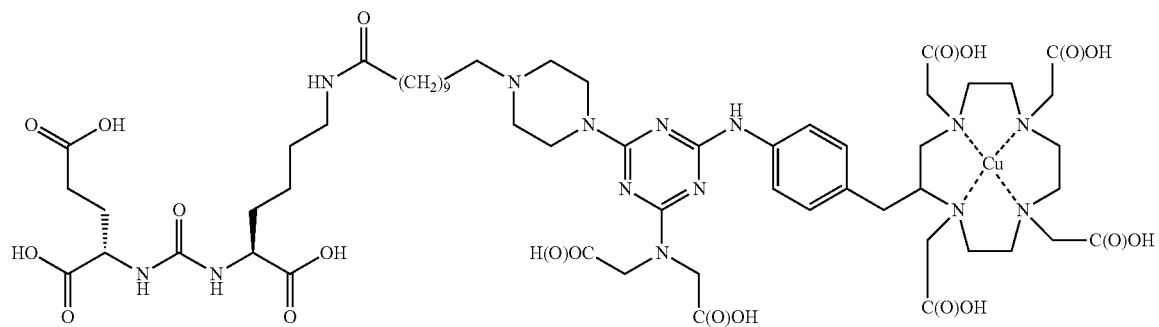
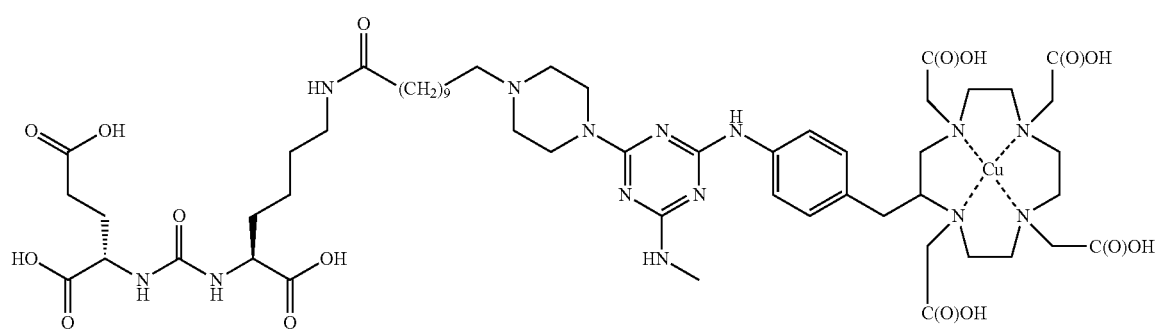
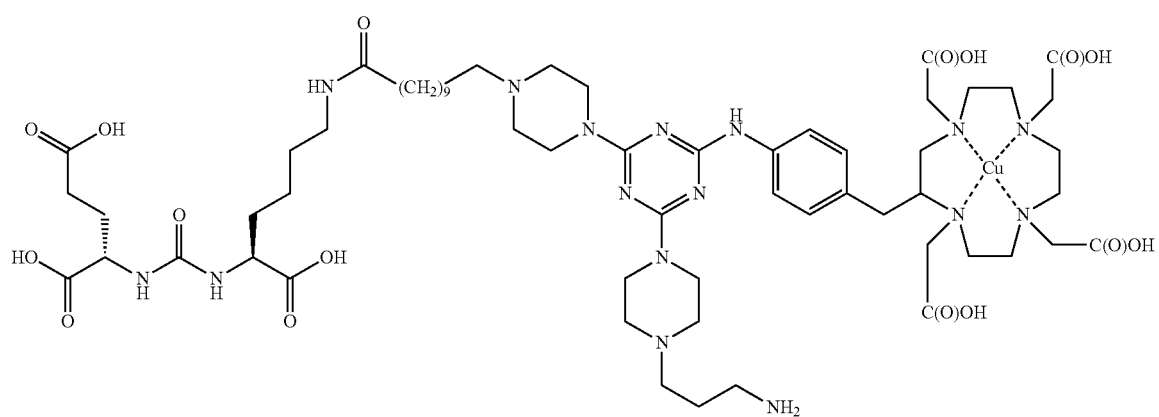
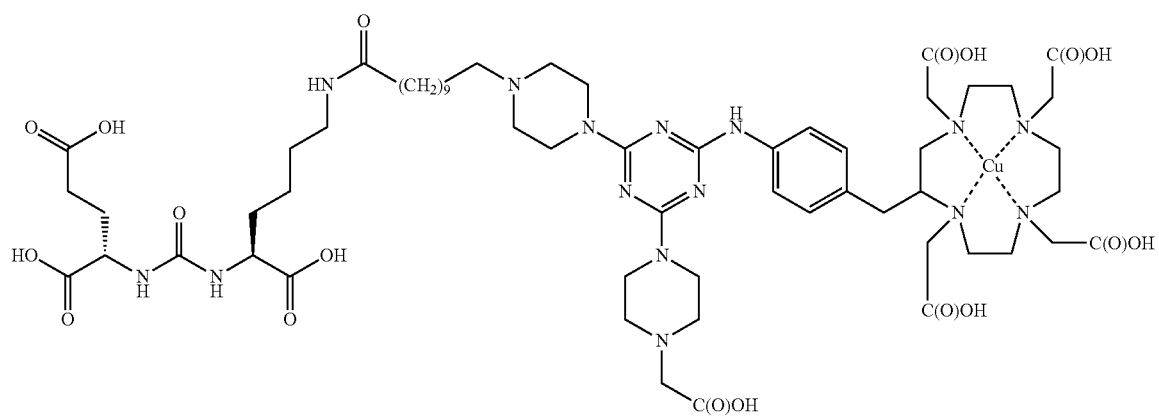

-continued
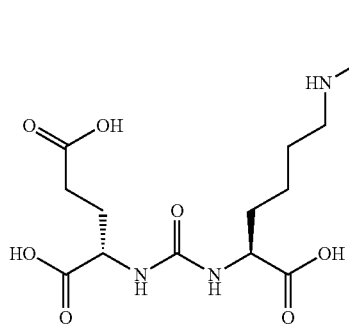 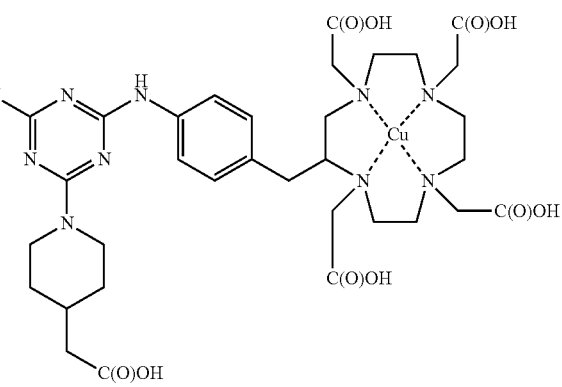
or a pharmaceutically acceptable salt or solvate thereof.
19. The metal complex of claim 18, wherein the Cu is $^{64}$Cu or $^{67}$Cu.
20. A pharmaceutical composition comprising the metal complex of claim 18, or a pharmaceutically acceptable salt, solvate, or ester thereof, and a pharmaceutically acceptable carrier.
* * * * *